(12) United States Patent
Liao

(10) Patent No.: US 8,430,928 B2
(45) Date of Patent: Apr. 30, 2013

(54) COPOLYMERS FOR INTRAOCULAR LENS SYSTEMS

(75) Inventor: Xiugao Liao, Irvine, CA (US)

(73) Assignee: Visiogen, Inc., Santa Ana, CA (US)

( * ) Notice: Subject to any disclaimer, the term of this patent is extended or adjusted under 35 U.S.C. 154(b) by 0 days.

(21) Appl. No.: 13/489,790

(22) Filed: Jun. 6, 2012

(65) Prior Publication Data

US 2012/0245684 A1 Sep. 27, 2012

Related U.S. Application Data

(62) Division of application No. 12/574,498, filed on Oct. 6, 2009, now Pat. No. 8,222, 360.

(60) Provisional application No. 61/152,496, filed on Feb. 13, 2009.

(51) Int. Cl.
*A61F 2/16* (2006.01)
*C08F 130/08* (2006.01)

(52) U.S. Cl.
USPC .......................................... 623/6.11; 526/279

(58) Field of Classification Search .................. None
See application file for complete search history.

(56) References Cited

U.S. PATENT DOCUMENTS

| | | | |
|---|---|---|---|
| 4,525,563 A | 6/1985 | Shibata et al. |
| 4,761,452 A | 8/1988 | Itoh et al. |
| 4,829,137 A | 5/1989 | Stoyan |
| 4,834,750 A | 5/1989 | Gupta |
| 4,920,180 A | 4/1990 | Toyoshima et al. |
| 4,977,229 A | 12/1990 | Culberson et al. |
| 5,002,979 A | 3/1991 | Stoyan |
| 5,041,511 A | 8/1991 | Yanagawa et al. |
| 5,077,362 A | 12/1991 | Watanabe et al. |
| 5,290,892 A | 3/1994 | Namdaran et al. |
| 5,331,073 A | 7/1994 | Weinschenk, III et al. |
| 5,582,882 A | 12/1996 | Kang et al. |
| 5,585,035 A | 12/1996 | Nerad et al. |
| 5,585,424 A | 12/1996 | Ohata et al. |
| 5,599,883 A | 2/1997 | Ohsugi et al. |
| 5,603,774 A | 2/1997 | LeBoeuf et al. |
| 5,652,821 A | 7/1997 | Okumi et al. |

(Continued)

FOREIGN PATENT DOCUMENTS

| CA | 1307071 C | 9/1992 |
|---|---|---|
| CN | 101293963 A | 10/2008 |

(Continued)

OTHER PUBLICATIONS

International Search Report and Written Opinion for Application No. PCT/US2010/023946, mailed on Feb. 22, 2011, 10 pages.

(Continued)

*Primary Examiner* — Robert S Loewe
(74) *Attorney, Agent, or Firm* — Visiogen, Inc.

(57) ABSTRACT

Some embodiments provide a copolymer comprising: an acrylate recurring unit and an optionally substituted vinylaryl recurring unit, wherein a portion of at least one of the recurring units comprises a vinyldialkylsiloxy pendant group. The copolymers may be useful as soft acrylic haptics for intraocular lenses. Some embodiments further relate to intraocular lenses having a hydrophobic soft acrylic optic and a silicone haptic, such as a dual optic accommodative lens a having hydrophobic soft acrylic anterior and posterior optic bodies and a silicone haptic. Related copolymeric composite materials as well as additional embodiments of intraocular lenses, are also described herein.

7 Claims, 26 Drawing Sheets

U.S. PATENT DOCUMENTS

| | | | |
|---|---|---|---|
| 5,674,569 A | 10/1997 | Ohsugi et al. |
| 5,674,960 A | 10/1997 | Namdaran et al. |
| 5,693,095 A | 12/1997 | Freeman et al. |
| 5,733,978 A | 3/1998 | Kobayashi |
| 5,789,463 A | 8/1998 | Odagiri et al. |
| 5,789,485 A | 8/1998 | Kobayashi et al. |
| 5,814,680 A | 9/1998 | Imafuku et al. |
| 5,821,306 A | 10/1998 | Hodd |
| 5,833,890 A | 11/1998 | Fedorov et al. |
| 6,136,874 A | 10/2000 | Dyer et al. |
| 6,187,042 B1 | 2/2001 | Sheets, Jr. et al. |
| 6,210,438 B1 | 4/2001 | Sheets, Jr. et al. |
| 6,245,106 B1 | 6/2001 | Makker et al. |
| 6,271,281 B1 | 8/2001 | Liao et al. |
| 6,307,081 B1 | 10/2001 | Takiuchi et al. |
| 6,313,187 B2 | 11/2001 | LeBoeuf et al. |
| 6,353,069 B1 | 3/2002 | Freeman et al. |
| 6,406,494 B1 | 6/2002 | Laguette et al. |
| 6,450,642 B1 | 9/2002 | Jethmalani et al. |
| 6,566,479 B1 | 5/2003 | Bublewitz et al. |
| 6,599,317 B1 | 7/2003 | Weinschenk, III et al. |
| 6,645,246 B1 | 11/2003 | Weinschenk, III et al. |
| 6,737,448 B2 | 5/2004 | Liao |
| 6,815,075 B2 | 11/2004 | Kasai et al. |
| 6,852,820 B2 | 2/2005 | Mentak |
| 6,866,742 B2 | 3/2005 | Hashiguchi et al. |
| 6,884,261 B2 | 4/2005 | Zadno-Azizi et al. |
| 6,887,402 B2 | 5/2005 | Klemm et al. |
| 6,890,458 B2 | 5/2005 | Weber et al. |
| 6,911,514 B2 | 6/2005 | Bublewitz et al. |
| 6,986,857 B2 | 1/2006 | Klemm et al. |
| 7,141,248 B2 | 11/2006 | Hodd et al. |
| 7,160,592 B2 | 1/2007 | Rypacek et al. |
| 7,235,195 B2 | 6/2007 | Andino et al. |
| 7,276,544 B2 | 10/2007 | Lai et al. |
| 7,297,160 B2 | 11/2007 | Salamone et al. |
| 7,297,726 B2 | 11/2007 | Pennings et al. |
| 7,364,768 B2 | 4/2008 | Rypacek et al. |
| 7,423,108 B2 | 9/2008 | Kunzler et al. |
| 2002/0074086 A1 | 6/2002 | Nakamura et al. |
| 2002/0107568 A1 | 8/2002 | Zadno-Azizi et al. |
| 2003/0116273 A1 | 6/2003 | Nakamura et al. |
| 2003/0171505 A1 | 9/2003 | Bublewitz et al. |
| 2004/0020597 A1 | 2/2004 | Hashiguchi et al. |
| 2005/0279995 A1 | 12/2005 | Shin et al. |
| 2006/0006380 A1 | 1/2006 | Shin et al. |
| 2007/0009674 A1 | 1/2007 | Okubo et al. |
| 2007/0100103 A1 | 5/2007 | Lim et al. |
| 2008/0160166 A1 | 7/2008 | Rypacek et al. |
| 2010/0048818 A1 | 2/2010 | Kennedy et al. |

FOREIGN PATENT DOCUMENTS

| | | |
|---|---|---|
| EP | 1312659 A1 | 5/2003 |
| EP | 1395417 A2 | 3/2004 |
| EP | 1588829 A2 | 10/2005 |
| EP | 1401634 B1 | 10/2006 |
| EP | 1492581 B1 | 12/2006 |
| EP | 1764405 A1 | 3/2007 |
| JP | 63172117 A | 7/1988 |
| JP | 7218734 A | 8/1995 |
| JP | 7228639 A | 8/1995 |
| JP | 7278255 A | 10/1995 |
| JP | 8012341 A | 1/1996 |
| JP | 8301959 A | 11/1996 |
| JP | 2001354773 A | 12/2001 |
| JP | 2002119308 A | 4/2002 |
| JP | 2003081730 A | 3/2003 |
| JP | 2004196956 A | 7/2004 |
| JP | 2004269564 A | 9/2004 |
| WO | WO2008112190 A1 | 9/2008 |

OTHER PUBLICATIONS

Jewrajka S.K., et al., "Novel Biostable and Biocompatible Amphiphilic Membranes," Journal of Biomedical Materials Research Part A, 2008, vol. 87 (1), pp. 69-77.

Kang J., et al., "Third-Generation Amphiphilic Conetworks. III. Permeabilities and Mechanical Properties," Journal of Polymer Science, 2007, vol. 45, pp. 4276-4283.

Kanie T., et al., "Adding Silanes to MMA: The Effects on the Water Absorption, Adhesive Strength and Mechanical Properties of Acrylic Denture Base Resins," Dental Materials Journal, 2000, vol. 19 (4), pp. 329-337.

Mahkam M., et al., "pH-Sensitive Hydrogel Containing Acetaminophen Silyl Ethers for Colon-Specific Drug Delivery," Designed Monomers and Polymers, 2006, vol. 9 (6), pp. 607-615.

Mihailescu C., et al., "Etude Preliminaire Concernant L'obtention De Compositions Adhesives Biocorlpatibles," COFrRoCA, Sep. 22-26, 2004, Slanic Moldova, Bacau, Romania.

Sawada H., et al., "Syntheses and Properties of Fluoroalkylated Oligomers Containing Oligo(oxyethylene) Units," Journal of Japan Oil Chemists' Society, 1998, vol. 47 (7), pp. 685-694.

Suzuki T., et al., "Poly(dimethylsiloxane) Macromonomers Having Both Alkenyl and Polymerizable Groups. Application to Crosslinkable Copolymers," Polymer, 1988, vol. 29 (11), pp. 2095-2099.

COPOLYMERS FOR INTRAOCULAR LENS SYSTEMS

This application is a divisional application of and claims priority to U.S. application Ser. No. 12/574,498 filed on Oct. 6, 2009 now U.S. Pat. No. 8,222,360, which is hereby incorporated by reference in its entirety.

CROSS REFERENCE TO RELATED APPLICATIONS

This application claims priority to U.S. Provisional Application No. 61/152,496, filed Feb. 13, 2009 by Charles Liao, for "Acrylic Material That Can Be Coupled to Silicone Material." This document is incorporated by reference herein in its entirety.

BACKGROUND OF THE INVENTION

1. Field of the Invention

Some embodiments provided herein are related to copolymers, such as acrylate copolymers. In some embodiments, these copolymers may be used in lenses such as intraocular lenses.

2. Description of the Related Art

The vast majority of cataract operations involve the implantation of an artificial lens following cataract removal. Typically these lenses have a fixed focal length or, in the case of bifocal or multifocal lenses, have several different fixed focal lengths. Such fixed focal-length lenses lack the ability of the natural lens to dynamically change the refractive power of the eye. While silicone components of these lenses may impart flexibility, hydrophobic soft acrylic copolymeric components may have a higher refractive index and controlled recoverability, as well as improved optical properties. Combining hydrophobic soft acrylic copolymeric components and silicone components in a single accommodative intraocular lens may not only significantly reduce lens thickness and improve optical properties, but also maintain the haptic flexibility.

SUMMARY OF THE INVENTION

Some embodiments provide an intraocular lens comprising: an optic body comprising a first hydrophobic soft acrylic copolymer; and a haptic comprising a first silicone connected to the optic body.

Some embodiments provide a copolymer comprising: an acrylate recurring unit and an optionally substituted vinylaryl recurring unit, wherein a portion of at least one of the recurring units comprises a vinyldialkylsiloxy pendant group.

In some embodiments, the copolymer comprises the following recurring units:

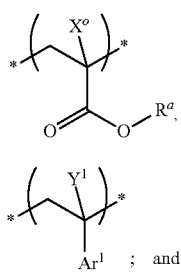

Formula 1

Formula 3

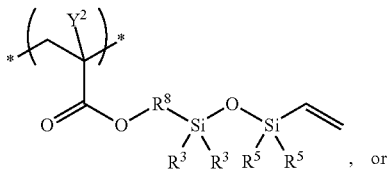

Formula 4

Formula 5 wherein $R^a$ is optionally substituted $C_{1-12}$ alkyl, $-Ph^a$, $-O-Ph^a$, $-R^b-Ph^a$, or $-R^b-O-Ph^a$, wherein $-Ph^a$ is optionally substituted phenyl, and $R^b$ is optionally substituted $C_{1-4}$ alkyl; $X^o$ is H or $C_{1-4}$ alkyl; $Y^1$, $Y^2$, and $Y^3$ are independently H or $C_{1-4}$ alkyl; $Ar^1$ and $Ar^2$ are independently an optionally substituted aromatic group or an optionally substituted heteroaromatic group; each $R^3$ and each $R^4$ is independently $C_{1-4}$ alkyl or

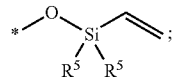

each $R^5$ and each $R^6$ is independently $C_{1-4}$ alkyl; $R^7$ is a covalent bond or $C_{1-6}$ alkyl; and $R^8$ is $C_{1-6}$ alkyl.

Some embodiments provide a copolymeric composite material comprising: an acrylic component comprising a copolymer described herein; and a silicone component; and a plurality of silicon-carbon covalent bonds between a silicon atom of the silicone component and a carbon atom of the vinyldialkylsiloxy pendant group of the acrylic component.

Some embodiments provide an intraocular lens comprising a copolymeric composite material described herein. Some embodiments provide an intraocular lens comprising: an anterior viewing element; a posterior viewing element; and a biasing structure connecting the anterior viewing element to the posterior viewing element; wherein the biasing structure provides a variable spacing between the anterior viewing element and the posterior viewing element; wherein at least a portion of at least one of: the anterior viewing element and the posterior viewing element comprises at least a portion of the acrylic component; at least a portion of at least one of the anterior viewing element, the posterior viewing element, and the biasing structure comprises at least a portion of the silicone component; and at least a portion of at least one of the anterior viewing element, the posterior viewing element, and the biasing structure comprises at least a portion of the plurality of silicon-carbon covalent bonds.

Some embodiments provide an intraocular lens comprising: an optic body comprising a first hydrophobic soft acrylic copolymer; and a haptic comprising a first silicone connected to the optic body. Some embodiments provided herein are related to hydrophobic soft acrylic copolymers, such as hydrophobic soft acrylic copolymers consisting of alkyl acrylate, alkyl methacrylate, styrene derivatives, and methacryloxyalkyltris(vinyldimethylsiloxy)silane. In some embodiments, these hydrophobic soft acrylic copolymers can be used in optic implants such as intraocular lenses. In some embodiments these hydrophobic soft acrylic copolymers may be useful for accommodative lenses wherein all or a portion of an optic body comprises the hydrophobic soft acrylic copolymer and all or a portion of the haptics comprise a silicone.

Some embodiments provide an intraocular lens comprising a copolymeric composite material described herein.

All of these aspects are intended to be within the scope of the invention herein disclosed. These and other aspects of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention, certain preferred embodiments and modifications thereof will become apparent to those skilled in the art from the detailed description herein having reference to the figures that follow, of which.

DETAILED DESCRIPTION OF THE PREFERRED EMBODIMENTS

Figure 1:
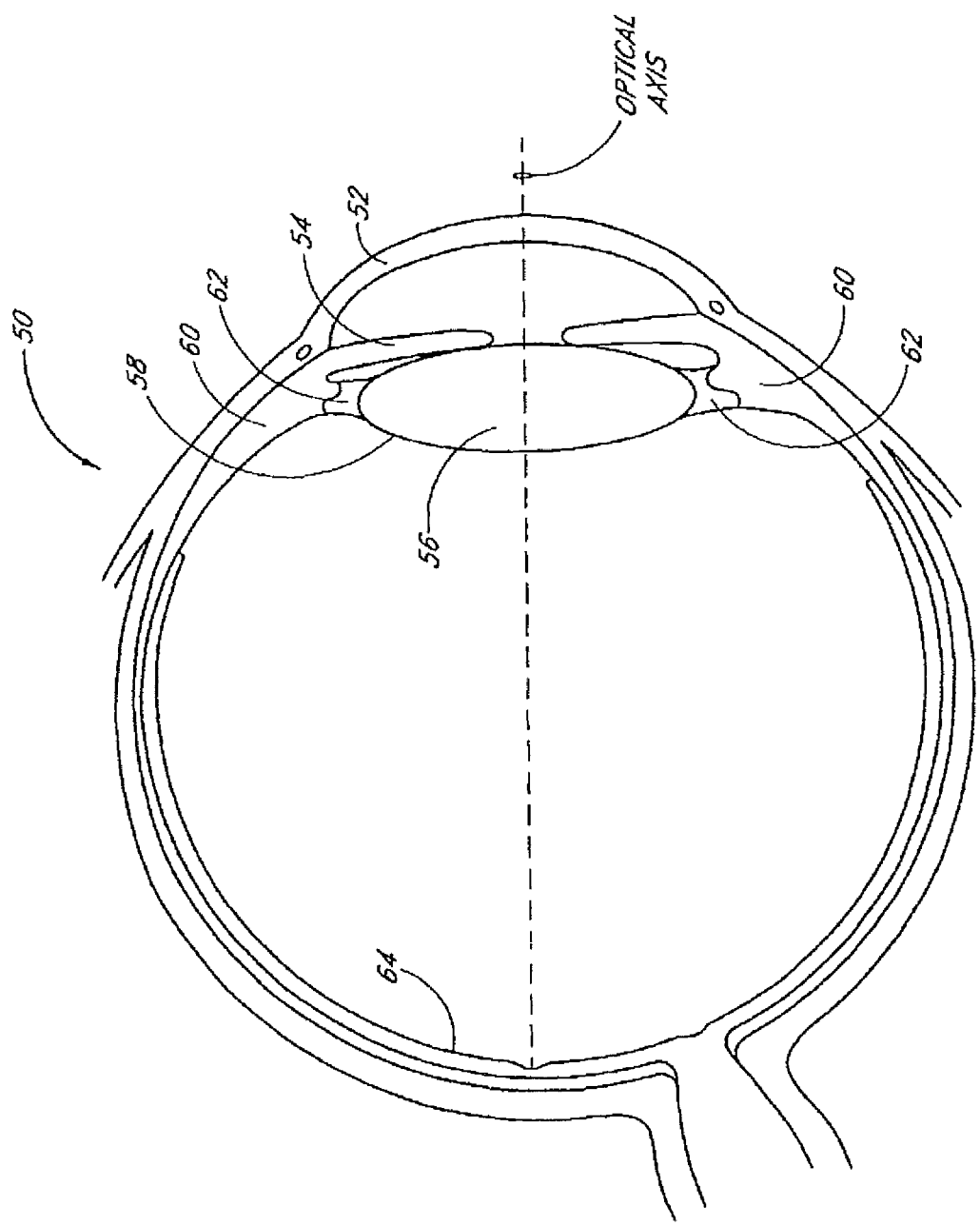
FIG. 1 is a sectional view of the human eye, with the lens in the unaccommodated state.

As used herein, the term "copolymeric composite material" has the ordinary meaning understood by a person of ordinary skill in the art. In some embodiments, the term "copolymeric composite material" refers to a material comprising two at least two distinct polymeric or copolymeric phases having distinct compositions, such as an acrylic copolymer and a silicone polymer.

As used herein, the term "silicone component" has the ordinary meaning understood by a person of ordinary skill in the art. In some embodiments, the term "silicone component" refers to a polymeric material comprising silicon, carbon, hydrogen, and oxygen. A polysiloxane is an example of a silicone, and may refer a polymeric comprising a recurring —Si—O— unit, where the silicon atom may bear two groups selected from: hydrogen and a hydrocarbon group. Poly(dimethylsiloxane) is an example of a polysiloxane.

As used herein, the term "acrylic component" or "acrylic copolymer" has the ordinary meaning understood by a person of ordinary skill in the art. In some embodiments, the term "acrylic component" refers to a component of a device that comprises an "acrylic copolymer." In some embodiments, an "acrylic copolymer" comprises an acrylate recurring unit. Note that an "acrylic copolymer" or an "acrylic component" may also contain other functional groups in addition to just the acrylic functionality.

As used herein, the term "acrylate recurring unit" has the ordinary meaning understood by a person of ordinary skill in the art. In some embodiments, the term "acrylate recurring unit" may refer to a recurring unit derived from alkyl acrylate monomer, derived from an alkyl alkylacrylate acid monomer, derived from a monomer which is an ester of acrylic acid, or derived from a monomer which is an ester of an alkylacrylic acid.

Some non-limiting examples of monomers which are esters of acrylic acid include methyl acrylate, ethyl acrylate, propyl acrylate isomers (e.g n-propyl acrylate, isopropyl acrylate, etc.) butyl acrylate isomers, pentyl acrylate isomers, hexyl acrylate isomers, heptyl acrylate isomers, octyl acrylate isomers, nonyl acrylate isomer, decyl acrylate isomers, undecyl acrylate isomers, dodecyl acrylate isomer, tridecyl acrylate isomers, phenyl acrylate: (vinyldialkylsiloxy)alkyl esters of acrylic acid; etc.

Some non-limiting examples of alkylacrylic acids include methacrylic acid, ethylacrylic acid, propylacrylic acid isomer (e.g. n-propyl acrylate, isopropyl acrylate, etc.), butylacrylic acid isomers, pentylacrylic acid isomers, etc.

Some non-limiting examples of monomers which are esters of alkylacrylic acid include esters of methacrylic acid such as methyl methacrylate, ethyl methacrylate, propyl methacrylate isomers (e.g n-propyl methacrylate, isopropyl methacrylate, etc.) butyl methacrylate isomers, pentyl methacrylate isomers, hexyl methacrylate isomers, heptyl methacrylate isomers, octyl methacrylate isomers, nonyl methacrylate isomer, decyl methacrylate isomers, undecyl methacrylate isomers, dodecyl methacrylate isomer, tridecyl methacrylate isomers, phenyl methacrylate, etc.; esters of ethylacrylic acid such as methyl ethylacrylate, ethyl ethylacrylate, propyl ethylacrylate isomers (e.g n-propyl ethylacrylate, isopropyl ethylacrylate, etc.) butyl ethylacrylate isomers, pentyl ethylacrylate isomers, hexyl ethylacrylate isomers, heptyl ethylacrylate isomers, octyl ethylacrylate isomers, nonyl ethylacrylate isomer, decyl ethylacrylate isomers, undecyl ethylacrylate isomers, dodecyl ethylacrylate isomer, tridecyl ethylacrylate isomers, phenyl ethacrylate etc.; esters of propylacrylic acid isomers such as methyl propylacrylate isomers, ethyl propylacrylate isomers, propyl propylacrylate isomers (e.g n-propyl propylacrylate, isopropyl propylacrylate, etc.) butyl propylacrylate isomers, pentyl propylacrylate isomers, hexyl propylacrylate isomers, heptyl propylacrylate isomers, octyl propylacrylate isomers, nonyl propylacrylate isomer, decyl propylacrylate isomers, undecyl propylacrylate isomers, dodecyl propylacrylate isomer, tridecyl propylacrylate isomers, phenyl propylacrylate isomers, etc.; esters of butylacrylic acid isomers such as methyl butylacrylate isomers, ethyl butylacrylate isomers, propyl butylacrylate isomers (e.g n-propyl butylacrylate, isopropyl butylacrylate, etc.) butyl butylacrylate isomers, pentyl butylacrylate isomers, hexyl butylacrylate isomers, heptyl butylacrylate isomers, octyl butylacrylate isomers, nonyl butylacrylate isomer, decyl butylacrylate isomers, undecyl butylacrylate isomers, dodecyl butylacrylate isomer, tridecyl butylacrylate isomers, phenyl butylacrylate isomers etc.; esters of pentylacrylic acid isomers such as methyl pentylacrylate isomers, ethyl pentylacrylate isomers, propyl pentylacrylate isomers (e.g n-propyl pentylacrylate, isopropyl pentylacrylate, etc.) butyl pentylacrylate isomers, pentyl pentylacrylate isomers, hexyl pentylacrylate isomers, heptyl pentylacrylate isomers, octyl pentylacrylate isomers, nonyl pentylacrylate isomer, decyl pentylacrylate isomers, undecyl pentylacrylate isomers, dodecyl pentylacrylate isomer, tridecyl pentylacrylate isomers, phenyl pentylacrylate isomers, etc.; (vinyldialkylsiloxy)alkyl esters of alkyl acrylic acids; etc.

As used herein the term "aryl" has the ordinary meaning understood by a person of ordinary skill in the art. In some embodiments, the term "aryl" may refer to an aromatic ring or aromatic ring system such as phenyl, naphthyl, etc. The term "heteroaryl" also has the meaning understood by a person of ordinary skill in the art, and in some embodiments, may refer to an "aryl" which has one or more heteroatoms in the ring or ring system. Examples of "heteroaryl" may include, but are not limited to, pyridinyl, furyl, thienyl, oxazolyl, thiazolyl, imidazolyl, quinolinyl, benzofuranyl, benzothienyl, benzooxazolyl, benzothiazolyl, benzoimidazolyl, etc.

As used herein the term "vinylaryl recurring unit" has the ordinary meaning understood by a person of ordinary skill in the art. In some embodiments, the term "vinylaryl recurring unit" may refer to a recurring unit derived from an optionally substituted vinylaryl or optionally substituted vinylheteroaryl monomer. In some embodiments, the recurring unit may be derived from a polymerization reaction of the vinyl group to form a two carbon alkyl recurring unit with an aryl pendant group. In these embodiments, the vinyl group may optionally have one or substituents, and the aryl group may optionally have one or more substituents. Examples may include monomers derived from optionally substituted vinylphenyl, or styrene, such as methyl styrene, (vinyl)methylphenyl, (vinyl)alkylsiloxyphenyl, etc.; monomers derived from optionally substituted vinylnapthyl; monomers derived from optionally substituted vinylpyridine; monomers derived from optionally substituted vinylfuran; monomers derived from optionally substituted vinylthiophene; monomers derived from optionally substituted vinylimidazole; monomers derived from optionally substituted vinylthiazole; monomers derived from optionally substituted vinyloxazole; etc.

Unless otherwise indicated, when a chemical structural feature such as alkyl, vinylarl, aryl, phenyl, heteroaryl, etc. is referred to as being "optionally substituted," it is meant that the feature may have no substituents (i.e. be unsubstituted) or may have one or more substituents. A feature that is "substituted" has one or more substituents. The term "substituent" has the ordinary meaning known to one of ordinary skill in the art. In some embodiments, the substituent is an ordinary organic moiety known in the art, which may have a molecular weight (e.g. the sum of the atomic masses of the atoms of the substituent) of less than about 500, about 300, about 200, about 100, or about 50. In some embodiments, the molecular weight of the substituent may be less than about 500. In some embodiments, the substituent comprises: about 0-30, about 0-20, about 0-10, or about 0-5 carbon atoms; and about 0-30, about 0-20, about 0-10, or about 0-5 heteroatoms independently selected from: N, O, S, P, Si, F, Cl, Br, I, and combinations thereof; provided that the substituent comprises at least one atom selected from: C, N, O, S, Si, F, Cl, Br, and I. In some embodiments, the substituent comprises: about 0-20 carbon atoms; and about 0-30, about 0-20, about 0-10, or about 0-5 heteroatoms independently selected from: N, O, S, P, Si and combinations thereof, and the substituent may be substituted by one or more halogen selected from: F, Cl, and Br. In some embodiments, the substituent may be halogen atom such as F, Cl, or Br. Examples of substituents include, but are not limited to, alkyl, alkenyl, alkynyl, carbazolyl, cycloalkyl, cycloalkenyl, cycloalkynyl, aryl, diarylamino, heteroaryl, heteroalicyclyl, aralkyl, heteroaralkyl, (heteroalicyclyl)alkyl, hydroxy, protected hydroxy, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, and amino, including mono- and di-substituted amino groups, and the protected derivatives thereof.

As used herein, the term "alkyl" refers to a moiety composed of carbon and hydrogen containing no double or triple bonds. Alkyl may be linear, branched, cyclic, or a combination thereof, may be bonded to any other number of moieties (e.g. be bonded to 1 other group, such as —$CH_3$, 2 other groups, such as —$CH_2$—, or any number of other groups) that the structure may bear, and in some embodiments, may contain from one to thirty-five carbon atoms. Examples of alkyl groups include but are not limited to $CH_3$ (e.g. methyl), $C_2H_5$ (e.g. ethyl), $C_3H_7$ (e.g. propyl isomers such as propyl, isopropyl, etc.), $C_3H_6$ (e.g. cyclopropyl), $C_4H_9$ (e.g. butyl isomers) $C_4H_8$ (e.g. cyclobutyl isomers such as cyclobutyl, methylcyclopropyl, etc.), $C_5H_{11}$ (e.g. pentyl isomers), $C_5H_{10}$ (e.g. cyclopentyl isomers such as cyclopentyl, methylcyclobutyl, dimethylcyclopropyl, etc.) $C_6H_{13}$ (e.g. hexyl isomers), $C_6H_{12}$ (e.g. cyclohexyl isomers), $C_7H_{15}$ (e.g. heptyl isomers), $C_7H_{15}$ (e.g. cycloheptyl isomers), $C_8H_{17}$ (e.g. octyl isomers), $C_8H_{16}$ (e.g. cyclooctyl isomers), $C_9H_{19}$ (e.g. nonyl isomers), $C_9H_{18}$ (e.g. cyclononyl isomers), $C_{10}H_{21}$ (e.g. decyl isomers), $C_{10}H_{20}$ (e.g. cyclodecyl isomers), $C_{11}H_{23}$ (e.g. undecyl isomers), $C_{11}H_{22}$ (e.g. cycloundecyl isomers), $C_{12}H_{25}$ (e.g. dodecyl isomers), $C_{12}H_{24}$ (e.g. cyclododecyl isomers), $C_{13}H_{27}$ (e.g. tridecyl isomers), $C_{13}H_{26}$ (e.g. cyclotridecyl isomers), and the like.

As used herein, the term "phenoxy" refers to —O-phenyl.

Generally, an expression such as "$C_{6-10}$" (e.g. "a $C_{6-10}$ aromatic group") refers only to the number of carbon atoms in a parent group, and does not characterize or limit the substituents in any way. However, for alkyl (e.g. "$C_{1-12}$ alkyl"), all carbon atoms are counted which are directly bonded and which have no double or triple bonds. For example, the carbon atoms which are counted are numbered in the moieties below:

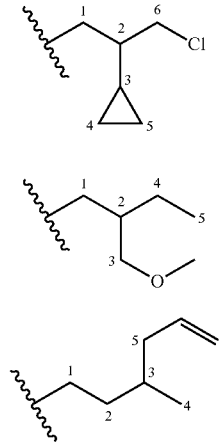

As used herein, the term "vinyldialkylsiloxy pendant group" has the ordinary meaning understood by a person of ordinary skill in the art. In some embodiments, the term "vinyldialkylsiloxy pendant group" may refer to a pendant group, e.g. a group which hangs from the polymer backbone rather than being part of it, which comprises a vinyldialkylsiloxy moiety, such as an —O—SiR'R''-vinyl moiety, wherein R' and R'' are independently alkyl. While not intending to be limiting, one useful example of a vinyldialkylsiloxy pendant group is a pendant group which comprises a vinyldimethylsiloxy moiety.

As used herein, the term "silicon-carbon covalent bond" has the ordinary meaning understood by a person of ordinary skill in the art. In some embodiments, the term "silicon-carbon covalent bond" may refer to a bond formed by a hydrosilation reaction that is the reaction between carbon-carbon double bond and an H—Si moiety, wherein the H—Si adds across the double bond such that a —Si—C—C—H unit is formed. Thus, in some embodiments, a silicon atom from an H—Si of a silicone component may form a covalent bond to a carbon atom from a C=C unit of a Si-vinyl group of an acrylic component, resulting in a Si—C covalent bond between the silicone component and the acrylic component.

I. Copolymeric Materials

Any component of any lens system described herein may comprise a copolymer or a copolymeric composite material disclosed herein With respect to a copolymer or an acrylic component of a copolymer composite material, in some embodiments, an acrylate recurring unit may be represented by Formula 1 or Formula 1a:

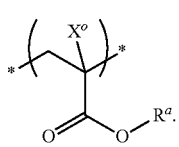

(Formula 1)

In some embodiments, an acrylate recurring unit, such as an acrylate recurring unit of Formula 1, may be derived from monomer 1:

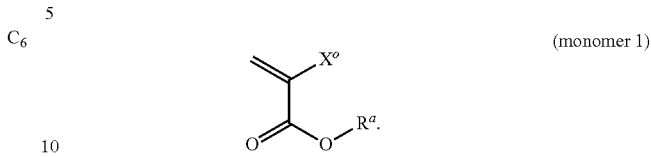

(monomer 1)

With respect to Formula 1 and monomer 1, $X^o$ may be H; or $C_{1-4}$ alkyl, such as methyl, ethyl, n-propyl, isopropyl, cyclopropyl, n-butyl, sec-butyl, t-butyl, cyclobutyl, methylcyclopropyl, and the like. In some embodiments, $X^o$ may be H, methyl or ethyl.

With respect to Formula 1 and monomer 1, $R^a$ may be optionally substituted $C_{1-12}$ alkyl, such as methyl, ethyl, propyl isomers, cyclopropyl, butyl isomers, cyclobutyl isomers (such as cyclobutyl, methylcyclopropyl, etc.), pentyl isomers, cyclopentyl isomers, hexyl isomers, cyclohexyl isomers, heptyl isomers, cycloheptyl isomers; octyl isomers, cyclooctyl isomers, nonyl isomers, cyclononyl isomers, decyl isomers, cyclodecyl isomers, or the like. In some embodiments, the alkyl may have 0, 1, 2, or 3 substituents, which may independently be selected from: $C_{1-4}$ alkoxy, such as methoxy; ethoxy; propoxy isomers (e.g. isopropoxy, n-propoxy, etc.), cyclopropoxy, butoxy isomers, cyclobutoxy isomers such as cyclobutoxy, methylcyclobutoxy, etc.; $C_{1-4}$ acyl such as formyl, acetyl, propionoyl, butyryl, isobutyryl, cyclopropanecarbonyl, etc.; $C_{1-4}$ acyloxy such as formyloxy (e.g. —OC(O)H), acetyloxy, propionoyloxy butyryloxy, isobutyryloxy, cyclopropanecarbonyloxy, etc.; $C_{2-4}$ alkyl carboxylate such as methyl carboxylate (e.g. $CO_2CH_3$), ethyl carboxylate, propyl carboxylate, isopropyl carboxylate, cyclopropyl carboxylate, etc; and the like With respect to Formula 1 and monomer 1, $R^a$ may also be -$Ph^a$ or —O-$Ph^a$, wherein $Ph^a$ is optionally substituted phenyl. In some embodiments, $Ph^a$ may have 0, 1, 2, 3, or 4 substituents independently selected from: $C_{1-6}$ alkyl, such as methyl, ethyl, propyl isomers, cyclopropyl, butyl isomers, cyclobutyl isomers (such as cyclobutyl, methylcyclopropyl, etc.), pentyl isomers, cyclopentyl isomers, hexyl isomers, cyclohexyl isomers, etc.; $C_{1-6}$ alkoxy, such as methoxy, ethoxy, propoxy isomers (e.g. isopropoxy, n-propoxy, etc.), cyclopropoxy, butoxy isomers, cyclobutoxy isomers (such as cyclobutoxy, methylcyclobutoxy, etc.), pentoxy isomers, cyclopentoxy isomers, hexoxy isomers, cyclohexoxy isomers, etc.; $C_{1-6}$ acyl such as formyl, acetyl, propionoyl butyryl, isobutyryl, cyclopropanecarbonyl, pentanoyl isomers (such as pentanoyl, methylbutanoyl, pivaloyl, etc.), cyclobutanecarbonyl isomers (such as methylcyclopropane carbonyl, cyclobutanecarbonyl, etc.), hexanoyl isomers, cyclopentanecarbonyl isomers, etc.; $C_{1-6}$ acyloxy such as —OC(O)H, acetyloxy, propionoyloxy, butyryloxy, isobutyryloxy, cyclopropanecarbonyloxy, pentanoyloxy isomers (such as pentanoyloxy, methylbutanoyloxy, pivaloyloxy, etc.), cyclobutanecarbonyloxy isomers (such as methylcyclopropanecarbonyloxy, cyclobutanecarbonyloxy, etc.), hexanoyloxy isomers, cyclopentanecarbonyloxy isomers, etc.; $C_{2-6}$ alkyl carboxylate such as methyl carboxylate (e.g. $CO_2CH_3$), ethyl carboxylate, propyl carboxylate, isopropyl carboxylate, cyclopropyl carboxylate, butyl carboxylate isomers (such as butyl carboxylate, isobutyl carboxylate, etc.), cyclobutyl carboxylate isomers (such as cyclobutyl carboxylate, methylcyclopropyl carboxylate, etc.), pentyl carboxylate isomers, cyclopentyl carboxylate isomers, etc.; and the like.

With respect to Formula 1 and monomer 1, $R^a$ may also be $-R^b\text{-Ph}^a$, wherein $R^b$ is optionally substituted $C_{1-4}$ alkyl and $Ph^a$ is optionally substituted phenyl as described above, such as optionally substituted $-CH_2$-phenyl, optionally substituted $-CH_2CH_2$-phenyl or an isomer thereof (such as $-CH(CH_3)$-phenyl), optionally substituted $-CH_2CH_2CH_2$-phenyl or an isomer thereof, optionally substituted $-CH_2CH_2CH_2CH_2$-phenyl or an isomer thereof, etc.; or $R^3$ may be $-R^b-O\text{-Ph}^a$, wherein $R^b$ is optionally substituted $C_{1-4}$ alkyl as described above and $Ph^a$ is optionally substituted phenyl as described above, such as optionally substituted $-CH_2-O$-phenyl, optionally substituted $-CH_2CH_2-O$-phenyl or an isomer thereof (such as $-CH(CH_3)-O$-phenyl), optionally substituted $-CH_2CH_2CH_2-O$-phenyl or an isomer thereof, optionally substituted $-CH_2CH_2CH_2CH_2-O$-phenyl or an isomer thereof, etc.

In some embodiments, $R^b$ may have 0, 1, 2, or 3 substituents, which may independently be selected from: $C_{1-4}$ alkoxy, such as methoxy, ethoxy, propoxy isomers (e.g. isopropoxy, n-propoxy, etc.), cyclopropoxy, butoxy isomers, cyclobutoxy isomers such as cyclobutoxy, methylcyclobutoxy, etc.; $C_{1-4}$ acyl such as formyl, acetyl, propionoyl, butyryl, isobutyryl, cyclopropanecarbonyl, and the like.

In some embodiments, monomer 1 may be: methyl methacrylate; ethyl acrylate; ethyl methacrylate; n-propyl acrylate; n-propyl methacrylate; iso-propyl acrylate; isopropyl methacrylate; n-butyl acrylate; n-butyl methacrylate; isobutyl acrylate; isobutyl methacrylate; n-pentyl acrylate; n-pentyl methacrylate; isopentyl acrylate; isopentyl methacrylate; n-hexyl acrylate; n-hexyl methacrylate; isohexyl acrylate; isohexyl methacrylate; n-heptyl acrylate; n-heptyl methacrylate; isoheptyl acrylate; isoheptyl methacrylate; n-octyl acrylate; n-octyl methacrylate; isooctyl acrylate; isooctyl methacrylate; phenoxyethyl acrylate; phenoxyethyl methacrylate; phenylethyl acrylate; phenylethyl methacrylate; phenoxypropyl acrylate; phenoxypropyl methacrylate; phenylpropyl acrylate; phenylpropyl methacrylate; phenylbutyl acrylate; phenylbutyl methacrylate; and the like.

The relative amounts of the recurring units in the copolymer may vary. In some embodiments, the recurring unit of Formula 1 may be about 20% to about 90%, about 40% to about 90%, about 30% to about 70%, or about 50% to about 70% of the mass of the copolymer. In some embodiments, there may be more than one kind of recurring unit of Formula 1. For example, the recurring units of Formula 1a and Formula 2 below are specific types of recurring units according to Formula 1, and some embodiments may include both kinds of recurring units. The amounts listed above are preferably the total of the recurring units of Formula 1, with each type being present at the amounts discussed above or at a lower amount, including about 15% to about 25%.

In some embodiments, monomer 1 may represent about 20% to about 90%, about 40% to about 90%, about 30% to about 70%, or about 50% to about 70% of the total weight of all monomers used to prepare the copolymer. In some embodiments, there may be more than one kind of monomer of monomer 1. For example, monomer 1a and monomer 2 below are specific types of the monomer 1, and some embodiments may include both kinds of monomers. The amounts listed above are preferably the total of the monomers of monomer 1, with each type being present at the amounts discussed above or at a lower amount, including about 15% to about 25%.

In some embodiments, an acrylate recurring unit may be represented by Formula Formula 1a:

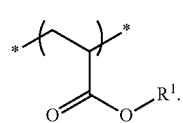

(Formula 1a)

In some embodiments, an acrylate recurring unit, such as an acrylate recurring unit of Formula 1a, may be derived from monomer 1a:

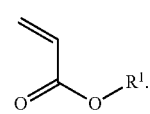

(monomer 1a)

For example, in some embodiments, monomer 1a may be reacted in the presence of at least one other monomer from which the acrylate recurring unit or the optionally substituted vinylaryl recurring unit may be derived.

With respect to Formula 1a and monomer 1a, $R^1$ may be $C_{1-12}$ alkyl such as methyl, ethyl, propyl isomers, cyclopropyl, butyl isomers, cyclobutyl isomers (such as cyclobutyl, methylcyclopropyl, etc.), pentyl isomers, cyclopentyl isomers, hexyl isomers, cyclohexyl isomers, heptyl isomers, cycloheptyl isomers; octyl isomers, cyclooctyl isomers, nonyl isomers, cyclononyl isomers, decyl isomers, cyclodecyl isomers, or the like; or optionally substituted phenyl. In some embodiments, $R^1$ may be $C_{1-6}$ alkyl. In some embodiments, $R^1$ may be n-butyl.

In some embodiments, monomer 1a may be n-butyl acrylate. ethyl acrylate, n-propyl acrylate, iso-propyl acrylate, n-butyl acrylate, isobutyl acrylate, n-pentyl acrylate, isopentyl acrylate, n-hexyl acrylate, isohexyl acrylate, n-heptyl acrylate, isoheptyl acrylate, n-octyl acrylate, isooctyl acrylate, or the like. In some embodiments, monomer 1a may be ethyl acrylate, n-propyl acrylate, n-butyl acrylate, or n-hexyl acrylate.

The relative amounts of the recurring units in the copolymer may vary. In some embodiments, the recurring unit of Formula 1a may be about 20% to about 90%, about 40% to about 90%, about 20% to about 70%, about 30% to about 70%, about 50% to about 70%, about 40% to about 55%, or about 15% to about 25% of the mass of the copolymer.

In some embodiments, monomer 1a may represent about 20% to about 90%, about 40% to about 90%, about 20% to about 70%, about 30% to about 70%, about 50% to about 70%, about 40% to about 55%, or about 15% to about 25% of the total weight of all monomers used to prepare the copolymer.

In some embodiments, an acrylate recurring unit may be represented by Formula 2:

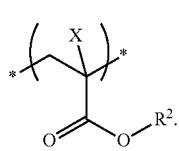

(Formula 2)

In some embodiments, an acrylate recurring unit, such as an acrylate recurring unit of Formula 2, may be derived from monomer 2:

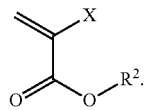

(monomer 2)

With respect to Formula 2 and monomer 2, $R^2$ may be $C_{1-12}$ alkyl such as methyl, ethyl, propyl isomers, cyclopropyl, butyl isomers, cyclobutyl isomers (such as cyclobutyl, methylcyclopropyl, etc.), pentyl isomers, cyclopentyl isomers, hexyl isomers, cyclohexyl isomers, heptyl isomers, cycloheptyl isomers; octyl isomers, cyclooctyl isomers, nonyl isomers, cyclononyl isomers, decyl isomers, cyclodecyl isomers, or the like; or optionally substituted phenyl. In some embodiments $R^2$ may be $C_{1-4}$ alkyl. In some embodiments $R^2$ may be ethyl.

With respect to Formula 2 and monomer 2, X may be $C_{1-4}$ alkyl such as methyl, ethyl, n-propyl, isopropyl, cyclopropyl, n-butyl, sec-butyl, t-butyl, cyclobutyl, methylcyclopropyl, and the like. In some embodiments, X may be methyl or ethyl.

In some embodiments, monomer 2 may be methyl methacrylate, ethyl methacrylate, n-propyl methacrylate, isopropyl methacrylate, n-butyl methacrylate, isobutyl methacrylate, n-pentyl methacrylate, isopentyl methacrylate, n-hexyl methacrylate, isohexyl methacrylate, n-heptyl methacrylate, isoheptyl methacrylate, n-octyl methacrylate, isooctyl methacrylate, or the like. In some embodiments, monomer 2 may be ethyl methacrylate, n-butyl methacrylate, n-propyl methacrylate, or n-hexyl methacrylate. In some embodiments, monomer 2 may be ethyl methacrylate.

The relative amounts of the recurring units in the copolymer may vary. In some embodiments, the recurring unit of Formula 2 may be about 5% to about 60%, about 20% to about 50%, about 25% to about 45%, or about 15% to about 25% of the mass of the copolymer.

In some embodiments, monomer 2 may represent about 5% to about 60%, about 10% to about 40%, about 20% to about 50%, about 25% to about 45%, or about 15% to about 25% of the total weight of all monomers used to prepare the copolymer.

In some embodiments, the copolymer comprises an acrylate repeating unit represented by Formula 1a and an acrylate repeating unit represented by Formula 2.

In some embodiments, an optionally substituted vinylaryl recurring unit may be represented by Formula 3 or Formula 3a:

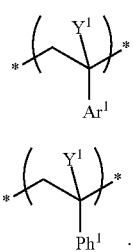

(Formula 3)

(Formula 3a)

In some embodiments, an optionally substituted vinylaryl recurring unit, such as an optionally substituted vinylaryl recurring unit of Formula 3 or Formula 3a, may be derived from monomer 3, or (in the case of Formula 3a) monomer 3a:

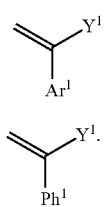

(monomer 3)

(monomer 3a)

With respect to Formula 3, Formula 3a, monomer 3, and monomer 3a, $Y^1$ may be H, or $C_{1-4}$ alkyl such as methyl, ethyl, n-propyl, isopropyl, cyclopropyl, n-butyl, sec-butyl, t-butyl, cyclobutyl, methylcyclopropyl, and the like. In some embodiments, $Y^1$ may be hydrogen or methyl.

With respect to Formula 3 and monomer 3, $Ar^1$ may be an optionally substituted aromatic group, including an optionally substituted $C_{6-10}$ aromatic group, such as optionally substituted phenyl or optionally substituted naphthyl; or $Ar^1$ may be an optionally substituted heteroaromatic group, including a $C_{3-9}$ heteroaromatic group, such as optionally substituted pyridinyl, optionally substituted furyl, optionally substituted thienyl, optionally substituted oxazolyl, optionally substituted thiazolyl, optionally substituted imidazolyl, optionally substituted quinolinyl, etc.

With respect to Formula 3a and monomer 3a, $Ph^1$ may be optionally substituted phenyl.

In some embodiments related to Formula 3, Formula 3a, monomer 3, and monomer 3a, the aromatic group, the heteroaromatic group, or phenyl may have 0, 1, 2, 3, or 4 substituents independently selected from: $C_{1-6}$ alkyl, such as methyl, ethyl, propyl isomers, cyclopropyl, butyl isomers, cyclobutyl isomers (such as cyclobutyl, methylcyclopropyl, etc.), pentyl isomers, cyclopentyl isomers, hexyl isomers, cyclohexyl isomers, etc.; $C_{1-6}$ alkoxy, such as methoxy, ethoxy, propoxy isomers (e.g. isopropoxy, n-propoxy, etc.), cyclopropoxy, butoxy isomers, cyclobutoxy isomers (such as cyclobutoxy, methylcyclobutoxy, etc.), pentoxy isomers, cyclopentoxy isomers, hexoxy isomers, cyclohexoxy isomers, etc.; $C_{1-6}$ acyl such as formyl, acetyl, propionoyl butyryl, isobutyryl, cyclopropanecarbonyl, pentanoyl isomers (such as pentanoyl, methylbutanoyl, pivaloyl, etc.), cyclobutanecarbonyl isomers (such as methylcyclopropane carbonyl, cyclobutanecarbonyl, etc.), hexanoyl isomers, cyclopentanecarbonyl isomers, etc.; $C_{1-6}$ acyloxy such as formyloxy (e.g. —OC(O)H), acetyloxy, propionoyloxy butyryloxy, isobutyryloxy, cyclopropanecarbonyloxy, pentanoyloxy isomers (such as pentanoyloxy, methylbutanoyloxy, pivaloyloxy, etc.), cyclobutanecarbonyloxy isomers (such as methylcyclopropanecarbonyloxy, cyclobutanecarbonyloxy, etc.), hexanoyloxy isomers, cyclopentanecarbonyloxy isomers, etc.; $C_{2-4}$ alkyl carboxylate such as methyl carboxylate (e.g. $CO_2CH_3$), ethyl carboxylate, propyl carboxylate, isopropyl carboxylate, cyclopropyl carboxylate, butyl carboxylate isomers (such as butyl carboxylate, isobutyl carboxylate, etc.), cyclobutyl carboxylate isomers (such as cyclobutyl carboxylate, methylcyclopropyl carboxylate, etc.), pentyl carboxylate isomers, cyclopentyl carboxylate isomers, etc.; and the like.

In some embodiments, monomer 3 or monomer 3a may be styrene; methylstyrene; chlorostyrene; bromostyrene; methoxylstyrene; N,N-dimethylaminostyrene; etc. In some embodiments, monomer 3 or monomer 3a may be alkylstyrene (such as methylstyrene, ethylstyrene, n-propylstyrene, isopropylstyrene, or the like) or dialkylstyrene (such as dimethylstyrene, methylethylstyrene, methylisopropyl styrene, etc.). In some embodiments, monomer 3 or monomer 3a may be methylstyrene.

In some embodiments, an vinylaryl recurring unit may be derived from allyl benzene.

The relative amounts of the recurring units in the copolymer may vary. In some embodiments, the relative amount of the recurring unit of Formula 3 may be varied to modulate refractive index. In some embodiments, increasing the relative amount of Formula 3 may increase the refractive index of the copolymer. In some embodiments, the recurring unit of Formula 3 may be about 10% to about 30%, including about 15% to about 20% of the mass of the copolymer.

In some embodiments, monomer 3 or monomer 3a may represent about 5% to about 40%, about 10% to about 30%, or about 15% to about 20% of the total weight of all monomers used to prepare the copolymer.

At least a portion of at least one of the acrylate or vinylaryl recurring units comprises a vinyldialkylsiloxy pendant group. For example, if an acrylate recurring unit comprises a vinyldialkylsiloxy pendant group, it may be represented by Formula 4:

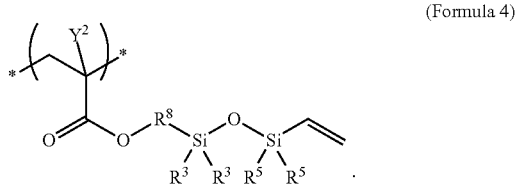

(Formula 4)

In some embodiments, an acrylate recurring unit comprising a vinyldialkylsiloxy pendant group, such as a recurring unit of Formula 4, may be derived from monomer 4:

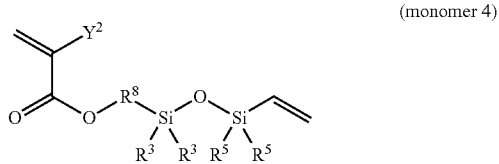

(monomer 4)

With respect to Formula 4 and monomer 4, $Y^2$ is H, or $C_{1-4}$ alkyl such as methyl, ethyl, n-propyl, isopropyl, cyclopropyl, n-butyl, sec-butyl, t-butyl, cyclobutyl, methylcyclopropyl, and the like. In some embodiments, $Y^2$ may be hydrogen or methyl.

With respect to Formula 4 and monomer 4, each $R^3$ is independently $C_{1-4}$ alkyl such as methyl, ethyl, n-propyl, isopropyl, cyclopropyl, n-butyl, sec-butyl, t-butyl, cyclobutyl, methylcyclopropyl, and the like; or

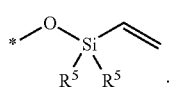

In some embodiments each $R^3$ may independently be vinyldimethylsiloxy or methyl.

With respect to Formula 4 and monomer 4, each $R^5$ is independently $C_{1-4}$ alkyl such as methyl, ethyl, n-propyl, isopropyl, cyclopropyl, n-butyl, sec-butyl, t-butyl, cyclobutyl, methylcyclopropyl, and the like. In some embodiments, each $R^5$ may be methyl or ethyl.

With respect to Formula 4 and monomer 4, $R^8$ is $C_{1-6}$ alkyl, such as $-(CH_2)_n-$ wherein n is 1, 2, 3, 4, 5, or 6, or a branched or cyclic isomers of a $-(CH_2)_n-$ (e.g. $-CH(CH_3)-$, -cyclopentyl-, $-CH(CH_3)CH_2-$, etc). In some embodiments, $R^8$ may be $-(CH_2)_3-$ or $-(CH_2)_4-$.

In some embodiments, monomer 4 may be:
methacryloxypropyltris(vinyldimethylsiloxy)silane,
methacryloxypropyldi(vinyldimethylsiloxy)methylsilane,
methacryloxypropyl(vinyldimethylsiloxy)dimethylsilane,
acryloxypropyltris(vinyldimethylsiloxy)silane,
methacryloxybutyltris(vinyldimethylsiloxy)silane,
acryloxybutyltris(vinyldimethylsiloxy)silane,
acryloxypropyldi(vinyldimethylsiloxy)methylsilane,
methacryloxybutyldi(vinyldimethylsiloxy)methyl silane,
acryloxybutyldi(vinyldimethylsiloxy)methylsilane,
acryloxypropyl(vinyldimethylsiloxy)dimethylsilane,
methacryloxybutyl(vinyldimethylsiloxy)dimethylsilane,
acryloxybutyl(vinyldimethylsiloxy)dimethylsilane, or the like.

The relative amounts of the recurring units in the copolymer may vary. In some embodiments, the relative amount of the recurring unit of Formula 4 may be increased to improve bonding of the copolymer to a silicone by increasing the number of silicon-carbon covalent bonds between the copolymer and the silicone formed by the hydrosilation reaction. In some embodiments, the recurring unit of Formula 4 may be about 1% to about 20%, about 5% to about 15%, or about 8% to about 12%, of the mass of the copolymer.

In some embodiments, monomer 4 may represent about 1% to about 20%, about 5% to about 15%, or about 8% to about 12% of the total weight of all monomers used to prepare the copolymer.

If an optionally substituted vinylaryl recurring unit comprises a vinyldialkylsiloxy pendant group, it may be represented by Formula 5 or Formula 5a:

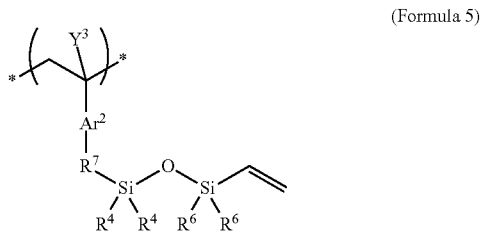

(Formula 5)

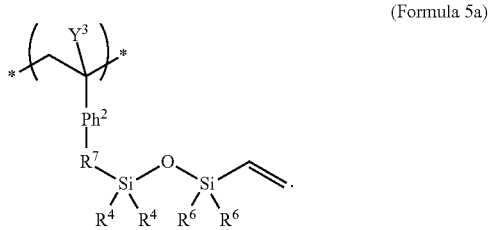

(Formula 5a)

In some embodiments, an optionally substituted vinylaryl recurring unit comprising a vinyldialkylsiloxy pendant group, such as optionally substituted vinylaryl recurring unit of Formula 5 or Formula 5a, may be derived from monomer 5, or (in the case of Formula 5a) monomer 5a:

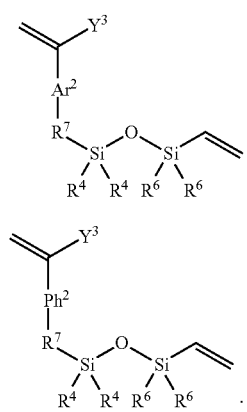

(monomer 5)

(monomer 5a)

With respect to Formula 5, Formula 5a, monomer 5, and monomer 5a, $Y^3$ is H, or $C_{1-4}$ alkyl such as methyl, ethyl, n-propyl, isopropyl, cyclopropyl, n-butyl, sec-butyl, t-butyl, cyclobutyl, methylcyclopropyl, and the like. In some embodiments, $Y^3$ may be hydrogen or methyl.

With respect to Formula 5 and monomer 5, $Ar^2$ may be an optionally substituted aromatic group, including a $C_{6-10}$ aromatic group, such as optionally substituted phenyl or optionally substituted naphthyl; or $Ar^1$ may be optionally substituted aromatic group, including a $C_{3-9}$ heteroaromatic group, such as optionally substituted pyridinyl, optionally substituted furyl, optionally substituted thienyl, optionally substituted oxazolyl, optionally substituted thiazolyl, optionally substituted imidazolyl, optionally substituted quinolinyl, etc.

With respect to Formula 5a and monomer 5a, $Ph^2$ may be optionally substituted phenyl.

In some embodiments related to Formula 5, Formula 5a, monomer 5, and monomer 5a, the aromatic group, heteroaromatic group, or phenyl may have 0, 1, 2, 3, or 4 substituents independently selected from: $C_{1-6}$ alkyl, such as methyl, ethyl, propyl isomers, cyclopropyl, butyl isomers, cyclobutyl isomers (such as cyclobutyl, methylcyclopropyl, etc.), pentyl isomers, cyclopentyl isomers, hexyl isomers, cyclohexyl isomers, etc.; $C_{1-6}$ alkoxy, such as methoxy, ethoxy, propoxy isomers (e.g. isopropoxy, n-propoxy, etc.), cyclopropoxy, butoxy isomers, cyclobutoxy isomers (such as cyclobutoxy, methylcyclobutoxy, etc.), pentoxy isomers, cyclopentoxy isomers, hexoxy isomers, cyclohexoxy isomers, etc.; $C_{1-6}$ acyl such as formyl, acetyl, propionoyl butyryl, isobutyryl, cyclopropanecarbonyl, pentanoyl isomers (such as pentanoyl, methylbutanoyl, pivaloyl, etc.), cyclobutanecarbonyl isomers (such as methylcyclopropane carbonyl, cyclobutanecarbonyl, etc.), hexanoyl isomers, cyclopentanecarbonyl isomers, etc.; $C_{1-6}$ acyloxy such as formyloxy (e.g. —OC(O)H), acetyloxy, propionoyloxy butyryloxy, isobutyryloxy, cyclopropanecarbonyloxy, pentanoyloxy isomers (such as pentanoyloxy, methylbutanoyloxy, pivaloyloxy, etc.), cyclobutanecarbonyloxy isomers (such as methylcyclopropanecarbonyloxy, cyclobutanecarbonyloxy, etc.), hexanoyloxy isomers, cyclopentanecarbonyloxy isomers, etc.; $C_{2-6}$ alkyl carboxylate such as methyl carboxylate (e.g. $CO_2CH_3$), ethyl carboxylate, propyl carboxylate, isopropyl carboxylate, cyclopropyl carboxylate, butyl carboxylate isomers (such as butyl carboxylate, isobutyl carboxylate, etc.), cyclobutyl carboxylate isomers (such as cyclobutyl carboxylate, methylcyclopropyl carboxylate, etc.), pentyl carboxylate isomers, cyclopentyl carboxylate isomers, etc.; and the like.

With respect to Formula 5, Formula 5a, monomer 5, and monomer 5a, $R^4$ is independently $C_{1-4}$ alkyl such as methyl, ethyl, n-propyl, isopropyl, cyclopropyl, n-butyl, sec-butyl, t-butyl, cyclobutyl, methylcyclopropyl, and the like; or

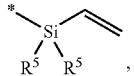

wherein $R^5$ is the same as that described with respect to Formula 4 and monomer 4. In some embodiments each $R^4$ may independently be vinyldimethylsiloxy or methyl;

With respect to Formula 5, Formula 5a, monomer 5, and monomer 5a, each $R^6$ is independently $C_{1-4}$ alkyl such as methyl, ethyl, n-propyl, isopropyl, cyclopropyl, n-butyl, sec-butyl, t-butyl, cyclobutyl, methylcyclopropyl, and the like. In some embodiments, each $R^6$ may be methyl or ethyl.

With respect to Formula 5, Formula 5a, monomer 5, and monomer 5a, $R^7$ is a covalent bond (e.g. a covalent bond connecting the O atom directly to the Si atom) or $C_{1-6}$ alkyl, such as —$(CH_2)_n$— wherein n is 1, 2, 3, 4, 5, or 6, or a branched or cyclic isomers of a —$(CH_2)_n$— (e.g. —CH(CH$_3$)—, -cyclopentyl-, —CH(CH$_3$)CH$_2$—, etc). In some embodiments, $R^7$ may be a covalent bond, —CH$_2$—, —CH$_2$CH$_2$—, or —CH$_2$CH$_2$CH$_2$—.

In some embodiments, monomer 5 or monomer 5a may be:
styrylmethyltris(vinyldimethylsiloxy)silane,
styrylethyltris(vinyldimethylsiloxy)silane, styrlmethyldi(vinyldimethylsiloxy)methylsilane,
styrylethyldi(vinyldimethylsiloxy)methylsilane,
styrlmethyl(vinyldimethylsiloxy)dimethylsilane,
styrylethyl(vinyldimethylsiloxy)dimethylsilane, or the like The relative amounts of the recurring units in the copolymer may vary. In some embodiments, the relative amount of the recurring unit of Formula 5 or Formula 5a may be increased to improve bonding of the copolymer to a silicone by increasing the number of silicon-carbon covalent bonds formed by the hydrosilation reaction between the copolymer and the silicone. In some embodiments, the recurring unit of Formula 4 may be about 1% to about 20%, about 5% to about 15%, or about 8% to about 12% of the mass of the copolymer.

In some embodiments, monomer 5 or monomer 5a may represent about 1% to about 20%, about 5% to about 15%, or about 8% to about 12% of the total weight of all monomers used to prepare the copolymer.

In some embodiments, the copolymer comprises about 20% to about 90%, about 40% to about 90%, about 30% to about 70%, or about 50% to about 70% recurring units of Formula 1; about 10% to about 30%, including about 15% to about 20% recurring units of Formula 3; and about 1% to about 20%, about 5% to about 15%, or about 8 to about 12% recurring units of Formula 4 or Formula 5; based upon the weight of the copolymer, or alternatively, based upon the molar percentages of each repeating unit.

Some embodiments are related to copolymers comprising the following recurring units: a) a recurring unit of Formula 1 or Formula 1a, b) a recurring unit of Formula 2, c) a recurring unit of Formula 3 or Formula 3a, and d) a recurring unit of Formula 4. In some embodiments, these copolymers may be prepared by a process comprising reacting: a) monomer 1 or monomer 1a, b) monomer 2, c) monomer 3 or monomer 3a, and d) monomer 4. In these embodiments, these monomers may be reacted in any combination or order, and may be reacted with another monomer of the same type (e.g. monomer 1a reacting with monomer 1a), provided that there is at least one molecule of the copolymer which comprises at least one recurring unit derived from at least one of each of: a) monomer 1 or monomer 1a, b) monomer 2, c) monomer 3 or monomer 3a, and d) monomer 4.

Some embodiments are related to copolymers comprising the following recurring units: a) a recurring unit of Formula 1 or Formula 1a, b) a recurring unit of Formula 2, c) a recurring unit of Formula 3 or Formula 3a, and d) a recurring unit of Formula 5 or Formula 5a. In some embodiments, these copolymers may be prepared by a process comprising reacting: a) monomer 1 or monomer 1a, b) monomer 2, c) monomer 3 or monomer 3a, and d) monomer 5 or monomer 5a. In these embodiments, these monomers may be reacted in any combination or order, and may be reacted with another monomer of the same type (e.g. monomer 1a reacting with monomer 1a), provided that there is at least one molecule of the copolymer which comprises at least one recurring unit derived from at least one of each of: a) monomer 1 or monomer 1a, b) monomer 2, c) monomer 3 or monomer 3a, and d) monomer 5 or monomer 5a.

In some embodiments, $R^1$ is n-butyl, $R^2$ is ethyl, X is methyl or ethyl; $Y^1$, $Y^2$, and $Y^3$ are independently hydrogen or methyl; $Ph^1$ and $Ph^2$ are unsubstituted phenyl, each $R^3$ and each $R^4$ is independently vinyldimethylsiloxy or methyl; $R^5$ and $R^6$ are methyl; $R^7$ is a covalent bond, —$CH_2$—, —$CH_2CH_2$—, or —$CH_2CH_2CH_2$—; and $R^8$ is —$(CH_2)_3$— or —$(CH_2)_4$—.

In some embodiments, $R^1$ and $R^2$ are independently $C_{1-6}$ alkyl; X is methyl or ethyl; $Y^1$, $Y^2$, and $Y^3$ are independently hydrogen or methyl: $Ph^1$ and $Ph^2$ are unsubstituted phenyl, each $R^3$ and each $R^4$ is independently vinyldimethylsiloxy or methyl; each $R^5$ and each $R^6$ is independently methyl or ethyl; $R^7$ is a covalent bond, —$CH_2$—, $CH_2CH_2$—, or —$CH_2CH_2CH_2$—; and $R^8$ is —$(CH_2)_3$— or —$(CH_2)_4$—.

The copolymer may also comprise a recurring unit or an additive which may act as a UV absorber. In some embodiments, the UV absorber may be a recurring unit or an additive comprising a benzophenone derivative or a benzotriazole derivative. For example, in some embodiments, 2-[3-(2H-Benzotriazol-2-yl)-4-hydroxyphenyl]ethyl methacrylate may be added at any point during a process comprising reacting: a) monomer 1 or monomer 1a, b) monomer 2, c) monomer 3 or monomer 3a, and d) monomer 4; or may be added at any point during a process comprising reacting: a) monomer 1 or monomer 1a, b) monomer 2, c) monomer 3 or monomer 3a, and d) monomer 5 or monomer 5a.

The copolymer may also comprise a polymerizable yellow dye and/or a polymerizable photochromic yellow dye which may provide yellow color and/or photochromicity to the copolymer.

The reaction processes described herein for making acrylic copolymers may be anionic, cationic, or free radical polymerization processes. In free radical polymerization processes, the free radical initiating species may be a peroxide, an azo free radical initiators, or a UV free radical initiator such as Darocure and Irgocure. In some embodiments, 2,2'-azobisisobutyronitrile may be added as a free radical initiator at any point during a process comprising reacting: a) monomer 1 or monomer 1a, b) monomer 2, c) monomer 3 or monomer 3a, and d) monomer 4; or may be added at any point during a process comprising reacting: a) monomer 1 or monomer 1a, b) monomer 2, c) monomer 3 or monomer 3a, and d) monomer 5 or monomer 5a.

The copolymers may also comprise a crosslinker such as an ethylene glycol dimethacrylates; an ethylene glycol diacrylates; a 1,3-propylene glycol dimethacrylate; a 1,3-propylene glycol diacrylate; a 1,4-butylene glycol dimethacrylate; a 1,4-butylene glycol diacrylate; a 1,6-hexylene glycol dimethacrylate; a 1,6-hexylene glycol diacrylate; 1,4-divinylbenzene; or the like. In some embodiments, the crosslinkers may be an ethylene glycol dimethacrylate; an ethylene glycol diacrylate; a 1,4-butylene glycol dimethacrylate; or a 1,4-butylene glycol diacrylates. In some embodiments, the crosslinkers may be an ethylene glycol dimethacrylate or a 1,4-butylene glycol dimethacrylate.

In some embodiments, ethylene glycol dimethacrylate may be added as a crosslinker at any point during a process comprising reacting: a) monomer 1 or monomer 1a, b) monomer 2, c) monomer 3 or monomer 3a, and d) monomer 4; or may be added at any point during a process comprising reacting: a) monomer 1 or monomer 1a, b) monomer 2, c) monomer 3 or monomer 3a, and d) monomer 5 or monomer 5a.

In some embodiments, the copolymer is a reaction product of methylstyrene, ethyl methacrylate, n-butyl acrylate, ethylene glycol dimethacrylate, 2-[3-(2h-benzotriazol-2-yl)-4-hydroxyphenyl]ethyl methacrylate, methacryloxypropyltris(vinyldimethylsiloxy)silane, and 2,2'-azobisisobutyronitrile.

In these embodiments, the weight percents of each component may be as follows: about 15% to about 20% methylstyrene, about 15% to about 25% ethyl methacrylate, about 40% to about 60% n-butyl acrylate, about 2% to about 10% ethylene glycol dimethacrylate, about 0.5% to about 3% 2-[3-(2h-benzotriazol-2-yl)-4-hydroxyphenyl]ethyl methacrylate, about 2% to about 20% methacryloxypropyltris(vinyldimethylsiloxy)silane, and about 0.01% to about 5% 2,2'-azobisisobutyronitrile.

In some embodiments, these copolymers may be acrylic copolymers with a refractive index of about 1.46 to about 1.56, or about 1.48 to about 1.52.

In some embodiments, an acrylic copolymer described herein has a glass transition temperature lower than about 37° C. or lower than about 20° C.

In some embodiments, an acrylic copolymer described herein is optically clear.

An acrylic copolymer described above may be useful as an acrylic component of a copolymeric composite material comprising: an acrylic component, a silicone component, and a plurality of silicon-carbon covalent bonds that are formed by a hydrosilation reaction between a silicon atom of the silicone component and a carbon atom of the vinyldialkylsiloxy pendant group of the acrylic component.

The silicone component may be any silicone material. In some embodiments, the silicone component may have a refractive index from about 1.37 to about 1.50.

The copolymeric composite material comprises a plurality of silicon-carbon covalent bonds formed by a hydrosilation reaction between a silicon atom of the silicone component and a carbon atom of the vinyldialkylsiloxy pendant group of the acrylic component. For example, in some embodiments, the plurality of silicon-carbon covalent bonds comprises a covalent bond between $R^9$ and $Z^1$ or $R^{10}$ and $Z^2$ in a plurality of recurring units represented Formula 6 Formula 6a, or Formula 7:

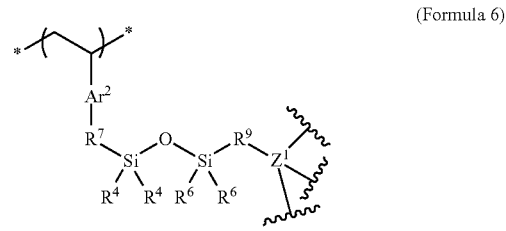

(Formula 6)

-continued (Formula 6a)

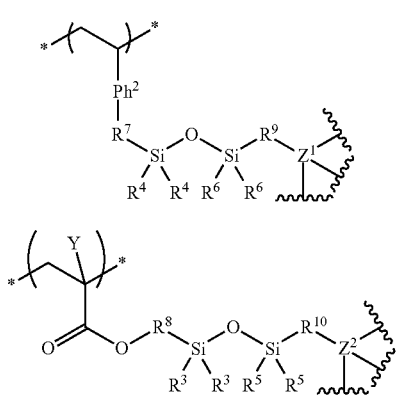

(Formula 7)

In these embodiments, $Ar^2$, $Ph^2$, Y, $R^5$, $R^6$, $R^7$, $R^8$ are the same as those described above with respect to Formula 4, monomer 4, Formula 5, monomer 5, or monomer 5a.

With respect to Formula 6 and Formula 7, $R^9$ and $R^{10}$ are $C_2H_4$, and $Z^1$ and $Z^2$ are an Si atom from an H—Si moiety of the silicone component wherein the H atom has been replaced with $R^9$ or $R^{10}$ in a hydrosilation reaction For example, in some embodiments, $R^9$—$Z^1$ and $R^{10}$—$Z^2$ are a product of a reaction between the vinyldialkylsiloxy groups of Formula 4, monomer 4, Formula 5, or monomer 5, or monomer 5a, and an H—Si moiety of a silicone, as shown in one of reactions a-d of Scheme 1.

Scheme 1

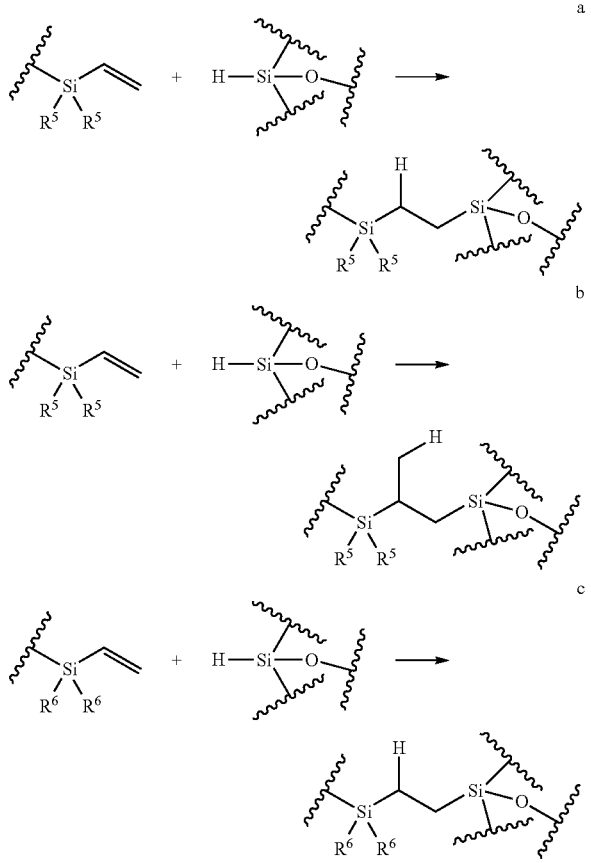

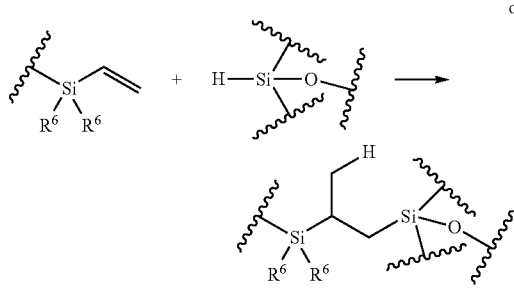

Thus, in some embodiments, $R^9$ or $R^{10}$ may be —$CH_2CH_2$—, or —$CH(CH_3)$—.

Some embodiments provide an intraocular lens comprising a copolymeric composite material described above. In some embodiments, the intraocular lens may be an accommodation intraocular lens system. In some embodiments, the intraocular lens may be an intraocular refractive lens.

In some embodiments, the intraocular lenses described herein can provide a higher refractive index, a thinner lens, and smaller incision than is currently available. In some embodiments, the intraocular lenses described herein can provide slower unfolding time than a full silicone lens (unfolding time in the eye within few seconds), which can significantly reduce the capsular bag damage. In some embodiments, the intraocular lenses described herein can provide a lower calcification and fiberousis than that which can result from a hydrophilic or a silicone lens. In some embodiments, the intraocular lenses described herein can result in a lower incidence of posterior capsule opacification ("PCO") than a hydrophilic lens or a silicone lens. In some embodiments, the intraocular lenses described herein can provide the optical advantages of an acrylic lens with silicone haptic flexibility.

In some embodiments, the intraocular lens further comprises: an anterior viewing element comprising an optic having refractive power of less than 55 diopters and a posterior viewing element; and are connected to a biasing structure which allows the optics to move relative to each other along the optical axis in response to a contractile force by the ciliary muscle of the eye upon the capsular bag of the eye. The relative movement corresponds to change in the combined power of the optics of at least one diopter. Alternatively, the accommodating intraocular lens can further comprise a posterior viewing element comprising an optic having a refractive power of zero to minus 25 diopters.

II. Additional Materials/Surface Treatments

In addition to the copolymeric materials disclosed herein, any intraocular lens system may comprise additional silicone, acrylics, polymethylmethacrylate (PMMA), block copolymers of styrene-ethylene-butylene-styrene (C-FLEX) or other styrene-base copolymers, polyvinyl alcohol (PVA), polyurethanes, hydrogels or any other suitable polymers or monomers. In addition, any portion of any intraocular lens system other than the optic(s) may be formed from stainless steel or a shape-memory alloy such as nitinol or any iron-based shape-memory alloy. Metallic components may be coated with gold to increase biocompatibility. Where feasible, material of a lower Shore A hardness may be used for the optic(s), and material of higher hardness may be used for the balance of any intraocular lens system. Finally, the optic(s) may be formed from a photosensitive silicone to facilitate post-implantation power adjustment as taught in U.S. Pat. No. 6,450,642, the entire contents of which are hereby incorporated by reference herein.

The optics and/or the balance of any intraocular lens system can also be formed from layers of differing materials. The layers may be arranged in a simple sandwich fashion, or concentrically. In addition, the layers may include a series of polymer layers, a mix of polymer and metallic layers, or a mix of polymer and monomer layers. In particular, a nitinol ribbon core with a surrounding silicone jacket may be used for any portion of a lens system except for the optics; an acrylic-over-silicone laminate, including acrylic-over silicone laminates comprising the copolymeric materials disclosed herein, may be employed for the optics. In addition to employing covalent bonds such as silicon-carbon covalent bonds formed by a hydrosilation reaction, a layered construction may be obtained by pressing/bonding two or more layers together, or deposition or coating processes.

Where desired, the anterior optic may be formed from a material different from that used to form the posterior optic. This may be done to take advantage of differences between the respective materials in refractive index, mechanical properties or resistance to PCO, or to achieve an appropriate balance of mechanical and optical properties. Additionally, the use of differing materials can increase resistance to intralenticular opacification ("ILO"). For example, the material forming the posterior optic may be selected for its resistance to PCO, and/or for its rigidity (so as to form a relatively rigid base for the biasing action of the biasing structure, thereby maximizing the range of spacing between the anterior viewing element and the posterior viewing element). Thus, the posterior optic may be formed from acrylic; for example, a hydrophobic acrylic such as a copolymer described herein. The material forming the anterior optic may be selected for its high index of refraction, to keep to a minimum the size and weight of the anterior optic (and the lens system as a whole), thereby maximizing the range and speed of motion of the anterior optic in response to a given biasing force. To achieve these properties the anterior optic may be formed from silicone; for example, high-refractive-index silicones (generally, silicones with a refractive index greater than about 1.43, or silicones with a refractive index of about 1.46).

In other embodiments, the anterior optic may be formed from any suitable material (including those disclosed herein), and the posterior optic may be formed from any suitable material (including those disclosed herein) other than the material chosen to form the anterior optic. In one embodiment the anterior optic is formed from silicone and the posterior optic is formed from acrylic such as a copolymer described herein; in another embodiment the anterior optic is formed from acrylic, such as a copolymer described herein, and the posterior optic is formed from silicone.

In one embodiment, portions of any intraocular lens system other than the optic(s) are formed from a shape-memory alloy. This embodiment takes advantage of the exceptional mechanical properties of shape-memory alloys and provides fast, consistent, highly responsive movement of the optic(s) within the capsular bag while minimizing material fatigue in any intraocular lens system. In one embodiment, from the biasing structure may comprise a shape-memory alloy such as nitinol or any iron-based shape-memory alloy. Due to the flat stress-strain curve of nitinol, such biasing elements provide a highly consistent accommodation force over a wide range of displacement. Furthermore, biasing elements formed from a shape-memory alloy, especially nitinol, retain their spring properties when exposed to heat (as occurs upon implantation into a human eye) while polymeric biasing elements tend to lose their spring properties, thus detracting from the responsiveness of the lens system. For similar reasons, it is advantageous to use shape-memory alloys such as those discussed above in forming any portion of a conventional (non-accommodating) intraocular lens, other than the optic.

Where desired, various coatings are suitable for components of any intraocular lens system. A heparin coating may be applied to appropriate locations on any intraocular lens system to prevent inflammatory cell attachment (ICA) and/or posterior capsule opacification (PCO); naturally, possible locations for such a coating include the biasing structure. Coatings can also be applied to any intraocular lens system to improve biocompatibility; such coatings include "active" coatings like P-15 peptides or RGD peptides, and "passive" coatings such as heparin and other mucopolysaccharides, collagen, fibronectin and laminin. Other coatings, including hirudin, teflon, teflon-like coatings, PVDF, fluorinated polymers, and other coatings which are inert relative to the capsular bag may be employed to increase lubricity at locations (such as the optics and distending members) on the lens system which contact the bag, or Hema or silicone can be used to impart hydrophilic or hydrophobic properties to any intraocular lens system.

It is also desirable to subject any intraocular lens system and/or the mold surfaces to a surface passivation process to improve biocompatibility. This may be done via conventional techniques such as chemical etching or plasma treatment.

Furthermore, appropriate surfaces (such as the outer edges/surfaces of the viewing elements, biasing elements, distending members, retention members, etc.) of any intraocular lens system can be textured or roughened to improve adhesion to the capsular bag. This may be accomplished by using conventional procedures such as plasma treatment, etching, dipping, vapor deposition, mold surface modification, etc. The selected material and lens configuration should be able to withstand secondary operations after molding/casting such as polishing, cleaning and sterilization processes involving the use of an autoclave, or ethylene oxide or radiation. After the mold is opened, the lens should undergo deflashing, polishing and cleaning operations, which typically involve a chemical or mechanical process, or a combination thereof. Suitable mechanical processes include tumbling, shaking and vibration; a tumbling process may involve the use of a barrel with varying grades of glass beads, fluids such as alcohol or water and polishing compounds such as aluminum oxides. Process rates are material dependent; for example, a tumbling process for silicone should utilize a 6" diameter barrel moving at 30-100 RPM. It is contemplated that several different steps of polishing and cleaning may be employed before the final surface quality is achieved.

In one embodiment, the lens system is held in a fixture to provide increased separation between, and improved process effect on, the anterior and posterior viewing elements during the deflashing/polishing/cleaning operations. In another embodiment, the lens system is everted or turned "inside-out" so that the inner faces of the viewing elements are better exposed during a portion of the deflashing/polishing/cleaning. A curing process may also be desirable in manufacturing the lens system 100. If the lens system is produced from silicone entirely at room temperature, the curing time can be as long as several days. If the mold is maintained at about 50° C., the curing time is reduced to about 24 hours; if the mold is preheated to 100-200° C. the curing time can be as short as about 3-15 minutes. Of course, the time-temperature combinations vary for other materials.

U.S. Pat. No. 6,884,261, incorporated by reference herein, describes several other embodiments of an accommodating intraocular lens. Any part of any embodiment disclosed in U.S. Pat. No. 6,884,261 may comprise one of the materials disclosed herein.

III. The Human Eye and Accommodation

Figure 2:
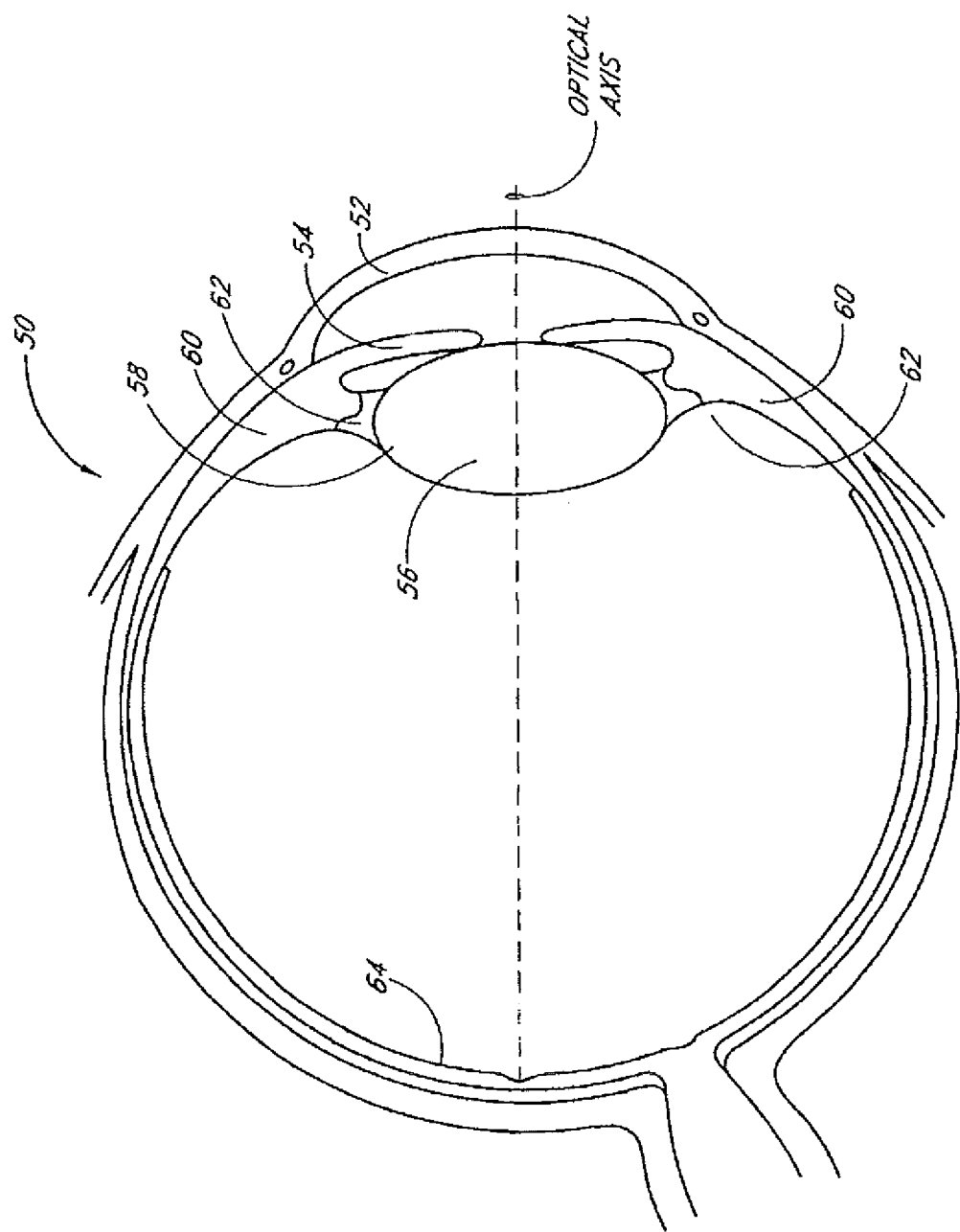
FIG. 2 is a sectional view of the human eye, with the lens in the accommodated state.

FIGS. 1 and 2 show the human eye 50 in section. Of particular relevance to the present disclosure are the cornea 52, the iris 54 and the lens 56, which is situated within the elastic, membranous capsular bag or lens capsule 58. The capsular bag 58 is surrounded by and suspended within the ciliary muscle 60 by ligament-like structures called zonules 62.

As light enters the eye 50, the cornea 52 and the lens 56 cooperate to focus the incoming light and form an image on the retina 64 at the rear of the eye, thus facilitating vision. In the process known as accommodation, the shape of the lens 56 is altered (and its refractive properties thereby adjusted) to allow the eye 50 to focus on objects at varying distances. A typical healthy eye has sufficient accommodation to enable focused vision of objects ranging in distance from infinity (generally defined as over 20 feet from the eye) to very near (closer than 10 inches).

The lens 56 has a natural elasticity, and in its relaxed state assumes a shape that in cross-section resembles a football. Accommodation occurs when the ciliary muscle 60 moves the lens from its relaxed or "unaccommodated" state (shown in FIG. 1) to a contracted or "accommodated" state (shown in FIG. 2). Movement of the ciliary muscle 60 to the relaxed/unaccommodated state increases tension in the zonules 62 and capsular bag 58, which in turn causes the lens 56 to take on a thinner (as measured along the optical axis) or taller shape as shown in FIG. 1. In contrast, when the ciliary muscle 60 is in the contracted/accommodated state, tension in the zonules 62 and capsular bag 58 is decreased and the lens 56 takes on the fatter or shorter shape shown in FIG. 2. When the ciliary muscles 60 contract and the capsular bag 58 and zonules 62 slacken, some degree of tension is maintained in the capsular bag 58 and zonules 62.

IV. The Lens System

Structure

Generally, the embodiments provide intraocular lenses comprising: an optic body comprising a first hydrophobic soft acrylic copolymer; and a haptic comprising a first silicone connected to the optic body. In some embodiments, the hydrophobic soft acrylic copolymer may be any copolymer described herein. In some embodiments, the optic body consists essentially of the hydrophobic soft acrylic copolymer. Alternatively, a portion of the optic body may be the hydrophobic soft acrylic copolymer. Additionally, the optic body may further comprise a second silicone. For example, the optic body may be partially hydrophobic soft acrylic copolymer and partially silicone.

In some embodiments, the intraocular lens is a dual optic accommodative lens comprising an anterior optic body, a posterior optic body, and a haptic connecting the anterior optic body to the posterior optic body. In some embodiments, the anterior optic body comprises the first hydrophobic soft acrylic copolymer; the posterior optic body comprises a second hydrophobic soft acrylic copolymer; and the haptic comprises the first silicone. Alternatively, in some embodiments the anterior optic body comprises the first hydrophobic soft acrylic copolymer; the posterior optic body comprises the second silicone; and the haptic comprises the first silicone. In another alternative embodiment, the anterior optic body comprises the second silicone; the posterior optic body comprises the first hydrophobic soft acrylic copolymer; and the haptic comprises the first silicone.

In any of the above embodiments, the first silicone and the second silicone may be the same or different; and the first and second soft acrylic copolymer may be the same or different.

In some embodiments, the intraocular lens further comprises: an anterior viewing element; a posterior viewing element; and a biasing structure connecting the anterior viewing element to the posterior viewing element. With respect to these embodiments, a biasing structure is a type of haptic which connects two viewing elements. In these embodiments, the biasing structure may provide a variable spacing between the anterior viewing element and the posterior viewing element. In these embodiments, (i) at least a portion of at least one of the anterior viewing element and the posterior viewing element comprises at least a portion of the acrylic component; (ii) at least a portion of at least one of the anterior viewing element, the posterior viewing element, and the biasing structure comprises at least a portion of the silicone component; and (iii) at least a portion of at least one of the anterior viewing element, the posterior viewing element, and the biasing structure comprises at least a portion of the plurality of silicon-carbon covalent bonds formed from a hydrosilation reaction occurring between the acrylic component and the silicone component. In some embodiments, the haptic portion of the lens comprises silicone.

Figure 3:
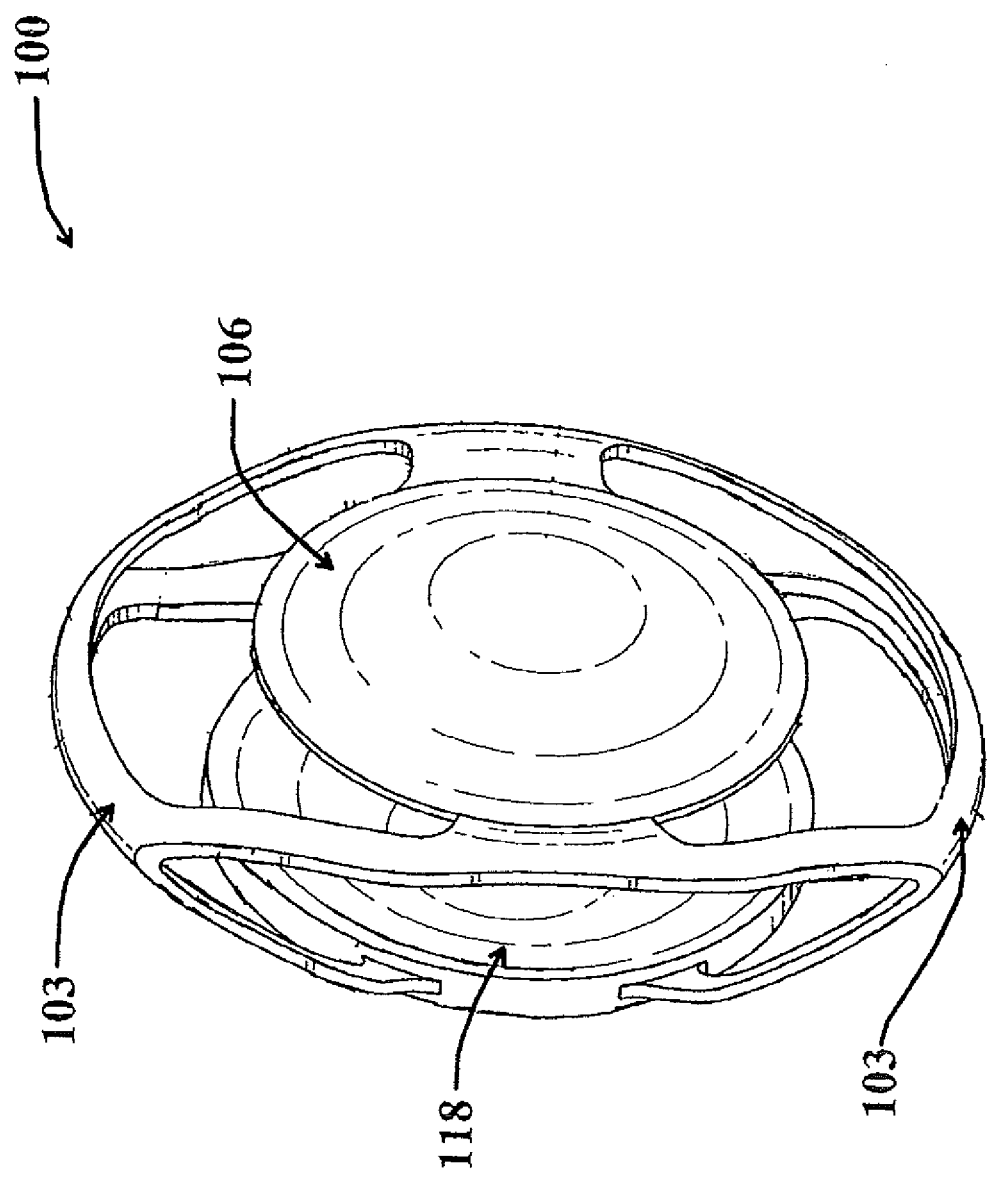
FIG. 3 is a depiction of one embodiment of an intraocular lens system.

One embodiment depicted in FIG. 3 shows one example of a lens system 100 comprising an anterior viewing element 106, a posterior viewing element 118, and a biasing structure 103. The viewing elements 106 and 118 and the biasing structure may take many forms other than the ones depicted in FIG. 3.

In some embodiments, the acrylic component comprises at least a portion of the anterior viewing element or at least a portion of the posterior viewing element, and the silicone component comprises at least a portion of the biasing structure.

In some embodiments, the acrylic component comprises at least a portion of the anterior viewing element and at least a portion of the posterior viewing element, and the silicone component comprises at least a portion of the biasing structure.

In some embodiments, at least a portion of the anterior viewing element comprises at least a portion of the acrylic component, at least a portion of the posterior viewing element comprises at least a portion of the acrylic component, and at least a portion of the biasing structure comprises at least a portion of the silicone component.

Thus, a viewing element may be composed entirely of the acrylic copolymer described herein. Alternatively, a viewing element may be composed entirely of silicone provided that there is a second viewing element that comprises the acrylic copolymer.

Alternatively, a viewing element may comprise both the acrylic copolymer and silicone. For example, the viewing element may have a central portion comprising the acrylic copolymer. This center portion may be completely or at least partially surrounded on the edges (e.g. along the circumference of the circular viewing element) to form a frame comprising a silicone. The frame and the center portion may be held together by silicon-carbon bonds formed by a hydrosilation reaction. In another example, the viewing element may have an inner portion comprising the acrylic copolymer which is completely or at least partially coated by a layer of silicone, and the inner acrylic portion and the silicone coating may be held together by silicon-carbon bonds formed by a hydrosilation reaction. Other combinations of acrylic and silicone are also possible.

Thus, in embodiments where there are an anterior and a posterior viewing element, the anterior viewing element may be composed entirely of the acrylic copolymer and the posterior viewing element may be composed entirely of the acrylic copolymer. Alternatively, the anterior viewing element may be composed entirely of the acrylic copolymer and the posterior viewing element may comprise both the acrylic copolymer and a silicone. Alternatively, the anterior viewing element may be composed entirely of the acrylic copolymer and the posterior viewing element may be composed entirely of silicone. Alternatively, the anterior viewing element may comprise both the acrylic copolymer and a silicone and the posterior viewing element may be composed entirely of the acrylic copolymer. Alternatively, the anterior viewing element may comprise both the acrylic copolymer and a silicone and the posterior viewing element may comprise both the acrylic copolymer and a silicone. Alternatively, the anterior viewing element may comprise both the acrylic copolymer and a silicone and the posterior viewing element may be composed entirely of silicone. Alternatively, the anterior viewing element may be composed entirely of silicone and the posterior viewing element may be composed entirely of the acrylic copolymer. Alternatively, the anterior viewing element may be composed entirely of silicone and the posterior viewing element may comprise both the acrylic copolymer and a silicone. Where a viewing element comprises both silicone and acrylic, they may be present in any combination or orientation, including but not limited to where the silicone is substantially on the circumference of an acrylic element (including on an edge of the element and/or the periphery of an anterior and/or posterior surface of the element) and where the silicone forms a coating on one or both of the anterior and posterior surfaces of an acrylic element.

With respect to any of the embodiments related to the composition of the viewing elements, in some embodiments, a haptic, including a biasing element may comprise silicone. In these embodiments, the haptic may be entirely composed of silicone, or may be partially composed of silicone, or may comprise both silicone and an acrylic copolymer.

The embodiments above describe parts of the structure of an intraocular lens where a silicone and an acrylic copolymer are in contact. At any part of the structure where these two materials are in contact, they may be held together by a plurality of Si—C covalent bonds from a hydrosilation reaction as described herein.

Figure 4:
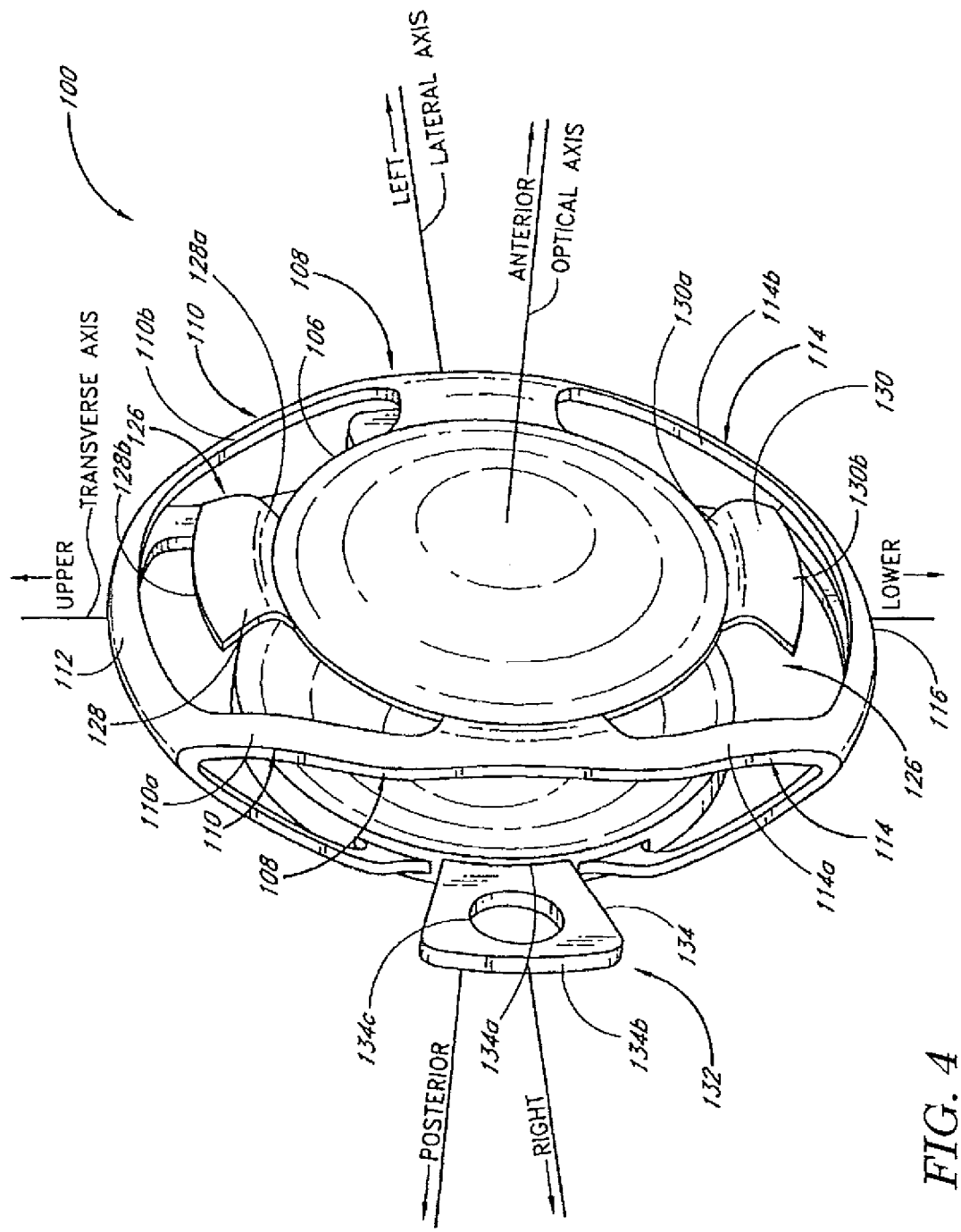
FIG. 4 is a perspective view of one embodiment of an intraocular lens system.

FIGS. 4-18 depict one embodiment of an intraocular lens system 100 which is configured for implantation into the capsular bag 58 in place of the natural lens 56, and is further configured to change the refractive properties of the eye in response to the eye's natural process of accommodation. With reference to FIG. 4, a set of axes is included to illustrate the sense of directional terminology which will be used herein to describe various features of the lens system 100. The terms "anterior" and "posterior" refer to the depicted directions on the optical axis of the lens 100 shown in FIG. 4. When the lens 100 is implanted in an eye, the anterior direction extends toward the cornea and the posterior direction extends toward the retina, with the optical axis of the lens substantially coincident with the optical axis of the eye shown in FIGS. 1 and 2. The terms "left" and "right" refer to the directions shown on the lateral axis, which is orthogonal to the optical axis. In addition, the terms "upper" and "lower" refer to the directions depicted on the transverse axis which is orthogonal to both of the optical axis and the lateral axis.

This system of axes is depicted purely to facilitate description herein; thus, it is not intended to limit the possible orientations which the lens system 100 may assume during use. For example, the lens system 100 may rotate about, or may be displaced along, the optical axis during use without detracting from the performance of the lens. It is clear that, should the lens system 100 be so rotated about the optical axis, the transverse axis may no longer have an upper-lower orientation and the lateral axis may no longer have a left-right orientation, but the lens system 100 will continue to function as it would when oriented as depicted in FIG. 4. Accordingly, when the terms "upper," "lower," "left" or "right" are used in describing features of the lens system 100, such use should not be understood to require the described feature to occupy the indicated position at any or all times during use of the lens system 100. Similarly, such use should not be understood to require the lens system 100 to maintain the indicated orientation at any or all times during use.

Figure 5:
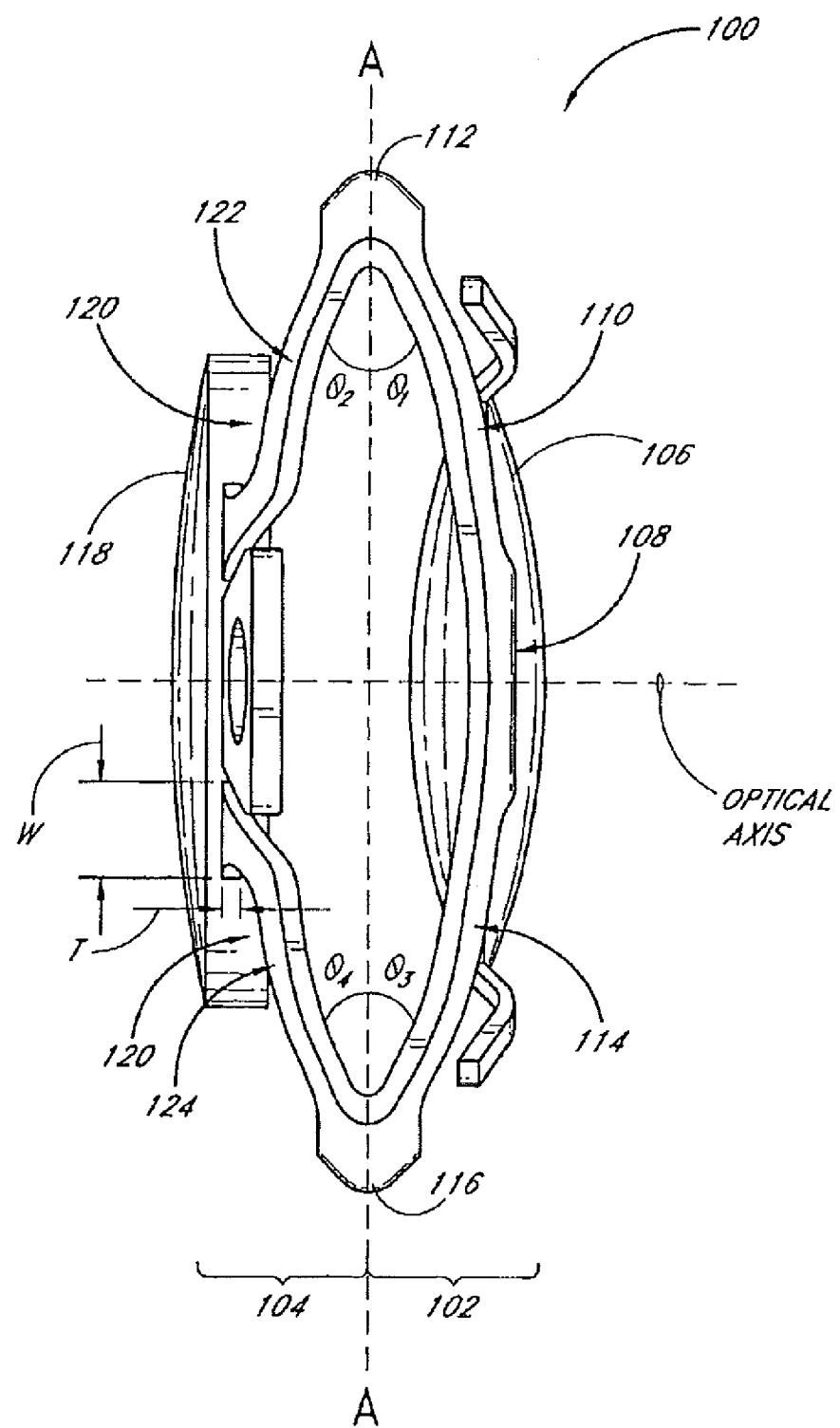
FIG. 5 is a side view of the lens system.

As best seen in FIG. 5, the lens system 100 has an anterior portion 102 which is anterior or forward of the line A-A (which represents a plane substantially orthogonal to the optical axis and intersecting first and second apices 112, 116) and a posterior portion 104 which is posterior or rearward of the line A-A. The anterior portion 102 comprises an anterior viewing element 106 and an anterior biasing element 108. The anterior biasing element 108 in turn comprises a first anterior translation member 110 which extends from the anterior viewing element 106 to the first apex 112 and a second anterior translation member 114 which extends from the anterior viewing element 106 to the second apex 116. In the illustrated embodiment the first anterior translation member 110 comprises a right arm 110a and a left arm 110b (see FIG. 4). In addition, the depicted second anterior translation member 114 comprises a right arm 114a and a left arm 114b. However, in other embodiments either or both of the first and second anterior translation members 110, 114 may comprise a single arm or member, or more than two arms or members.

Figure 6:
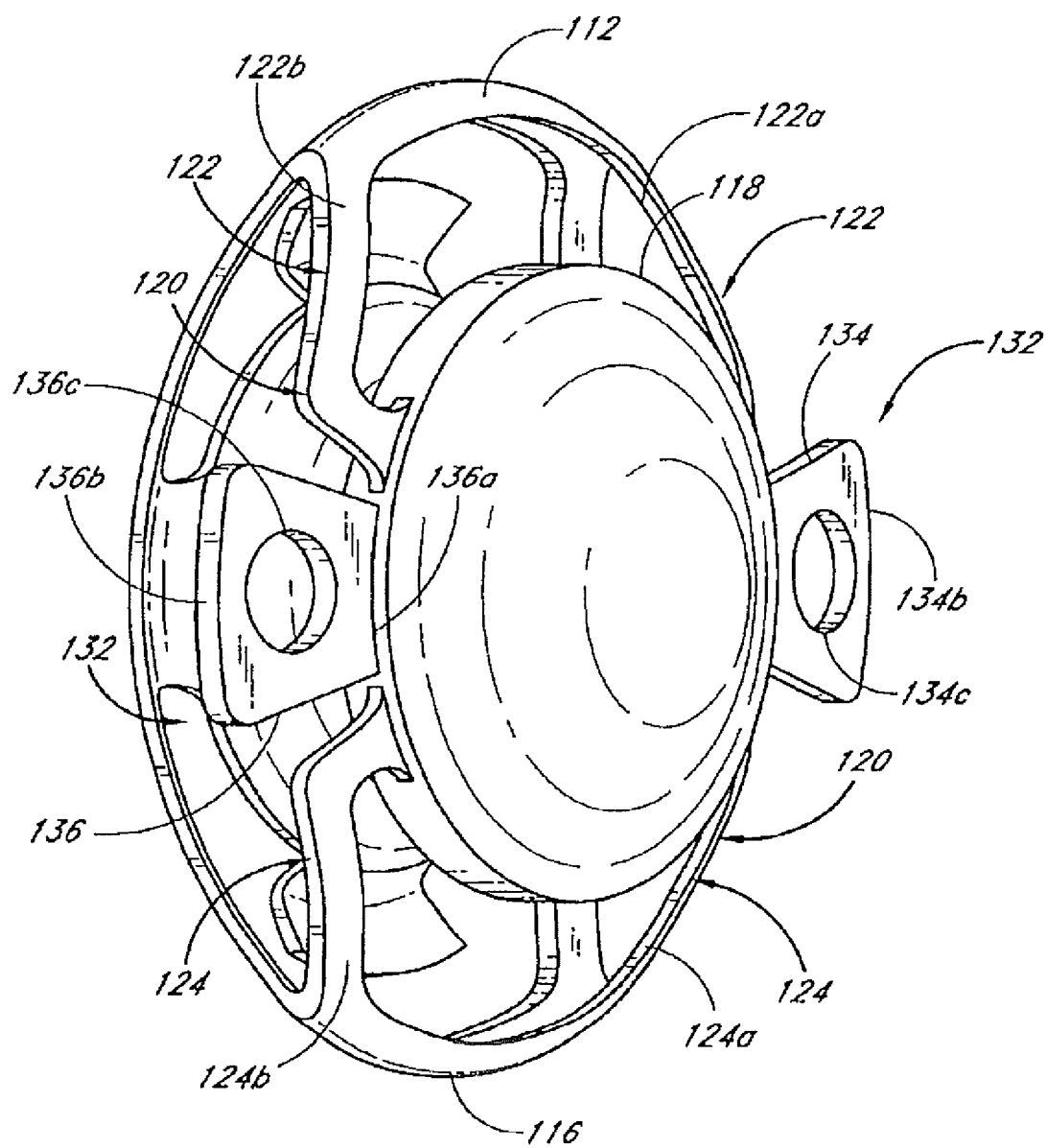
FIG. 6 is a rear perspective view of the lens system.
Figure 8:
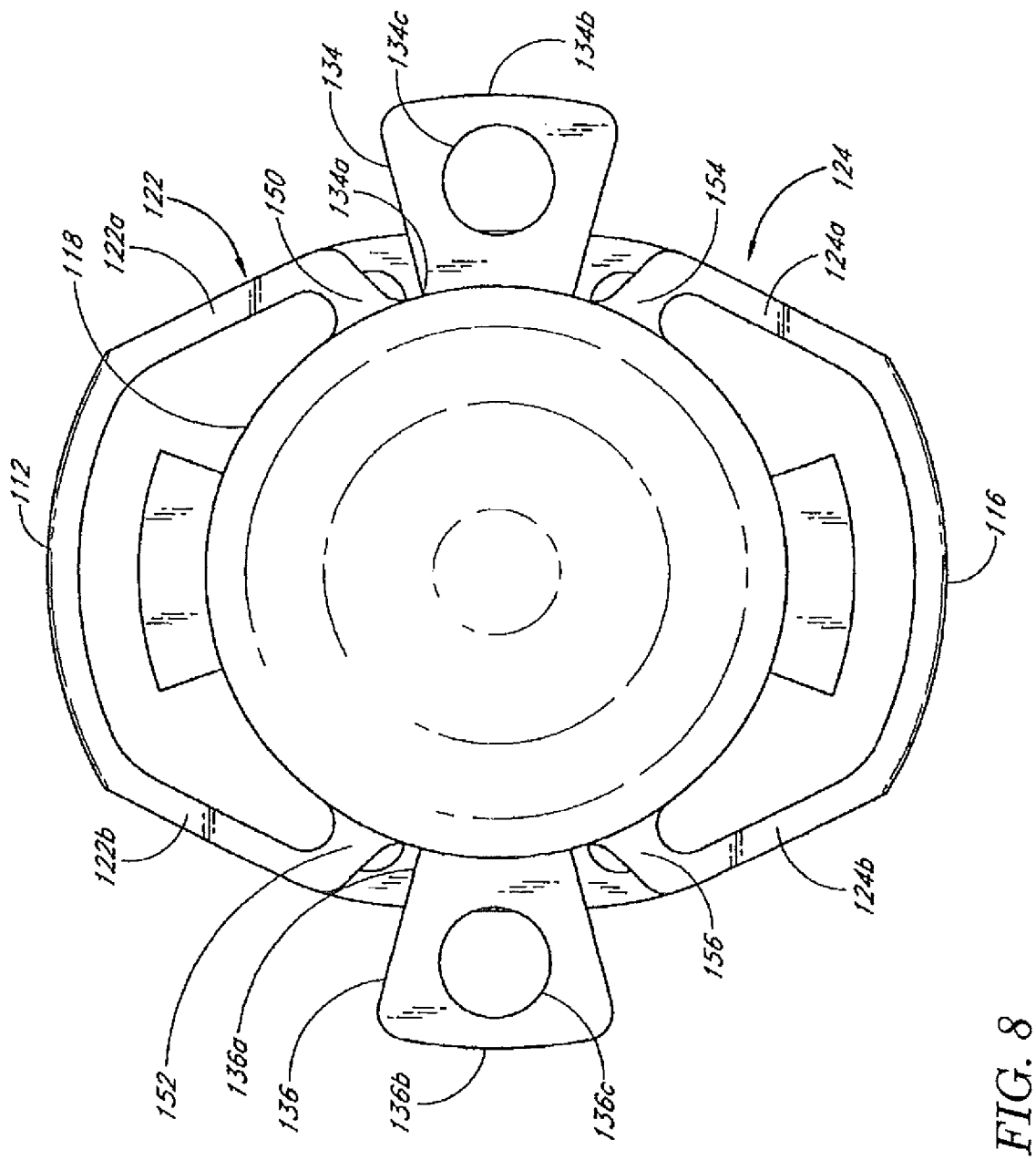
FIG. 8 is a rear view of the lens system.
Figure 9:
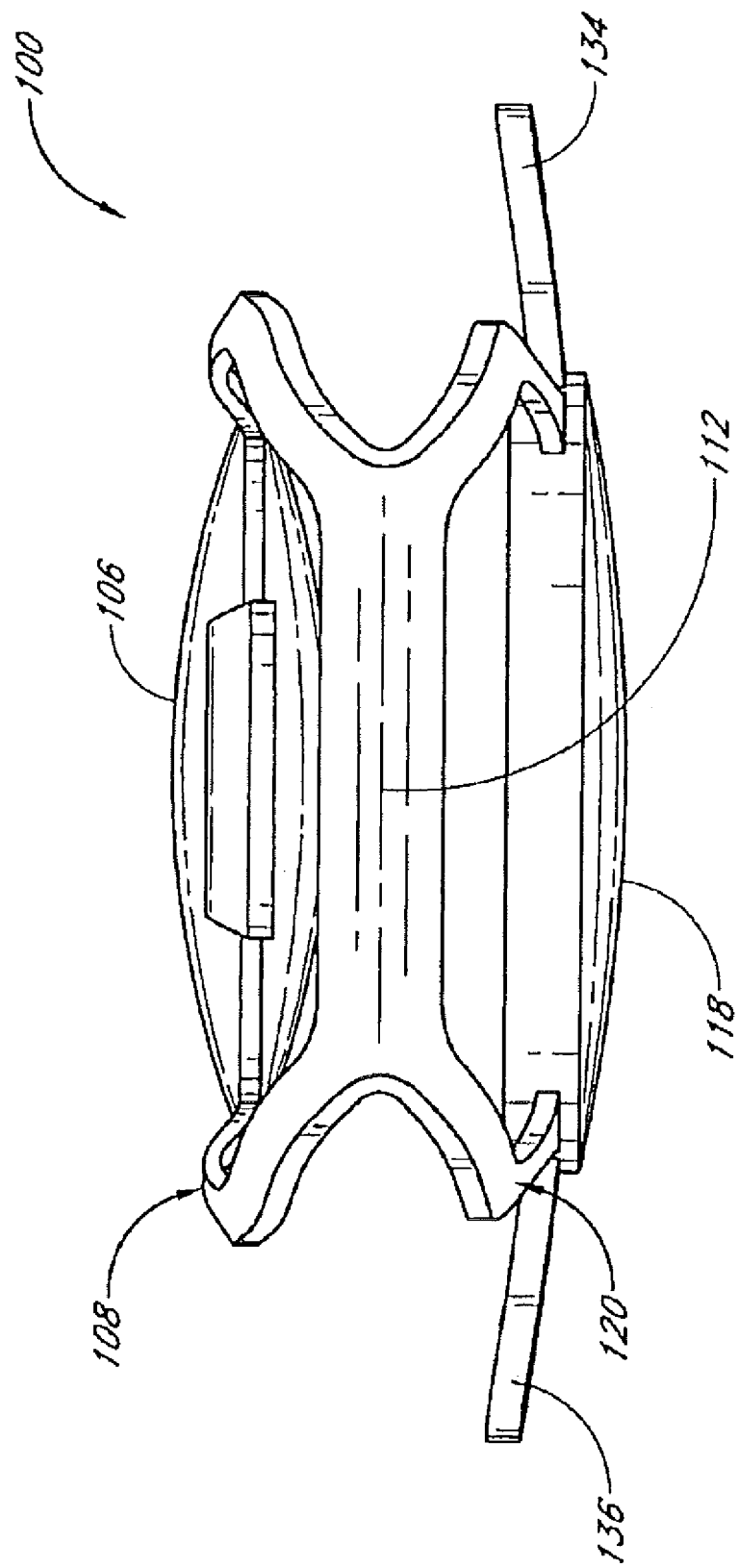
FIG. 9 is a top view of the lens system.
Figures 10, 11:
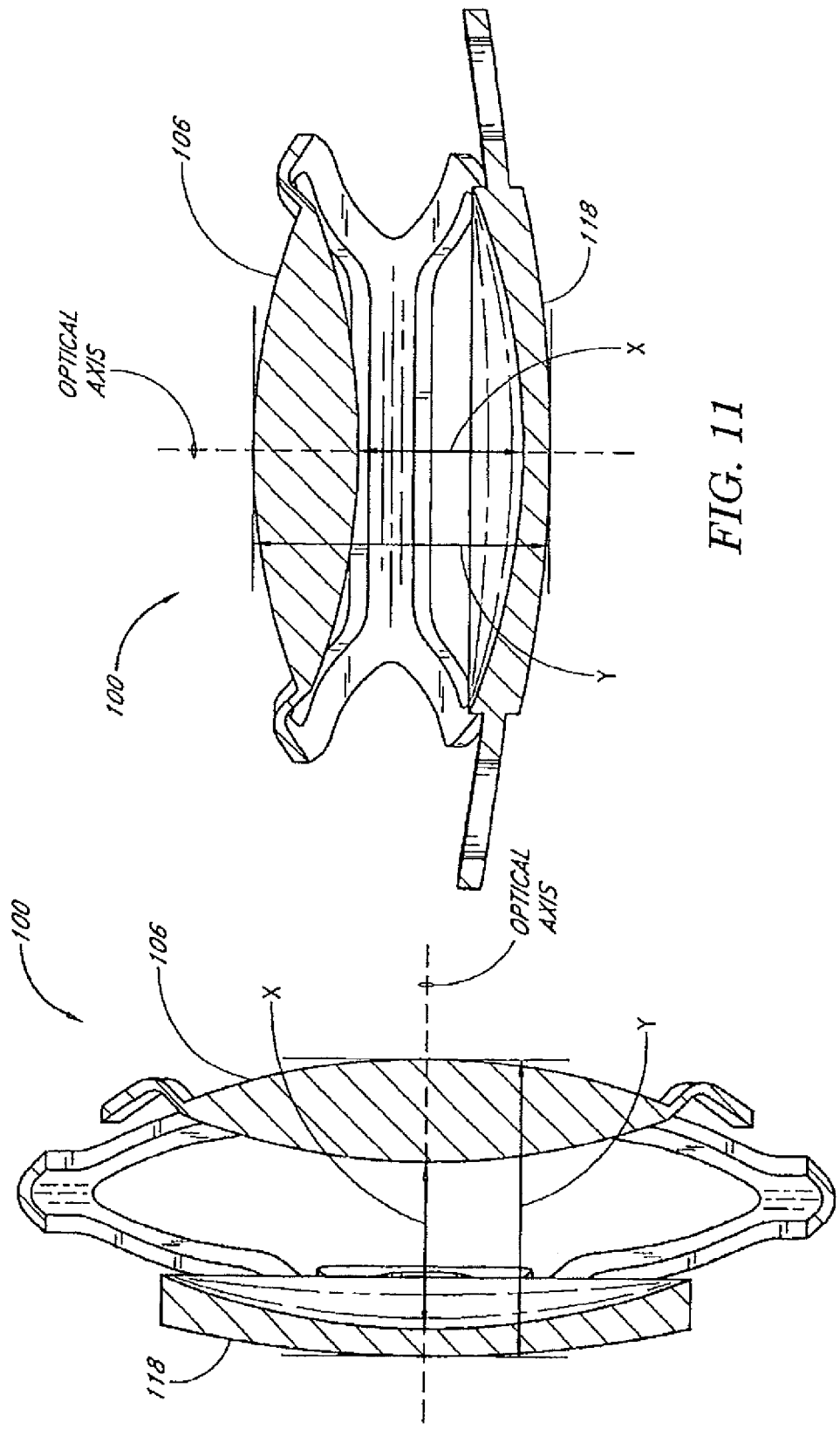
FIG. 10 is a side sectional view of the lens system.
FIG. 11 is a top sectional view of the lens system.
Figure 12:
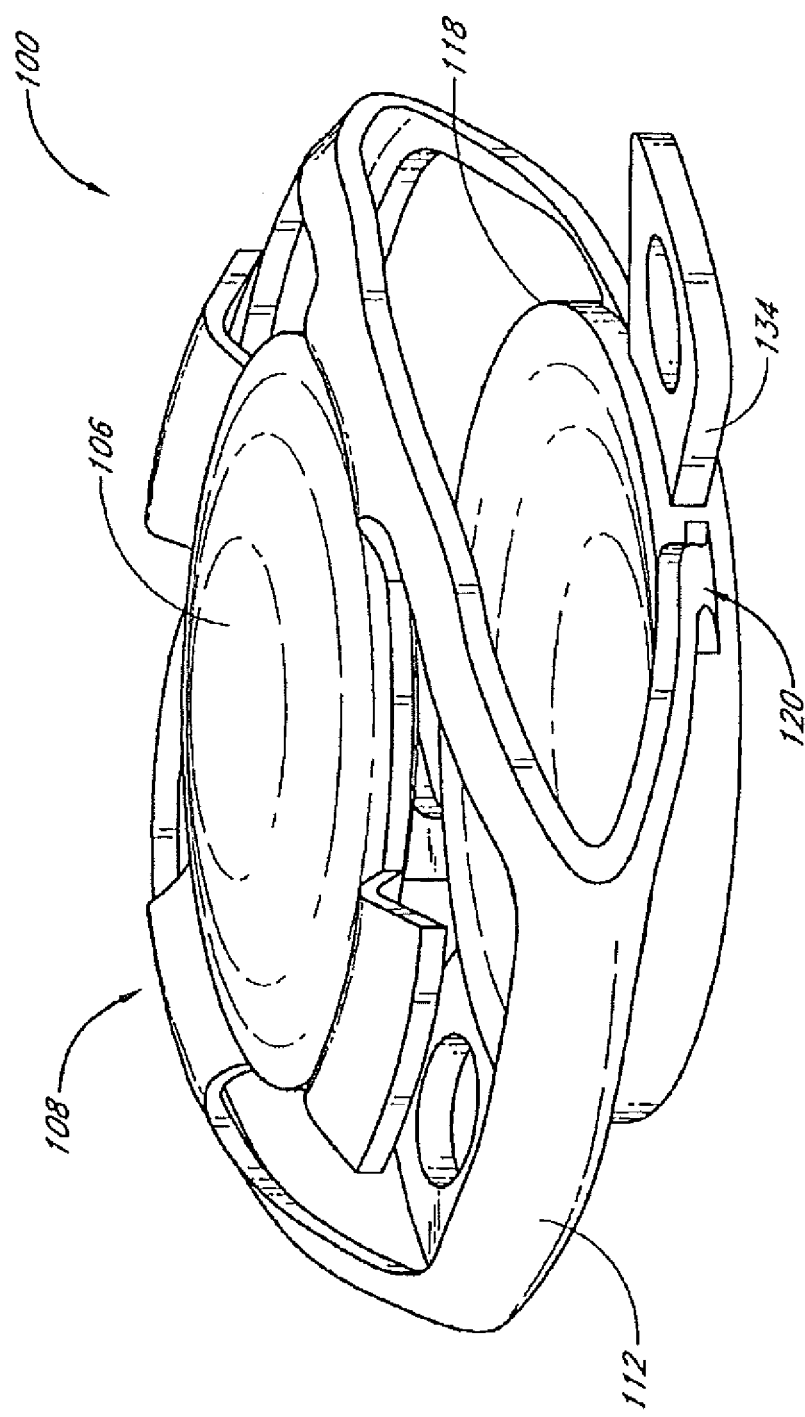
FIG. 12 is a second perspective view of the lens system.
Figure 13:
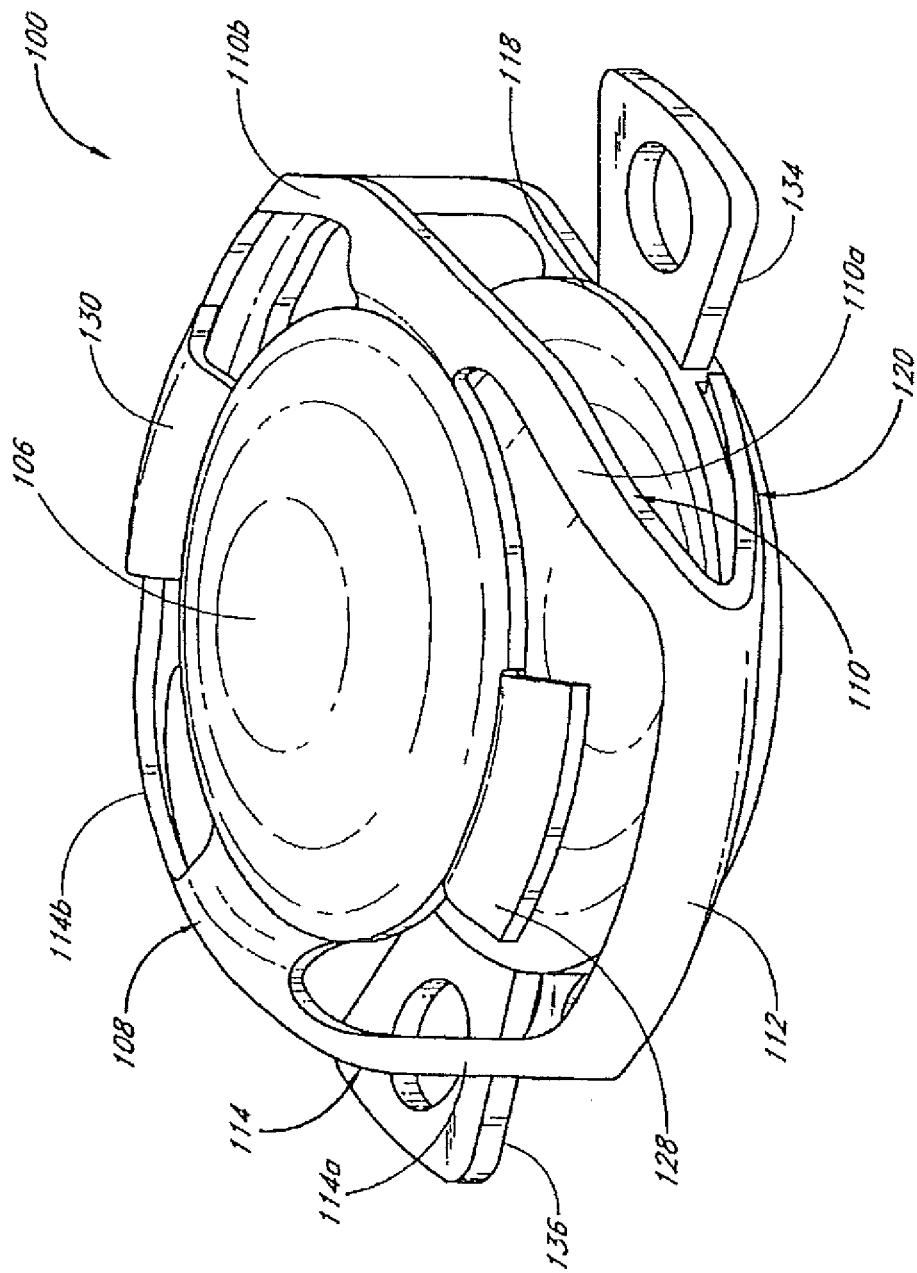
FIG. 13 is a third perspective view of the lens system.
Figure 15:
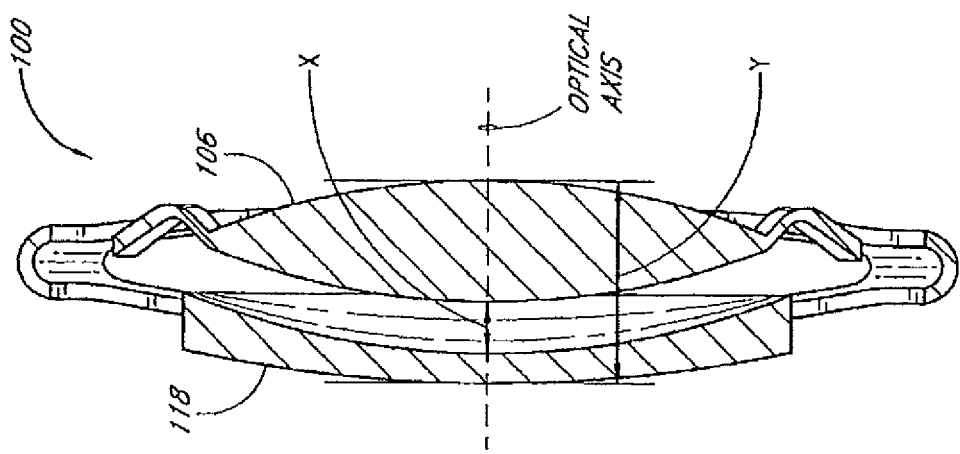
FIG. 15 is a side sectional view of the lens system in the unaccommodated state.
Figure 14:
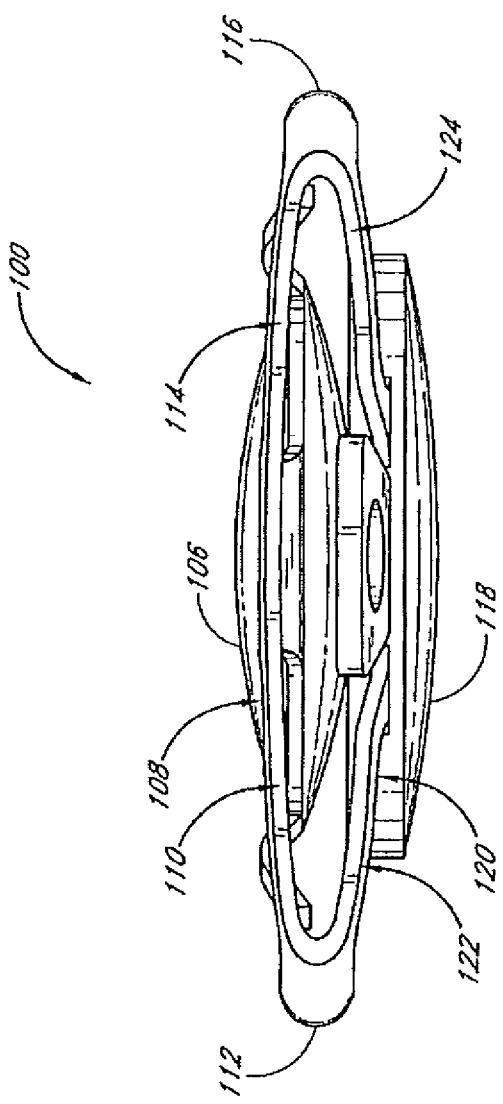
FIG. 14 is a side view of the lens system in the unaccommodated state.
Figure 16:
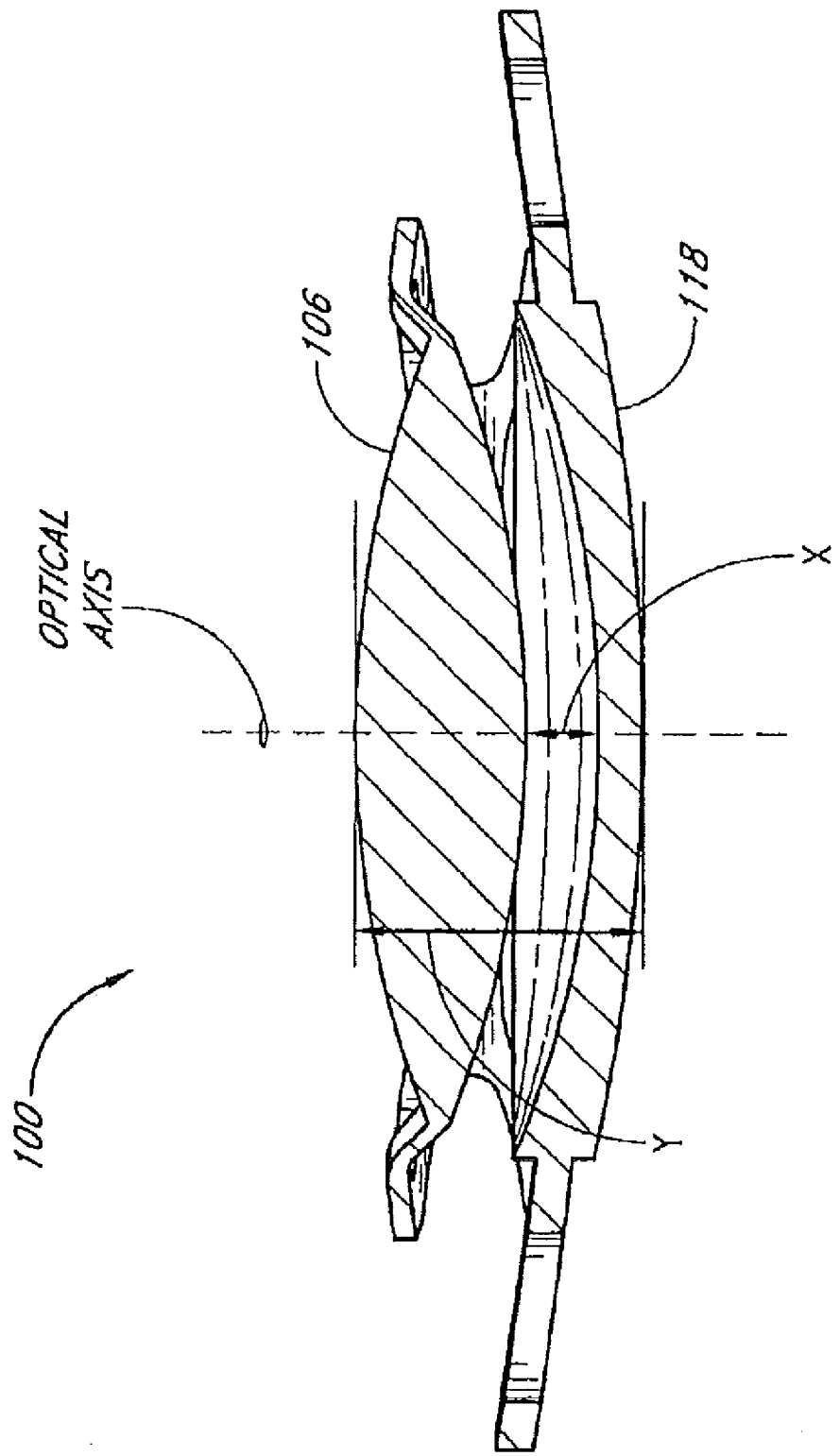
FIG. 16 is a top sectional view of the lens system in the unaccommodated state.
Figure 17:
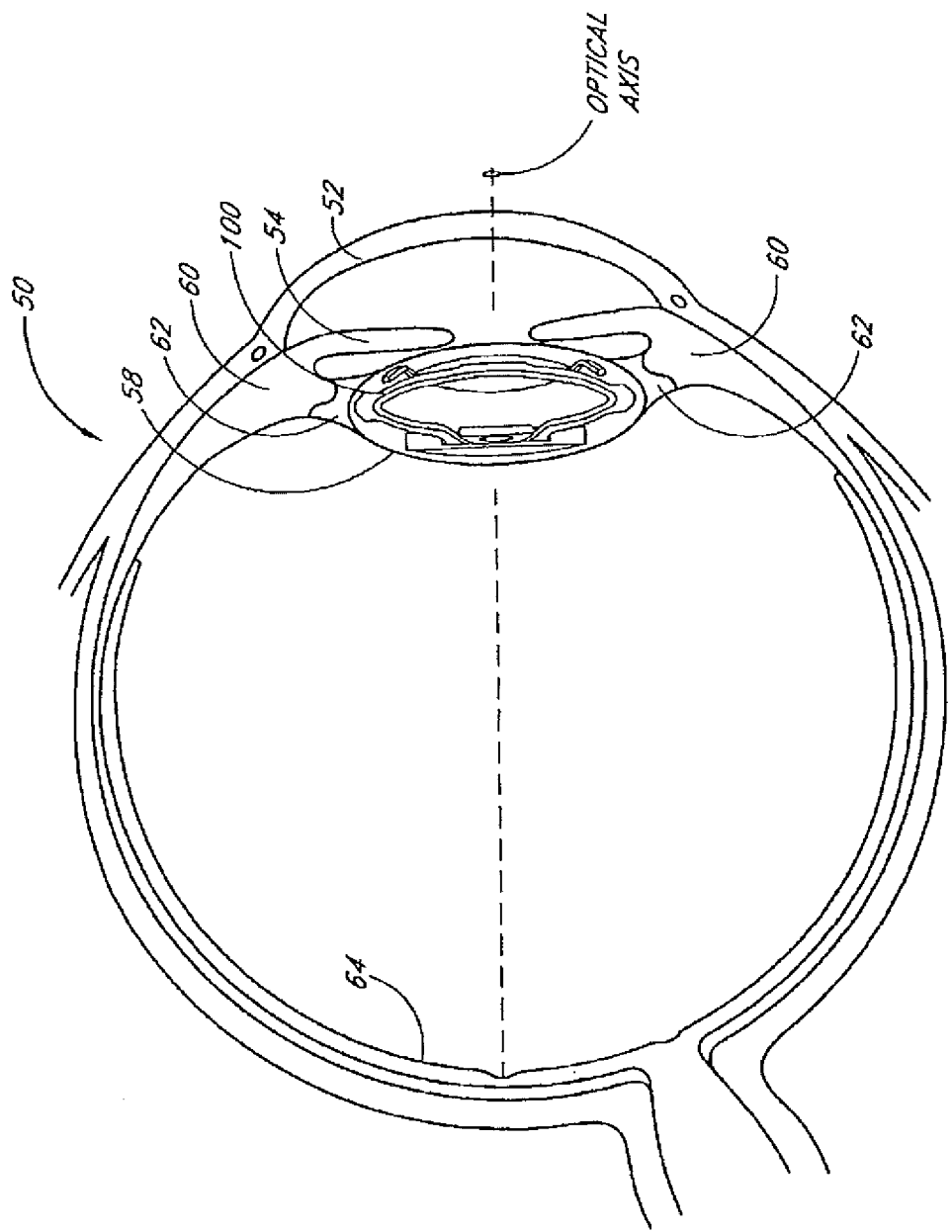
FIG. 17 is a sectional view of the human eye with the lens system implanted in the capsular bag and the lens system in the accommodated state.
Figure 18:
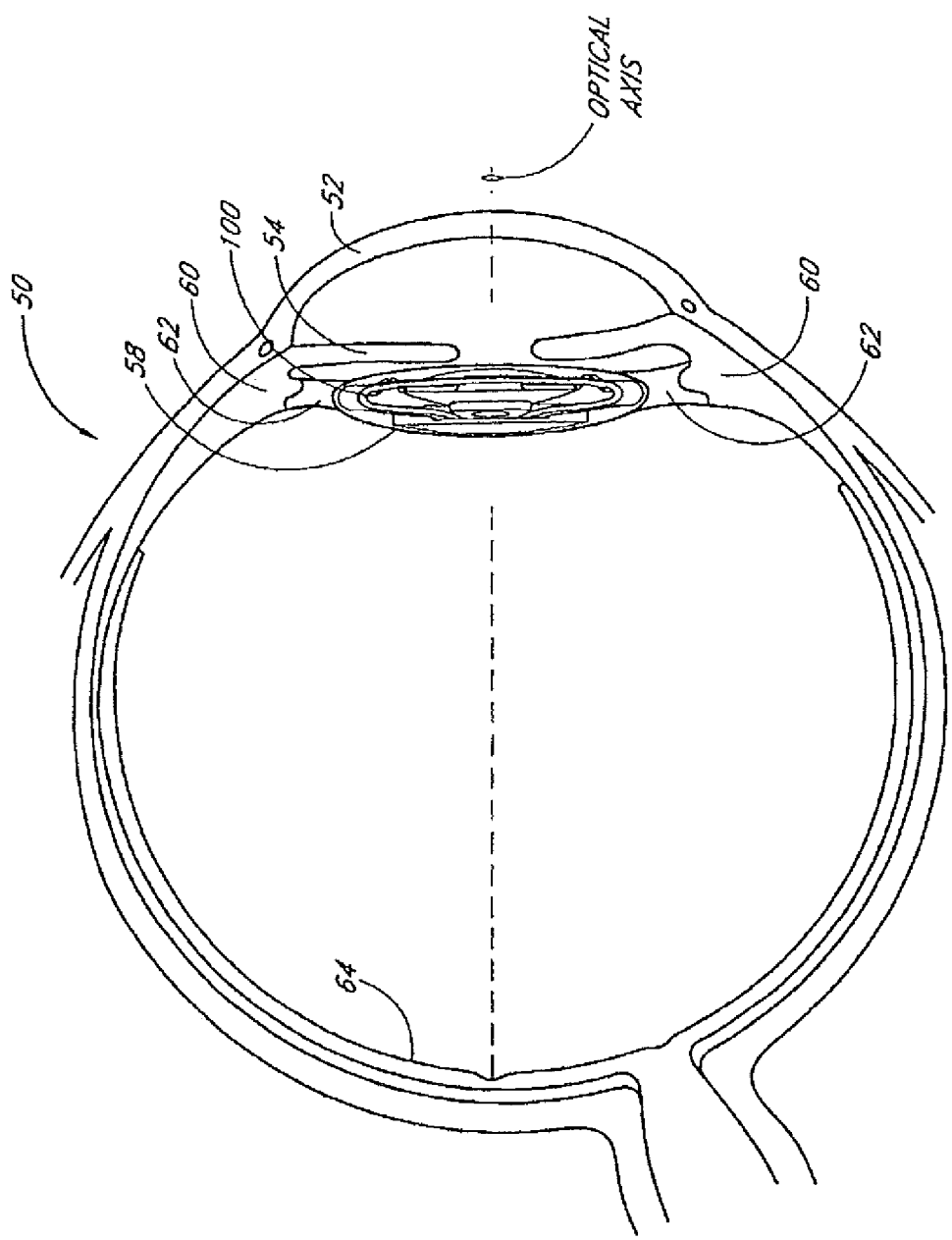
FIG. 18 is a sectional view of the human eye with the lens system implanted in the capsular bag and the lens system in the unaccommodated state.
Figure 19:
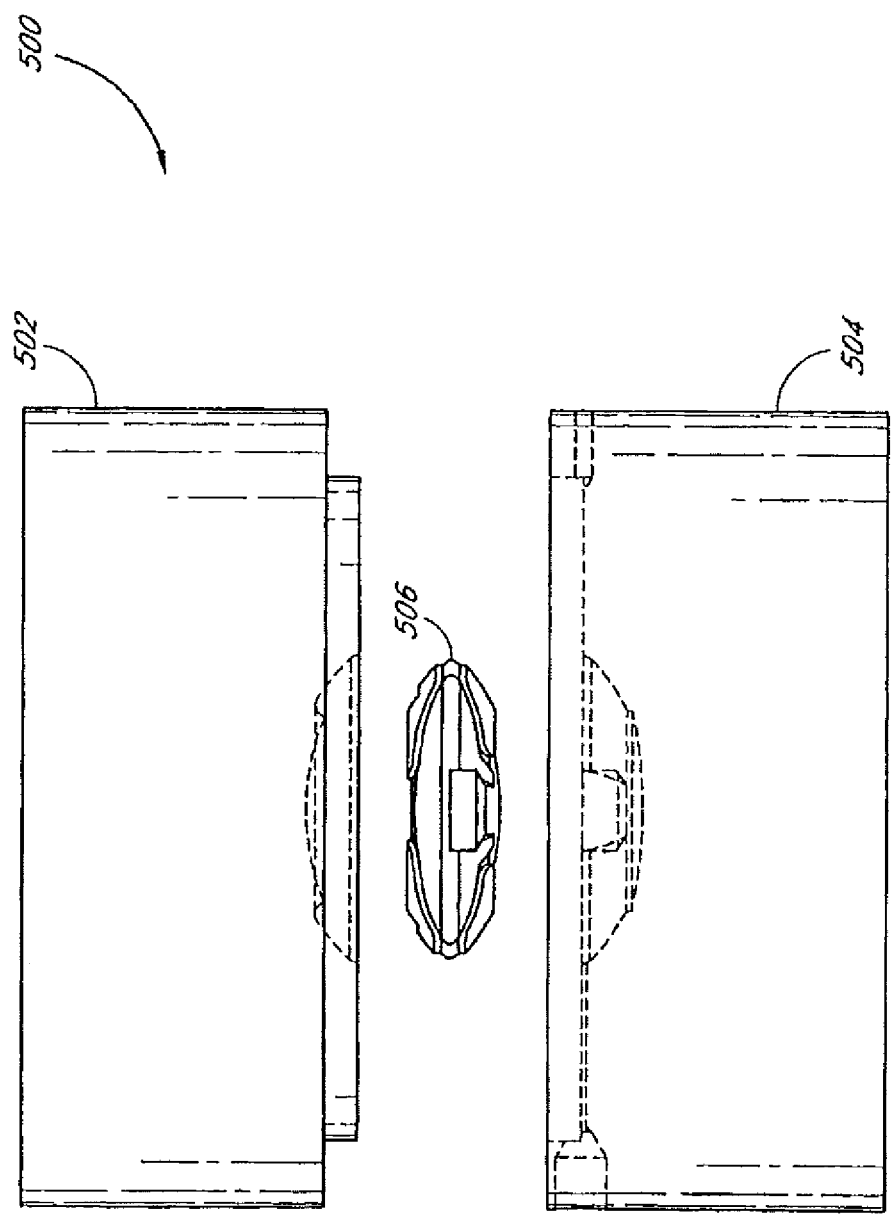
FIG. 19 is a side view of a mold system for forming the lens system.

As best seen in FIGS. 5, 6 and 8, the posterior portion 104 includes a posterior viewing element 118 and a posterior biasing element 120. The posterior biasing element 120 includes a first posterior translation member 122 extending from the posterior viewing element 118 to the first apex 112 and a second posterior translation member 124 extending from the posterior viewing element 118 to the second apex 116. In the illustrated embodiment, the first posterior translation member comprises a right arm 122a and a left arm 122b. Likewise, the depicted second posterior translation member 124 comprises a right arm 124a and a left arm 124b. However, in other embodiments either or both of the first and second posterior translation members 122, 124 may comprise a single arm or member, or more than two arms or members.

In the embodiment shown in FIG. 4, the anterior biasing element 108 and the posterior biasing element are configured symmetrically with respect to the plane A-A as the lens system 100 is viewed from the side. As used herein to describe the biasing elements 108, 120, "symmetric" or "symmetrically" means that, as the lens system 100 is viewed from the side, the first anterior translation member 110 and the first posterior translation member 122 extend from the first apex 112 at substantially equal first anterior and posterior biasing angles $\theta_1$, $\theta_2$ with respect to the line A-A (which, again, represents the edge of a plane which is substantially orthogonal to the optical axis and intersects the first and second apices 112, 116) and/or that the second anterior translation member 114 and the second posterior translation member 124 extend from the second apex 116 at substantially equal second anterior and posterior biasing angles $\theta_3$, $\theta_4$ with respect to the line A-A. Alternative or asymmetric configurations of the biasing elements are possible, as will be discussed in further detail below. It should be further noted that a symmetric configuration of the biasing elements 108, 120 does not dictate symmetric positioning of the viewing elements with respect to the line A-A; in the embodiment shown in FIG. 4 the anterior viewing element 106 is closer to the line A-A than is the posterior viewing element.

Preferably, both the anterior viewing element 106 and the posterior viewing element 118 comprise an optic or lens having refractive power. (As used herein, the term "refractive" or "refractive power" shall include "diffractive" or "diffractive power".) The preferred power ranges for the optics are discussed in detail below. In alternative embodiments one or both of the anterior and posterior viewing elements 106, 118 may comprise an optic with a surrounding or partially surrounding perimeter frame member or members, with some or all of the biasing elements/translation members attached to the frame member(s). As a further alternative, one of the viewing elements 106, 118 may comprise a perimeter frame with an open/empty central portion or void located on the optical axis, or a perimeter frame member or members with a zero-power lens or transparent member therein. In still further variations, one of the viewing elements 106, 118 may comprise only a zero-power lens or transparent member.

In a presently preferred embodiment, a retention portion 126 is coupled to the anterior portion 102, preferably at the anterior viewing element 106. The retention portion 126 preferably includes a first retention member 128 and a second retention member 130, although in alternative embodiments the retention portion 126 may be omitted altogether, or may comprise only one retention member or more than two retention members. The first retention member 128 is coupled (e.g. by silicon-carbon covalent bonds formed by a hydrosilation reaction) to the anterior viewing element 106 at a fixed end 128a and also includes a free end 128b opposite the fixed end 128a. Likewise, the second retention member 130 includes a fixed end 130a and a free end 130b. The retention members 128, 130 are illustrated as being coupled to the anterior viewing element 106 at the upper and lower edges thereof; however, the retention members 128, 130 may alternatively be attached (e.g. by silicon-carbon covalent bonds formed by a hydrosilation reaction) to the anterior viewing element 106 at other suitable edge locations.

In the preferred embodiment, the posterior portion 104 includes a distending portion 132, preferably attached (e.g. by silicon-carbon covalent bonds formed by a hydrosilation reaction) to the posterior viewing element 118. The preferred distending portion 132 includes a first distending member 134 which in turn includes a fixed end 134a, a free end 134b opposite the fixed end 134a and preferably also includes an opening 134c formed therein. The preferred distending portion 132 also comprises a second distending member 136 with a fixed end 136a, a free end 136b and preferably an opening 136c formed therein. In alternative embodiments, the distending portion 132 may be omitted altogether, or may comprise a single distending member or more than two distending members. To optimize their effectiveness, the preferred location for the distending members 134, 136 is 90 degrees away (about the optical axis) from the apices 112, 116 on the posterior portion 104. Where the biasing elements form more than two apices (or where two apices are not spaced 180 degrees apart about the optical axis), one or more distending members may be positioned angularly midway between the apices about the optical axis. Alternatively, the distending member(s) may occupy other suitable positions relative to the apices (besides the "angularly midway" positions disclosed above); as further alternatives, the distending member(s) may be located on the anterior portion 102 of the lens system 100, or even on the apices themselves.

V. The Lens System

Function/Optics

The anterior and posterior biasing elements 108, 120 function in a springlike manner to permit the anterior viewing element 106 and posterior viewing element 118 to move relative to each other generally along the optical axis. The biasing elements 108, 120 bias the viewing elements 106, 118 apart so that the elements 106, 108 separate to the accommodated position or accommodated state shown in FIG. 5. Thus, in the absence of any external forces, the viewing elements are at their maximum separation along the optical axis. The viewing elements 106, 118 of the lens system 100 may be moved toward each other, in response to a ciliary muscle force of up to 2 grams, to provide an unaccommodated position by applying appropriate forces upon the anterior and posterior portions 102, 104 and/or the apices 112, 116.

When the lens system 100 is implanted in the capsular bag 58 (FIGS. 17-18) the above described biasing forces cause the lens system 100 to expand along the optical axis so as to interact with both the posterior and anterior aspects of the capsular bag. Such interaction occurs throughout the entire range of motion of the ciliary muscle 60. At one extreme the ciliary muscle is relaxed and the zonules 62 pull the capsular bag 58 radially so as to cause the bag to become more disk shaped. The anterior and posterior sides of the bag, in turn, apply force to the anterior and posterior portions 102, 104 of the lens system 100, thereby forcing the viewing elements 106, 118 toward each other into the accommodated position. At the other extreme, the ciliary muscle contracts and the zonules 62 move inwardly to provide slack in the capsular bag 58 and allow the bag to become more football-shaped. The slack in the bag is taken up by the lens system due to the biasing-apart of the anterior and posterior viewing elements 106, 118. As the radial tension in the bag is reduced, the viewing elements 106, 118 move away from each other into an accommodated position. Thus, the distance between the viewing elements 106, 118 depends on the degree of contraction or relaxation of the ciliary muscle 60. As the distance between the anterior and posterior viewing elements 106, 118 is varied, the focal length of the lens system 100 changes accordingly. Thus, when the lens system 100 is implanted into the capsular bag (see FIGS. 17-18) the lens system 100 operates in conjunction with the natural accommodation processes of the eye to move between the accommodated (FIG. 17) and unaccommodated (FIG. 18) states in the same manner as would a healthy "natural" lens. Preferably, the lens system 100 can move between the accommodated and unaccommodated states in less than about one second.

The entire lens system 100, other than the optic(s), thus comprises an articulated frame whose functions include holding the optic(s) in position within the capsular bag and guiding and causing movement of the optic(s) between the accommodated and unaccommodated positions.

In those embodiments where the optic(s) are installed into annular or other perimeter frame member(s) (see discussion below), the articulated frame may comprise a single piece of material, to obtain the performance advantages discussed above. It is believed that the assembly of the optic(s) to the articulated frame will not substantially detract from the achievement of these advantages.

The lens system 100 has sufficient dynamic range that the anterior and posterior viewing elements 106, 118 move about 0.5-4 mm, preferably about 1-3 mm, more preferably about 1-2 mm, and most preferably about 1.5 mm closer together when the lens system 100 moves from the accommodated state to the unaccommodated state. In other words the separation distance X (see FIGS. 10-11, 15-16) between the anterior and posterior viewing elements 106, 118, which distance may for present purposes be defined as the distance along the optical axis (or a parallel axis) between a point of axial intersection with the posterior face of the anterior viewing element 106 and a point of axial intersection with the anterior face of the posterior viewing element 118, decreases by the amount(s) disclosed above upon movement of the lens system 100 to the unaccommodated state. Simultaneously, in the preferred mode the total system thickness Y decreases from about 3.0-4.0 mm in the accommodated state to about 1.5-2.5 mm in the unaccommodated state.

Figure 7:
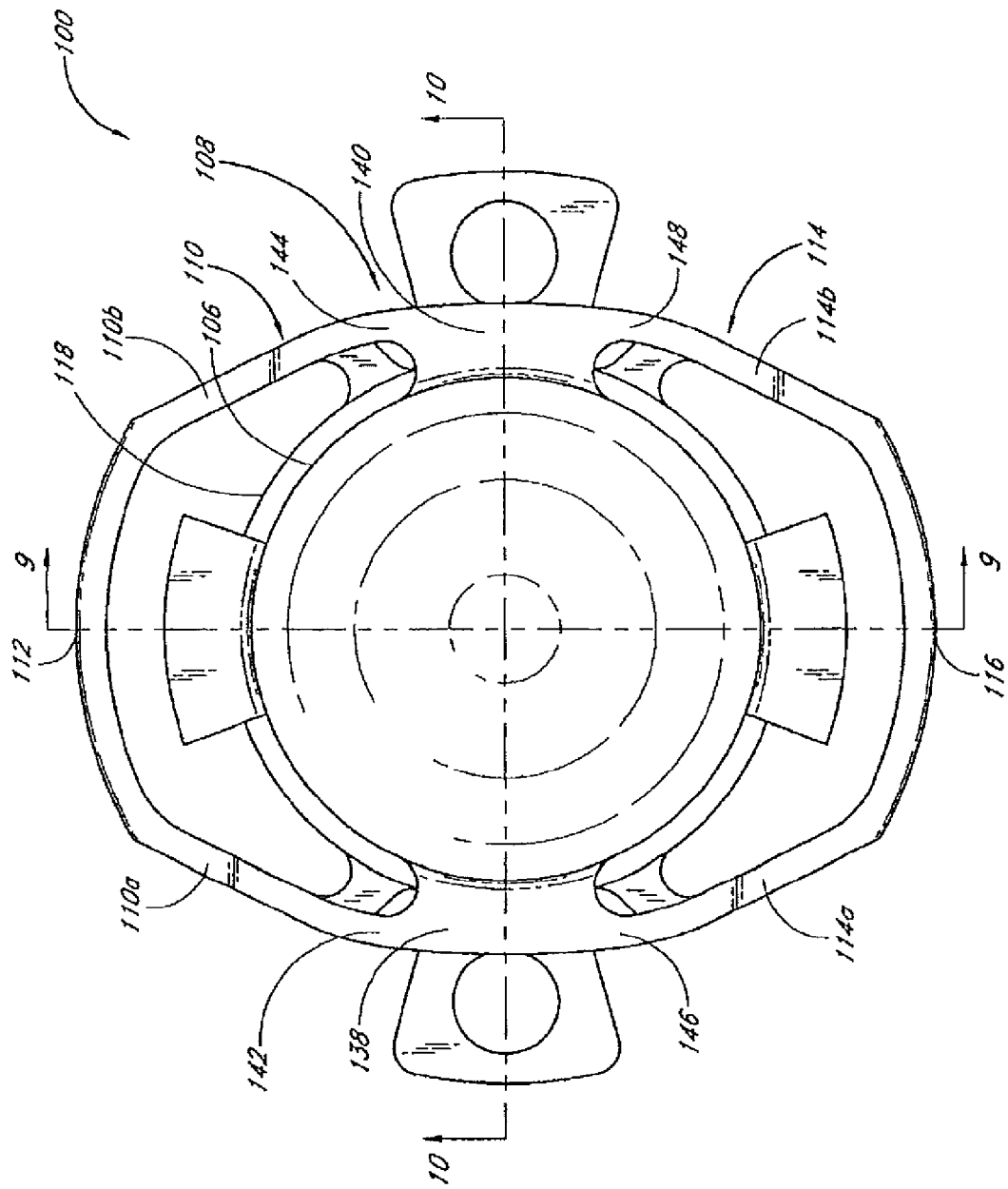
FIG. 7 is a front view of the lens system.

As may be best seen in FIG. 7, the first anterior translation member 110 connects to the anterior viewing element 106 via connection of the left and right arms 110a, 110b to first and second transition members 138, 140 at attachment locations 142, 144. The second anterior translation member 114 connects to the anterior viewing element 106 via connection of left and right arms 114a, 114b to the first and second transition members 138, 140 at attachment locations 146, 148. This is a presently preferred arrangement for the first and second anterior translation members 110, 114; alternatively, the first and second anterior translation members 110, 114 could be connected directly to the anterior viewing element 106, as is the case with the connection of the first and second posterior translation members 122, 124 to the posterior viewing element 118. In some embodiments, at least one of attachment points 142, 144, 146, and 148 may comprise at least a portion of the plurality of silicon-carbon covalent bonds formed by a hydrosilation reaction.

However the connection is established between the first and second anterior translation members 110, 114 and the anterior viewing element 106, it is preferred that the attachment locations 142, 144 corresponding to the first anterior translation member 110 be farther away from the first apex 112 than is the closest edge or the periphery of the anterior viewing element 106. This configuration increases the effective length of the first anterior translation member 110/arms 110a, 110b, in comparison to a direct or straight attachment between the apex 112 and the nearest/top edge of the anterior viewing element 106. For the same reasons, it is preferred that the attachment locations 146, 148 associated with the second anterior translation member 114 be farther away from the second apex 116 than is the closest/bottom edge of the anterior viewing element 106.

As best seen in FIG. 8, the first posterior translation member 122 is preferably connected directly to the posterior viewing element 118 via attachment of the left and right arms 122a, 122b to the element 118 at attachment points 150, 152. Likewise, the second posterior translation member 124 is preferably directly connected to the posterior viewing element 118 via connection of the left and right arms 124a, 124b to the element 118 at attachment points 154, 156, respectively. In some embodiments, at least one of attachment points 150, 152, 154, and 156 may comprise at least a portion of the plurality of silicon-carbon covalent bonds formed by a hydrosilation. In alternative embodiments, the first and second posterior translation members 124, 122 can be connected to the posterior viewing element via intervening members as is done with the anterior viewing element 106. No matter how these connections are made, it is preferred that the attachment locations 150, 152 be spaced further away from the first apex 112 than is the nearest edge or the periphery of the posterior viewing element 118. Similarly, it is preferred that the attachment locations 154, 156 be spaced further away from the second apex 116 than is the closest edge of the posterior viewing element 118.

By increasing the effective length of some or all of the translation members 110, 114, 122, 124 (and that of the arms 110a, 110b, 114a, 114b, 122a, 122b, 124a, 124b where such structure is employed), the preferred configuration of the attachment locations 142, 144, 146, 148, 150, 152, 154, 156 relative to the first and second apices 112, 116 enables the anterior and/or posterior viewing elements 106, 118 to move with respect to one another a greater distance along the optical axis, for a given angular displacement of the anterior and/or posterior translation members. This arrangement thus facilitates a more responsive spring system for the lens system 100 and minimizes material fatigue effects associated with prolonged exposure to repeated flexing.

In the illustrated embodiment, the attachment location 142 of the first anterior translation member 110 is spaced from the corresponding attachment location 146 of the second anterior translation member 114 along the periphery of the anterior viewing element, and the same relationship exists between the other pairs of attachment locations 144, 148; 150, 154; and 152, 156. This arrangement advantageously broadens the support base for the anterior and posterior viewing elements 106, 118 and prevents them from twisting about an axis parallel to the lateral axis, as the viewing elements move between the accommodated and unaccommodated positions.

It is also preferred that the attachment locations 142, 144 of the first anterior translation member 110 be located equidistant from the first apex 112, and that the right and left arms 100a, 110b of the member 110 be equal in length. Furthermore, the arrangement of the attachment locations 146, 148, arms 114a, 114b and second apex preferably mirrors that recited above regarding the first anterior translation member 110, while the apices 112, 116 are preferably equidistant from the optical axis and are situated 180 degrees apart. This configuration maintains the anterior viewing element 106 orthogonal to the optical axis as the viewing element 106 moves back and forth and the anterior viewing element flexes.

For the same reasons, a like combination of equidistance and equal length is preferred for the first and second posterior translation members 122, 124 and their constituent arms 122a, 122b, 124a, 124b and attachment points 150, 152, 154, 156, with respect to the apices 112, 116. However, as shown the arms 122a, 122b, 124a, 124b need not be equal in length to their counterparts 110a, 110b, 114a, 114b in the first and second anterior translation members 110, 114.

Where any member or element connects to the periphery of the anterior or posterior viewing elements 106, 118, the member defines a connection geometry or attachment area with a connection width W and a connection thickness T (see FIG. 5 and the example illustrated therein, of the connection of the second posterior translation member 124 to the posterior viewing element 118). For purposes of clarity, the connection width is defined as being measured along a direction substantially parallel to the periphery of the viewing element in question, and the connection thickness is defined as measured along a direction substantially perpendicular to the periphery of the viewing element. (The periphery itself is deemed to be oriented generally perpendicular to the optical axis as shown in FIG. 5.) Preferably, no attachment area employed in the lens system 100 has a ratio of width to thickness less than 3. It has been found that such a geometry reduces distortion of the viewing element/optic due to localized forces. For the same reasons, it is also preferred that each of the translation members 110, 114, 122, 124 be connected to the periphery of the respective viewing elements at least two attachment areas, each having the preferred geometry discussed above.

As discussed above, each of the anterior viewing element 106 and the posterior viewing element 118 preferably comprises an optic having refractive power. In one preferred embodiment, the anterior viewing element 106 comprises a biconvex lens having positive refractive power and the posterior viewing element 118 comprises a convexo-concave lens having negative refractive power. The anterior viewing element 106 may comprise a lens having a positive power advantageously less than 55 diopters, preferably less than 40 diopters, more preferably less than 35 diopters, and most preferably less than 30 diopters. The posterior viewing element 118 may comprise a lens having a power which is advantageously between −25 and 0 diopters, and preferably between −25 and −15 diopters. In other embodiments, the posterior viewing element 118 comprises a lens having a power which is between −15 and 0 diopters, preferably between −13 and −2 diopters, and most preferably between −10 and −5 diopters. Advantageously, the total power of the optic(s) employed in the lens system 100 is about 5-35 diopters; preferably, the total power is about 10-30 diopters; most preferably, the total power is about 15-25 diopters. (As used herein, the term "diopter" refers to lens or system power as measured when the lens system 100 has been implanted in the human eye in the usual manner.) It should be noted that if materials having a high index of refraction (e.g., higher than that of silicone) are used, the optics may be made thinner which facilitates a wider range of motion for the optics. This in turn allows the use of lower-power optics than those specified above. In addition, higher-index materials allow the manufacture of a higher-power lens for a given lens thickness and thereby reduce the range of motion needed to achieve a given range of accommodation.

Some lens powers and radii of curvature presently preferred for use with an embodiment of the lens system 100 with optic(s) having a refractive index of about 1.432 are as follows: a +31 diopter, biconvex lens with an anterior radius of curvature of 5.944 mm and a posterior radius of curvature of 5.944 mm; a +28 diopter, biconvex lens with an anterior radius of curvature of 5.656 mm and a posterior radius of curvature of 7.788 mm; a +24 diopter, biconvex lens with an anterior radius of curvature of 6.961 mm and a posterior radius of curvature of 8.5 mm; a −10 diopter, biconcave lens with an anterior radius of curvature of 18.765 mm and a posterior radius of curvature of 18.765 mm; a −8 diopter, concavo-convex lens with an anterior radius of curvature of between 9 mm and 9.534 mm and a posterior radius of curvature of 40 mm; and a −5 diopter, concavo-convex lens with an anterior radius of curvature of between 9 mm and 9.534 mm and a posterior radius of curvature of 20 mm. In one embodiment, the anterior viewing element comprises the +31 diopter lens described above and the posterior viewing element comprises the −10 diopter lens described above. In another embodiment, the anterior viewing element comprises the +28 diopter lens described above and the posterior viewing element comprises the −8 diopter lens described above. In another embodiment, the anterior viewing element comprises the +24 diopter lens described above and the posterior viewing element comprises the −5 diopter lens described above.

The combinations of lens powers and radii of curvature specified herein advantageously minimize image magnification. However, other designs and radii of curvature provide modified magnification when desirable.

The lenses of the anterior viewing element 106 and the posterior viewing element 118 are relatively moveable as discussed above; advantageously, this movement is sufficient to produce an accommodation of at least one diopter, preferably at least two diopters and most preferably at least three diopters. In other words, the movement of the optics relative to each other and/or to the cornea is sufficient to create a difference between (i) the refractive power of the user's eye in the accommodated state and (ii) the refractive power of the user's eye in the unaccommodated state, having a magnitude expressed in diopters as specified above. Where the lens system 100 has a single optic, the movement of the optic relative to the cornea is sufficient to create a difference in focal power as specified above.

Advantageously, the lens system 100 can be customized for an individual patient's needs by shaping or adjusting only one of the four lens faces, and thereby altering the overall optical characteristics of the system 100. This in turn facilitates easy manufacture and maintenance of an inventory of lens systems with lens powers which will fit a large population of patients, without necessitating complex adjustment procedures at the time of implantation. It is contemplated that all of the lens systems in the inventory have a standard combination of lens powers, and that a system is fitted to a particular patient by simply shaping only a designated "variable" lens face. This custom-shaping procedure can be performed to-order at a central manufacturing facility or laboratory, or by a physician consulting with an individual patient. In one embodiment, the anterior face of the anterior viewing element is the designated sole variable lens face. In another embodiment, the anterior face of the posterior viewing element is the only variable face. However, any of the lens faces is suitable for such designation. The result is minimal inventory burden with respect to lens power (all of the lens systems in stock have the same lens powers) without requiring complex adjustment for individual patients (only one of the four lens faces is adjusted in the fitting process).

VI. Mold Tooling

While there are many methods known in the art which may be adapted to create the intraocular lens systems described herein, in some embodiments, the lens system may be prepared using a mold system.

While many mold systems are known in the art which may be used to prepare a lens system described herein, FIGS. 19-34 depict a mold system 500 which is suitable for molding the lens system 100 depicted in FIG. 3-18. The mold system 500 generally comprises a first mold 502, a second mold 504 and a center mold 506. The center mold 506 is adapted to be positioned between the first mold 502 and the second mold 504 so as to define a mold space for injection molding or compression molding the lens system 100. The mold system 500 may be formed from suitable metals, high-impact-resistant plastics or a combination thereof, and can be produced by conventional machining techniques such as lathing or milling, or by laser or electrical-discharge machining. The mold surfaces can be finished or modified by sand blasting, etching or other texturing techniques.

The first mold 502 includes a first mold cavity 508 with a first anterior mold face 510 surrounded by an annular trough 512 and a first perimeter mold face 514. The first mold 502 also includes a projection 516 which facilitates easier mating with the second mold 504.

The center mold 506 includes a first center mold cavity 518 which cooperates with the first mold cavity 508 to define a mold space for forming the anterior portion 102 of the lens system 100. The first center mold cavity 518 includes a central anterior mold face 520 which, upon placement of the center mold 506 in the first mold cavity 508, cooperates with the first anterior mold face 510 to define a mold space for the anterior viewing element 106. In so doing, the first anterior mold face 510 defines the anterior face of the anterior viewing element 106 and the central anterior mold face 520 defines the posterior face of the anterior viewing element 106. In fluid communication with the chamber formed by the first anterior mold face 510 and the central anterior mold face 520 are lateral channels 522, 524 (best seen in FIG. 27) which form spaces for molding the first and second transition members 138, 140, along with the arms 110a, 110b of the first anterior translation member 110 as well as the arms 114a, 114b of the second anterior translation member 114. The first center mold cavity 518 also includes retention member cavities 526, 528 which define spaces for molding the first and second retention members 128, 130 to the anterior viewing element 106.

The second mold 504 includes a second mold cavity 530 with a second posterior mold space 532, a generally cylindrical transition 534 extending therefrom and connecting to a second perimeter mold face 536. Lateral notches 538, 540 (best seen in FIGS. 22 and 23) are formed in the second perimeter mold face 536. The second mold 504 also includes an input channel 542 connected to an input channel opening 544 for introducing material into the mold system 500. Also formed in the second mold 504 is an output channel 546 and an output channel opening 548. A generally cylindrical rim 550 is included for mating with the projection 516 of the first mold 502.

The center mold 506 includes a second center mold cavity 552 which cooperates with the second mold cavity 530 to define a mold space for the posterior portion 104 of the lens system 100. The second center mold cavity 552 includes a central posterior mold face 554 which, upon placement of the center mold 506 in engagement with the second mold cavity 530, cooperates with the second posterior mold face 532 and the transition 534 to define a chamber for forming the posterior viewing element 118. In fluid communication with the chamber formed by the central posterior mold face 554 and the second posterior mold face 532 are lateral channels 556, 558, 560, 562 which provide a mold space for forming the arms 122a, 122b of the first posterior translation member 122 and the arms 124a, 124b of the second posterior translation member 124. The second center mold cavity 552 includes lateral projections 564, 566 which coact with the notches 538, 540 formed in the second mold cavity 530. The chambers formed therebetween are in fluid communication with the chamber defined by the central posterior mold face 554 and the second posterior mold face 532 to form the first and second distending members 134, 136 integrally with the posterior viewing element 118.

The center mold 506 includes a first reduced-diameter portion 568 and a second reduced-diameter portion 570 each of which, upon assembly of the mold system 500, defines a mold space for the apices 112, 116 of the lens system 100.

In use, the mold system 500 is assembled with the center mold 506 positioned between the first mold 502 and the second mold 504. Once placed in this configuration, the mold system 500 is held together under force by appropriate techniques, and lens material is introduced into the mold system 500 via the input channel 542. The lens material then fills the space defined by the first mold 502, second mold 504, and the center mold 506 to take on the shape of the finished lens system 100.

The mold system 500 is then disassembled, and in one embodiment the lens system 100 is left in position on the center mold 506 after removal of the first and second molds 502, 504. This technique has been found to improve the effectiveness of any polishing/tumbling/deflashing procedures which may be performed. Whether or not these or any other additional process steps are performed, the lens system 100 is preferably removed from the center mold 506 while maintaining the interconnection of the various components of the lens system 100.

In another embodiment, the lens system 100 or a portion thereof is formed by a casting or liquid-casting procedure in which one of the first or second molds is first filled with a liquid and the center mold is placed then into engagement with the liquid-filled mold. The exposed face of the center mold is then filled with liquid and the other of the first and second molds is placed into engagement with the rest of the mold system. The liquid is allowed or caused to set/cure and a finished casting may then removed from the mold system.

The mold system 500 can advantageously be employed to produce a lens system 100 as a single, integral unit. Alternatively, various portions of the lens system 100 can be separately molded, casted, machined, etc. and subsequently assembled to create a finished lens system. Assembly can be performed as a part of centralized manufacturing operations; alternatively, a physician can perform some or all of the assembly before or during the implantation procedure, to select lens powers, biasing members, system sizes, etc. which are appropriate for a particular patient.

The center mold 506 is depicted as comprising an integral unit with first and second center mold cavities 518, 552. Alternatively, the center mold 506 may have a modular configuration whereby the first and second mold cavities 518, 552 may be interchangeable to adapt the center mold 506 for manufacturing a lens system 100 according to a desired prescription or specification, or to otherwise change the power(s) of the lenses made with the mold. In this manner the manufacture of a wide variety of prescriptions may be facilitated by a set of mold cavities which can be assembled back-to-back or to opposing sides of a main mold structure.

The molds may be manufactured by a number of different methods, including those disclosed in U.S. Pat. No. 6,884, 261.

The mold system described herein may be modified as needed to create the different lens systems described herein. The examples below describe how an accommodative lens system with two viewing elements and a silicone haptic may be prepared where both viewing elements are acrylic copolymer, or where one is acrylic copolymer and the other is silicone. These procedures may be adapted to other device configurations. For example, acrylic could be injected into the molding system instead of silicone as described below to provide an acrylic haptic. Alternatively, a combination of silicone and acrylic could be injected, either simultaneously, serially, or in some other manner. Alternatively, thinner sheets could be cast and coated with silicone, or smaller diameter discs could be cut and a silicon frame then added to the circumference of the lens, either before placing the viewing element in the mold, or by adding a feature to the mold. Many other permutations are also possible. Furthermore, other methods known in the art may be used instead of, or combined with, the methods described herein.

VII. Experimental Examples

The copolymers of Examples 1-5 were prepared according to the following procedure. All the components were added into a three necked round bottom flask of IL equipped with magnetic stirrer, nitrogen gas purging system, and mounted with a Teflon tube connected with 0.2 um filter system. With stirring, the mixture was purged by bubbling nitrogen gas through the mixture for 1 hour at room temperature. The mixture was then transferred into a sheet casting chamber. The sheets were cast to 3 mm thickness at about 50-80° C. for 8-16 hours and then at about 125-140° C. for another 8 hours. The sheets were cooled to room temperature and cut to an appropriate size for extraction (6-20 mm diameter round disks). The round disks were then extracted with methanol or ethanol, or a mixture of methanol and ethanol using a soxhlet extractor for at least 24 hours, and dried at 0° C. for 24 hours, and then at 70° C. for another 48 hours until the weight was constant.

Example 1

A copolymer was prepared as described above using the following components: 28.70% (w/w) ethyl methacrylate; 54.30% (w/w) n-butyl acrylate; 5.66% (w/w) ethylene glycol dimethacrylate; 1.33% (w/w) 2-[3-(2h-benzotriazol-2-yl)-4-hydroxyphenyl]ethyl methacrylate; 10.00% (w/w) methacryloxypropyltris(vinyldimethylsil oxy)silane; 0.125% (w/w) and 2,2'-azobisisobutyronitrile. The crosslinked copolymer had a refractive index of 1.476 at 25° C., the tensile strength was greater than 500 psi, elongation was greater than 100%, and shore A hardness was 60 at 20° C.

Example 2

A copolymer was prepared as described above using the following components: 25.50% (w/w) ethyl methacrylate; 52.50% (w/w) n-butyl acrylate; 5.66% (w/w) ethylene glycol dimethacrylate; 1.33% (w/w) 2-[3-(2h-benzotriazol-2-yl)-4-hydroxyphenyl]ethyl methacrylate; 15.00% (w/w) methacryloxypropyltris(vinyldimethylsiloxy)silane; and 0.125% (w/w) 2,2'-azobisisobutyronitrile. The crosslinked copolymer had a refractive index of 1.474 at 25° C., tensile strength was greater than 500 psi, elongation was greater than 80%, and shore A hardness was 67 at 20° C.

Example 3

A copolymer was prepared as described above using the following components: 18.60% (w/w) methylstyrene; 18.10% (w/w) ethyl methacrylate; 46.50% (w/w) n-butyl acrylate; 5.66% (w/w) ethylene glycol dimethacrylate; 1.33% (w/w) 2-[3-(2h-benzotriazol-2-yl)-4-hydroxyphenyl]ethyl methacrylate; 10.00% (w/w) methacryloxy propyltris(vinyldimethylsiloxy)silane; and 0.125% (w/w) 2,2'-azobisisobutyronitrile. The crosslinked copolymer had a refractive index of 1.499 at 25° C., tensile strength was greater than 500 psi, elongation was greater than 80%, and shore A hardness was 65 at 20° C.

Example 4

A copolymer was prepared as described above using the following components: 17.4% (w/w) methylstyrene; 17.2% (w/w) ethyl methacrylate; 44.3% (w/w) n-butyl acrylate; 5.39% (w/w) ethylene glycol dimethacrylate; 1.26% (w/w) 2-[3-(2h-benzotriazol-2-yl)-4-hydroxyphenyl]ethyl methacrylate; 14.40% (w/w) methacryloxy propyltris(vinyldimethylsiloxy)silane; and 0.12% (w/w) 2,2'-azobisisobutyronitrile. The crosslinked copolymer had a refractive index of 1.499 at 25° C., tensile strength greater than 500 psi, elongation greater than 80%, and shore A hardness of 70 at 20° C.

Example 5

A copolymer was prepared as described above using the following components: 17.4% (w/w) methylstyrene; 21.2% (w/w) ethyl methacrylate; 50.6% (w/w) n-butyl acrylate; 5.39% (w/w) ethylene glycol dimethacrylate; 1.26% (w/w) 2-[3-(2h-benzotriazol-2-yl)-4-hydroxyphenyl]ethyl methacrylate; 4.10% (w/w) methacryloxypropyl tris(vinyldimethylsiloxy)silane; 0.12% (w/w) 2,2'-azobisisobutyronitrile. The crosslinked copolymer had a refractive index of 1.498 at 25° C., tensile strength greater than 500 psi, elongation greater than 80%, shore A hardness of 60 at 20° C., and glass transition temperature of 11.0° C.

Example 6

Preparation of an Intraocular Lens
Hydrophobic Acrylic Material Sheet Casting

All the components were added into a three necked round bottom flask of 1 L equipped with magnetic stirrer, nitrogen gas purging system, and mounted with a Teflon tube connected with 0.2 um filter system. With stirring, the mixture was purged by bubbling nitrogen gas through the mixture for 1 hour at room temperature. The mixture was then transferred into a sheet casting chamber. The sheets were cast to 3 mm thickness at about 65° C. for 16 hours and then at about 140° C. for another 8 hours. The sheets were cooled to room temperature, separated, and cut to an appropriate size (6-20 mm diameter round disks) for extraction.

Hydrophobic Acrylic Button Extraction

The hydrophobic acrylic buttons are extracted with methanol or ethanol, or a mixture of methanol and ethanol using a soxhlet extractor for at least 24 hours, and dried at 35° C. for 24 hours, and then at 70° C. for another 48 hours until the weight was constant.

Anterior and Posterior Lenses Preparation

The extracted hydrophobic acrylic buttons are lathe cut to form anterior lens and posterior lenses at a temperature below 0° C.

Hydrophobic Acrylic Lens Treatment

Hydrophobic anterior and posterior soft acrylic lenses may be pretreated prior to molding or bonding with a silicone material with a solution of Si—H containing crosslinker, such as X,L-1,2,3 (Nusil); X, L-1,1,1 (Nusil); tetrakis(dimethylsiloxy)silane, etc., in heptanes or another hydrocarbon solvent for about 0 minutes to about 5 minutes, or about 1 minute to about 3 minutes. The concentration of Si—H containing crosslinkers in heptanes is from about 1% to 100%, or about 10% to about 20%. After the hydrophobic acrylic lenses are treated, they are immediately rinsed at least once with fresh heptanes or another hydrocarbon solvent to remove extra crosslinker on the surface region of the lenses. The lenses are then dried at about 85° C. with or without vacuum for at least 1 hour.

Anterior and Posterior Hydrophobic Acrylic Dual Optic Lens Molding Procedure

Figure 20:
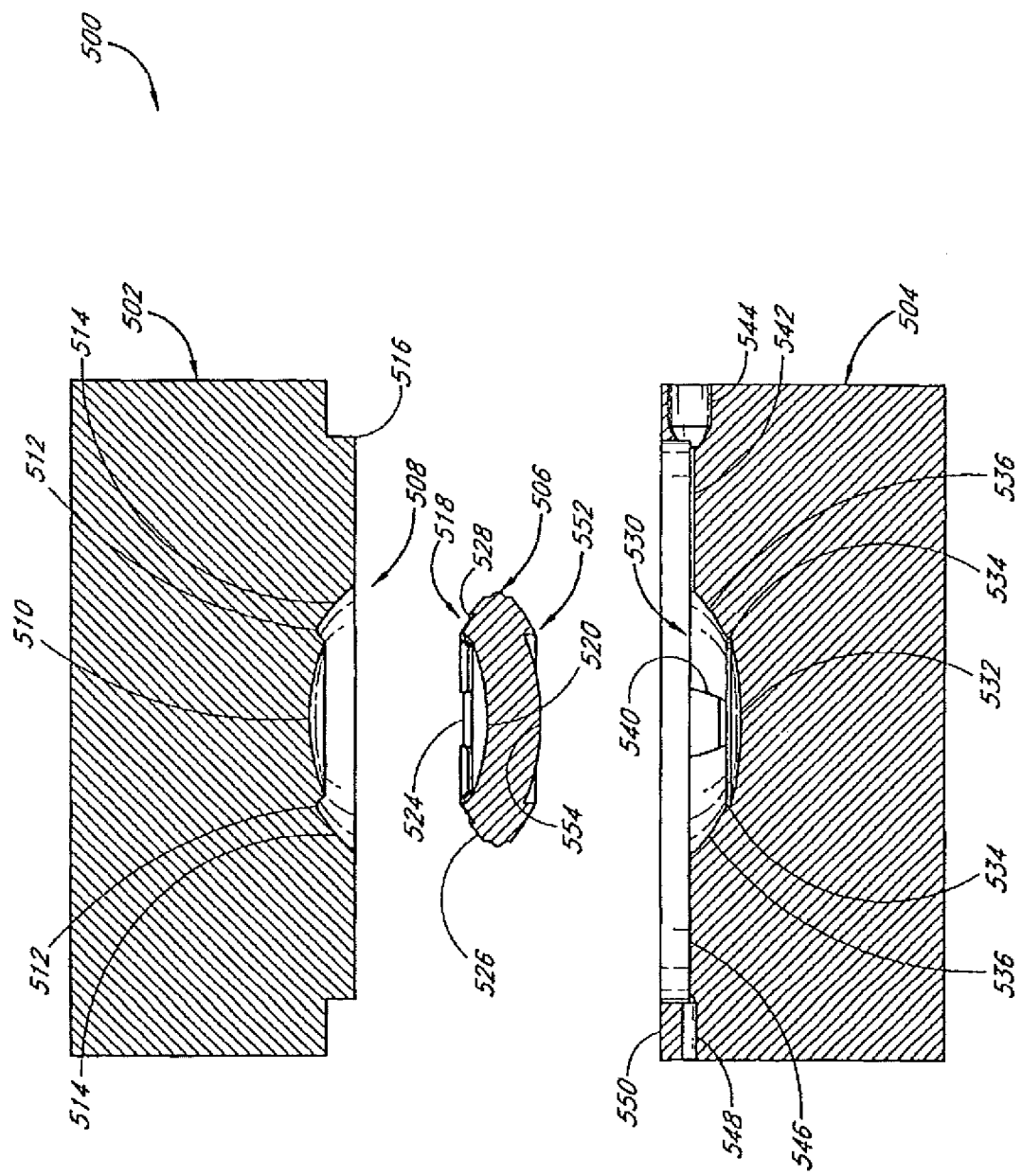
FIG. 20 is a side sectional view of the lens system.
Figure 21:
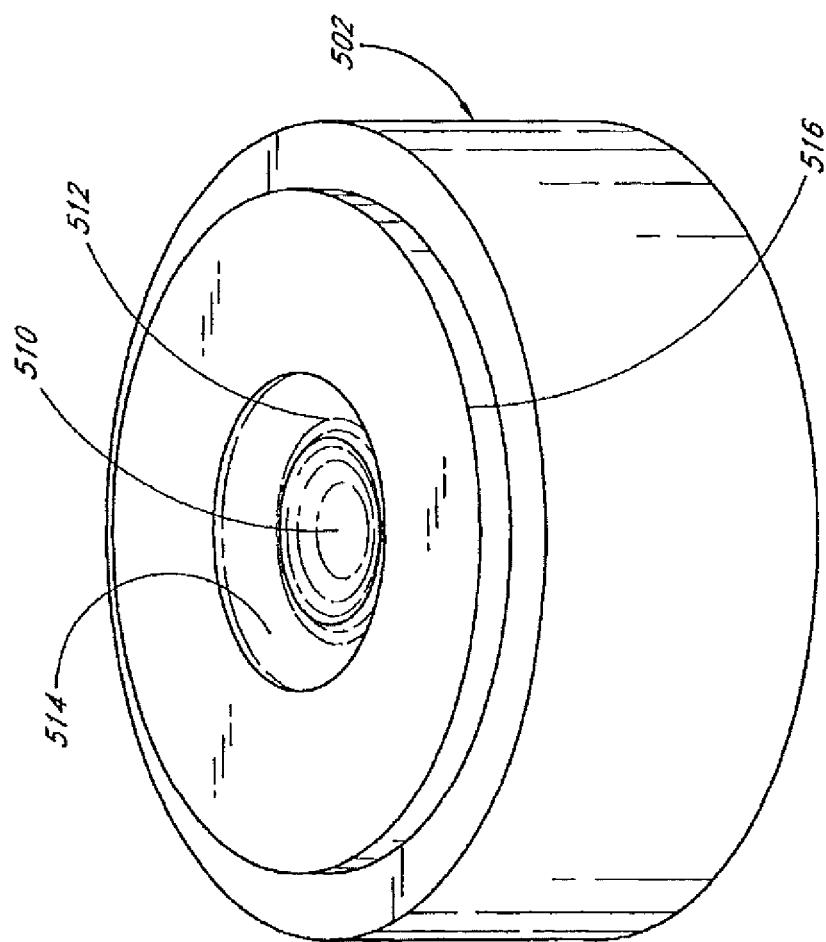
FIG. 21 is a perspective view of a first mold portion.
Figure 22:
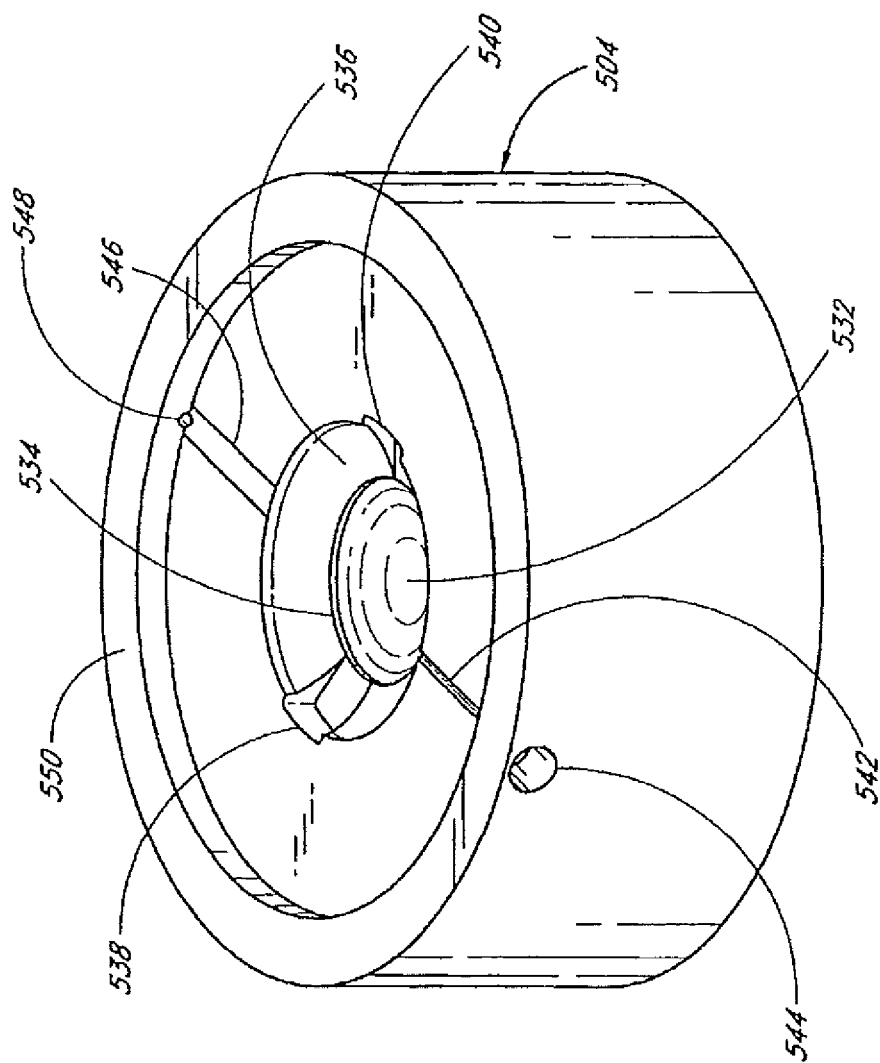
FIG. 22 is a perspective view of a second mold portion.
Figure 23:
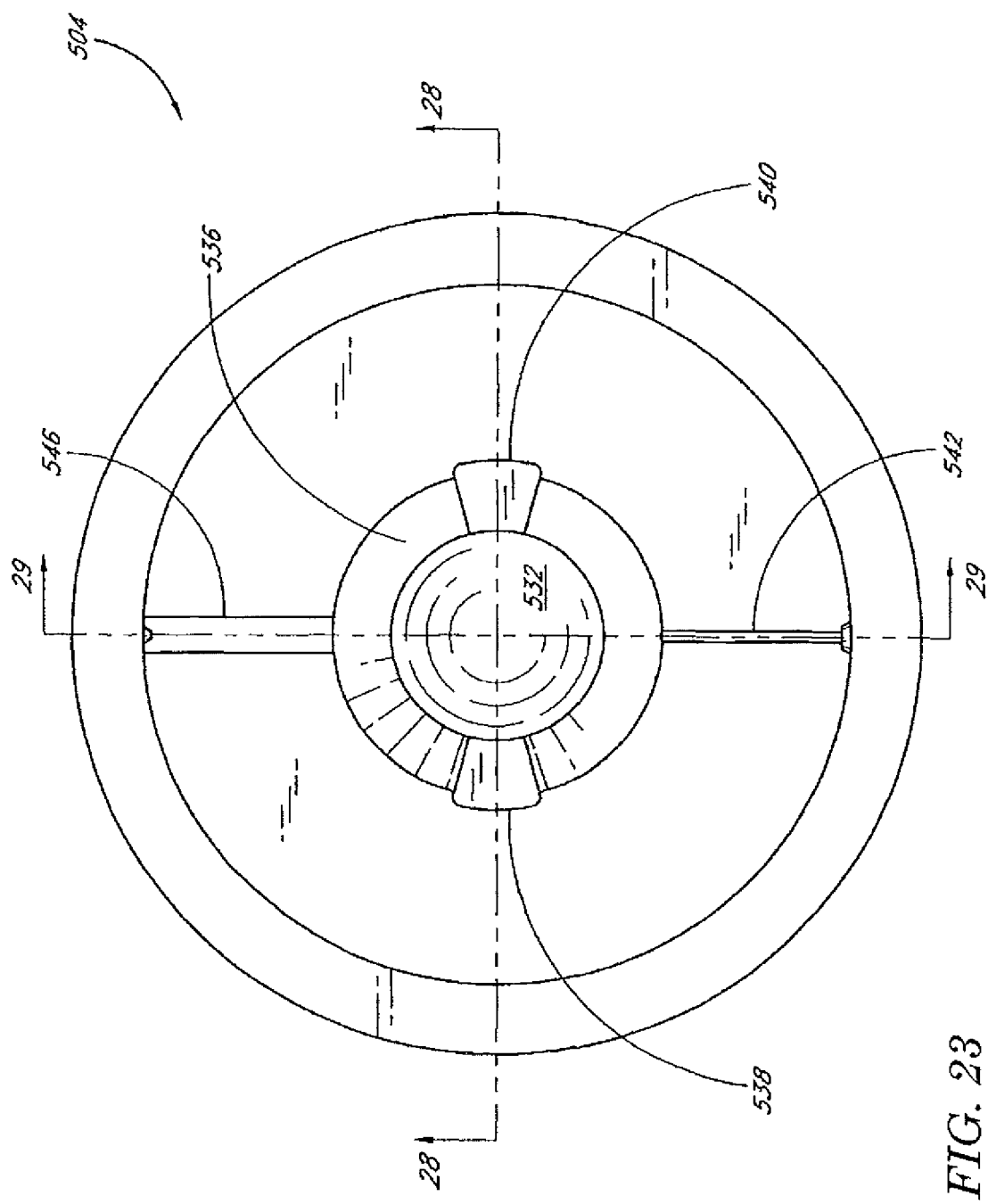
FIG. 23 is a top view of the second mold portion.
Figure 24:
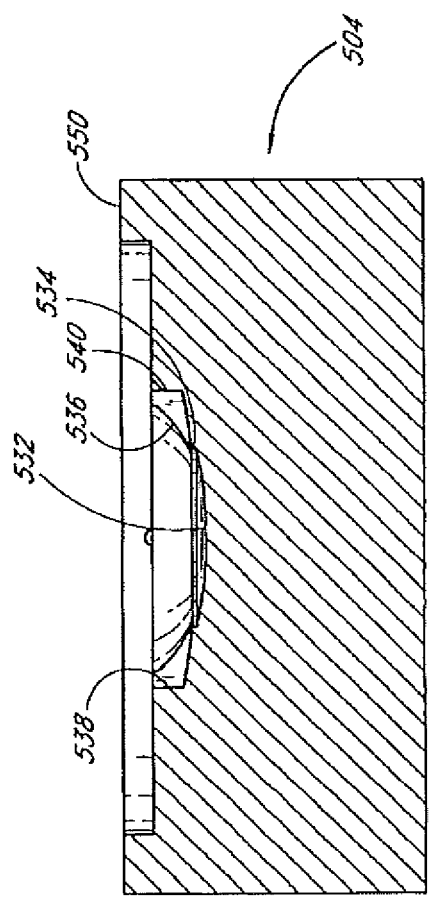
FIG. 24 is a side sectional view of the mold system.
Figure 25:
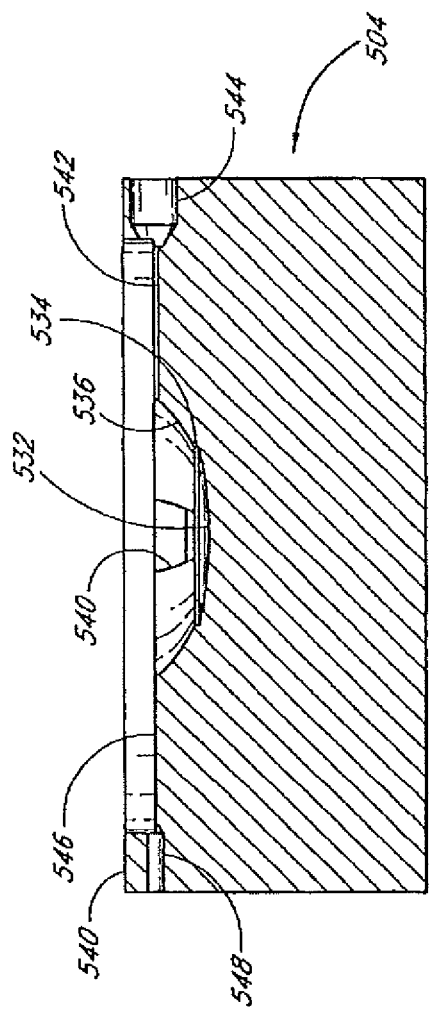
FIG. 25 is a perspective view of a first mold portion.
Figure 26:
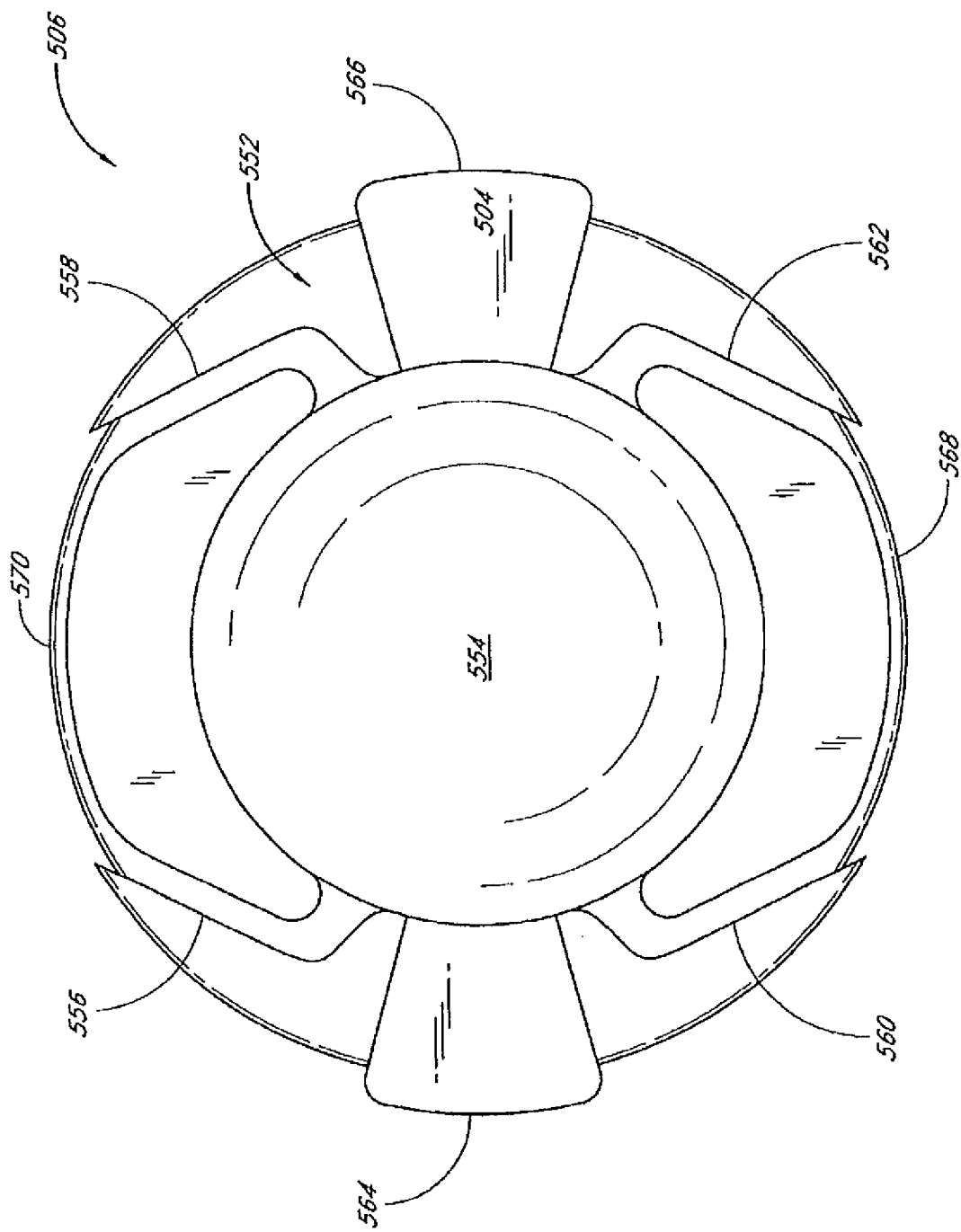
FIG. 26 is a bottom view of a second mold portion.
Figure 27:
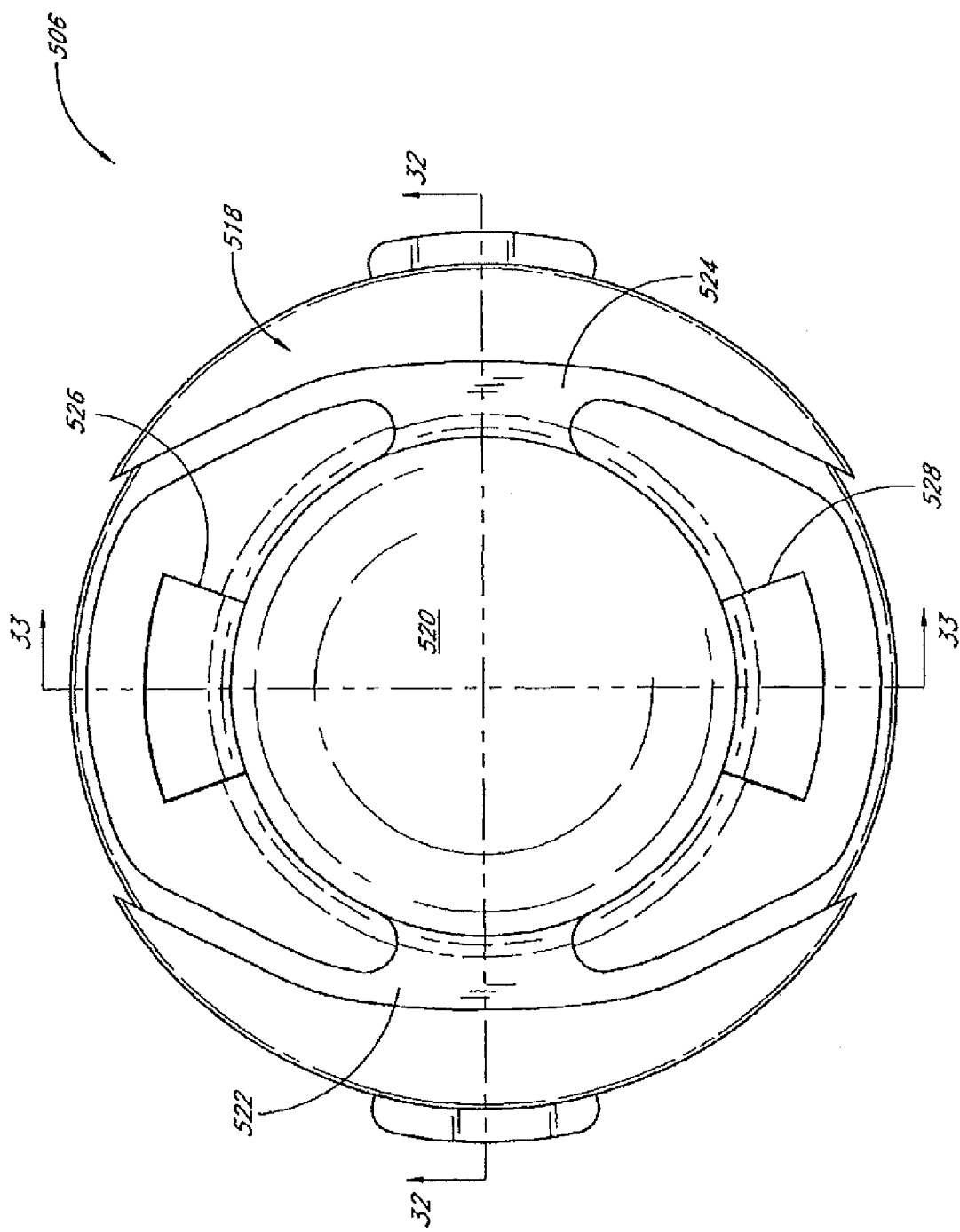
FIG. 27 is a top view of the second mold portion.
Figure 29:
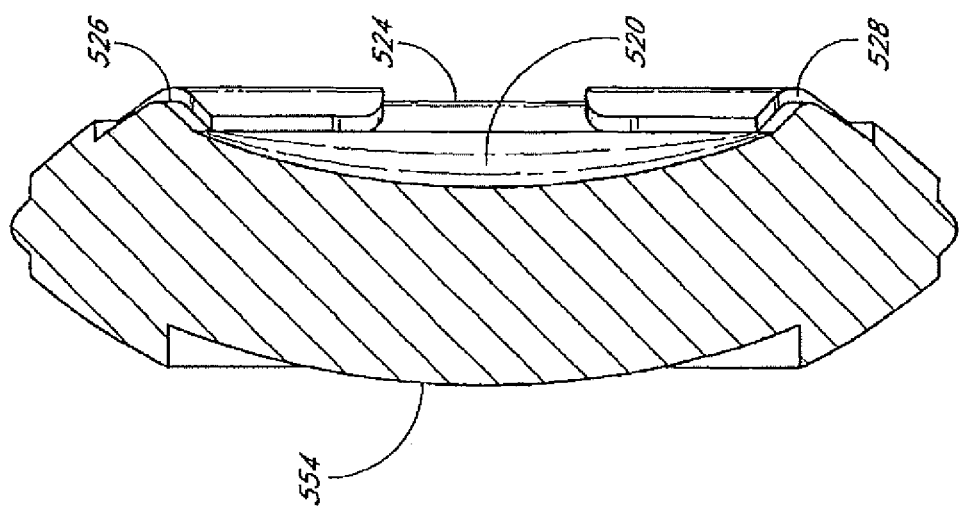
FIG. 29 is another sectional view of the center mold portion.
Figure 28:
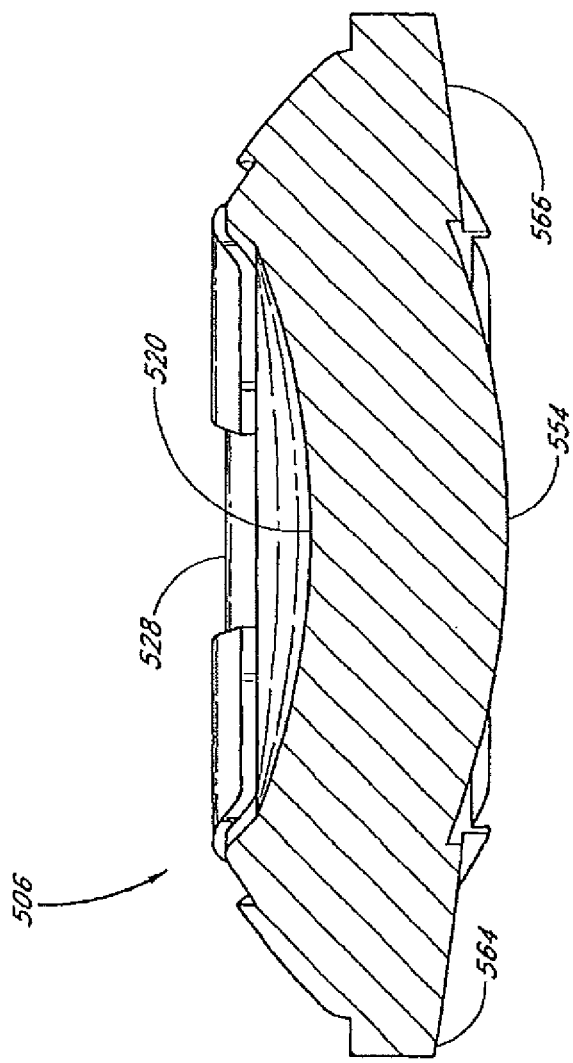
FIG. 28 is a sectional view of the center mold portion.
Figure 30:
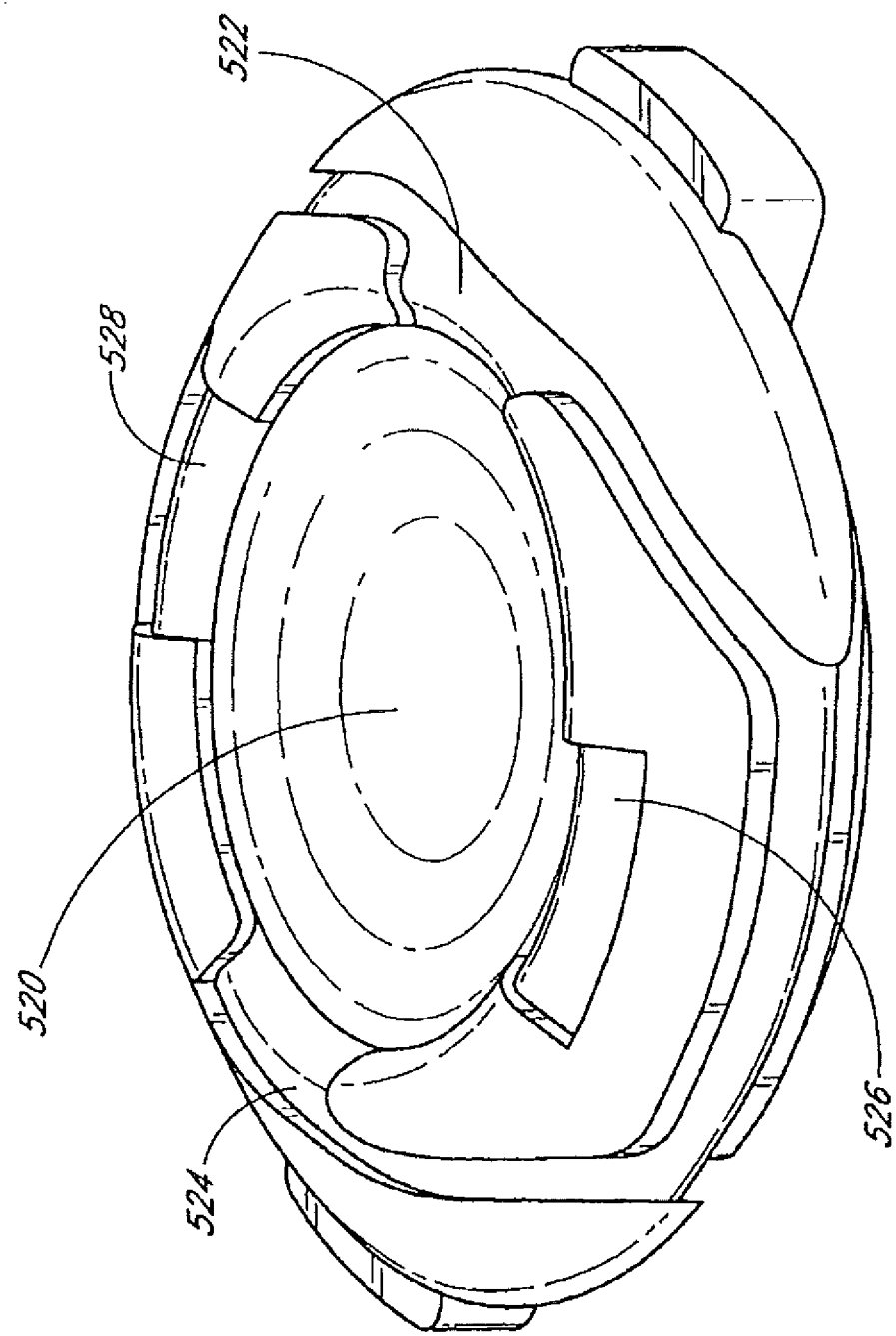
FIG. 30 is a perspective view of the center mold portion.

Referring to FIG. 20, the hydrophobic acrylic posterior lens is placed in the second mold cavity 530 of the second mold 504, and the anterior lens is placed in the first mold cavity 508 of the first mold 502. The silicone material is then injected on the surfaces of hydrophobic acrylic posterior lens and anterior lens which face out of the molds. The center mold 508 is then properly loaded onto the second mold 504, and the first mold 502 is closed on the second mold 504. The mold is clamped under appropriate pressure and the lens is molded at 115° C. for at least 120 minutes to allow the silicone material to cure and for the silicon-carbon covalent bonds to form between the silicone and acrylic components.

Anterior Silicone and Posterior Hydrophobic Acrylic Dual Optic Lens Molding Procedure The hydrophobic acrylic posterior lens is placed in the second mold cavity 530 of the second mold 504. The silicone material is then injected on the surface of the hydrophobic acrylic posterior lens which faces out of the second mold 504 and into the first mold cavity 508 of the first mold 502. The center mold 508 is then properly loaded onto the second mold 504, and the first mold 502 is closed on the second mold 504. The mold is clamped and the lens is molded at 115° C. for at least 120 minutes to allow the silicone material to cure and for the silicon-carbon covalent bonds to form between the silicone and acrylic components.

Posterior Silicone and Anterior Hydrophobic Dual Optic Lens Molding Procedure

The hydrophobic acrylic posterior lens is placed in the first mold cavity 508 of the first mold 502. The silicone material is then injected on the surface of hydrophobic acrylic anterior lens which faces out of the mold and into the second mold cavity 530 of the second mold 504. The center mold 508 is then properly loaded onto the second mold 504, and the first mold 502 is closed on the second mold 504. The mold is clamped and the lens is molded at 115° C. for at least 120 minutes to allow the silicone material to cure and for the silicon-carbon covalent bonds to form between the silicone and acrylic components.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. An intraocular lens comprising:
    an optic body comprising a first hydrophobic soft acrylic copolymer; and
    a haptic comprising a first silicone connected to the optic body;
    wherein the first hydrophobic soft acrylic copolymer comprises:
        an acrylate recurring unit; and
        an optionally substituted vinylaryl recurring unit;
    wherein a portion of at least one of the recurring units comprises a vinyldialkylsiloxy pendant group, and further wherein the first hydrophobic soft acrylic copolymer is prepared by a process comprising reacting monomer 1a, monomer 2, and monomer 3a; and monomer 4 or monomer 5a;
    wherein monomer 1a represents about 20% to about 70% of the total weight of all monomers present in the process and is represented by a formula:

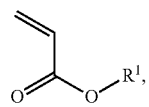

monomer 2 represents about 10% to about 40% of the total weight of all monomers present in the process and is represented by a formula:

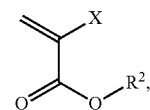

monomer 3a represents about 5% to about 40% of the total weight of all monomers present in the process and is represented by a formula:

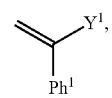

monomer 4 is represented by a formula:

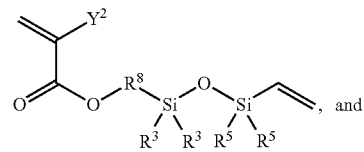, and monomer 5a represents about 1% to about 20% of the total weight of all monomers present in the process and is represented by a formula:

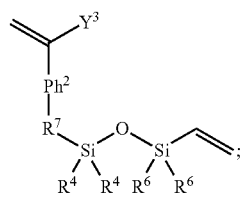

$R^1$ and $R^2$ are independently $C_{1-12}$ alkyl or optionally substituted phenyl;
X is $C_{1-4}$ alkyl;
$Y^1$, $Y^2$, and $Y^3$ are independently H or $C_{1-4}$ alkyl;
$Ph^1$ and $Ph^2$ are independently optionally substituted phenyl;
each $R^3$ and each $R^4$ is independently $C_{1-4}$ alkyl or

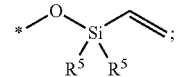

each $R^5$ and each $R^6$ is independently $C_{1-4}$ alkyl;
$R^7$ is a covalent bond or $C_{1-6}$ alkyl; and
$R^8$ is $C_{1-6}$ alkyl.

2. The intraocular lens of claim 1, wherein the optic body consists essentially of the hydrophobic soft acrylic copolymer.

3. The intraocular lens of claim 1, wherein a portion of the optic body is the hydrophobic soft acrylic copolymer.

4. The intraocular lens of claim 3, wherein the optic body further comprises a second silicone.

5. The intraocular lens of claim 1, which is a dual optic accommodative lens comprising:
- an anterior optic body comprising the first hydrophobic soft acrylic copolymer;
- a posterior optic body comprising a second hydrophobic soft acrylic copolymer; and
- a haptic comprising the first silicone connecting the anterior optic body to the posterior optic body.

6. The intraocular lens of claim 1, which is a dual optic accommodative lens comprising:
- an anterior optic body comprising the first hydrophobic soft acrylic copolymer;
- a posterior optic body comprising a second silicone; and
- wherein the haptic is also connected to the posterior optic body.

7. The intraocular lens of claim 1, which is a dual optic accommodative lens comprising:
- an anterior optic body comprising a second silicone;
- a posterior optic body comprising the first hydrophobic soft acrylic copolymer; and
- wherein the haptic is also connected to the posterior optic body.

* * * * *